(12) United States Patent
Larrick et al.

(10) Patent No.: US 10,654,925 B2
(45) Date of Patent: May 19, 2020

(54) ANTI-MARINOBUFAGENIN ANTIBODIES AND USES THEREOF

(71) Applicant: CTS Biopharma LLC, Sunnvale, CA (US)

(72) Inventors: James W. Larrick, Sunnyvale, CA (US); John M. Wages, Tupelo, MS (US); Andrew R. Mendelsohn, Palo Alto, CA (US); Vikram Sharma, San Francisco, CA (US); Bo Yu, Sunnyvale, CA (US)

(73) Assignee: CTS Biopharma LLC, Sunnyvale, CA (US)

( * ) Notice: Subject to any disclaimer, the term of this patent is extended or adjusted under 35 U.S.C. 154(b) by 0 days.

(21) Appl. No.: 16/447,181

(22) Filed: Jun. 20, 2019

(65) Prior Publication Data

US 2019/0389947 A1 Dec. 26, 2019

Related U.S. Application Data

(60) Provisional application No. 62/687,978, filed on Jun. 21, 2018.

(51) Int. Cl.
*C07K 16/18* (2006.01)
*C07K 16/26* (2006.01)

(52) U.S. Cl.
CPC .............. *C07K 16/26* (2013.01); *C07K 16/18* (2013.01); *C07K 2317/24* (2013.01); *C07K 2317/55* (2013.01); *C07K 2317/567* (2013.01); *C07K 2317/622* (2013.01)

(58) Field of Classification Search
None
See application file for complete search history.

(56) References Cited

U.S. PATENT DOCUMENTS 8,038,997 B2 * 10/2011 Bagrov .................. C07K 16/26
424/130.1
2006/0263891 A1 11/2006 Puschett
2010/0158900 A1 6/2010 Bagrov

FOREIGN PATENT DOCUMENTS

WO WO 2016/033489 3/2016
WO WO 2017/015472 1/2017

OTHER PUBLICATIONS

Fedorova et al, Monoclonal antibody to an endogenous bufadienolide, marinobufagenin, reverses preeclampsia-induced Na/K-ATPase . . . , 2008, J. Hypertens. vol. 26, pp. 2414-2425.
Fedorova et al, Antibody to marinobufagenin reverses placenta-induced fibrosis of umbilical arteries in preeclampsia, 2018, Intl J Molc Sci vol. 19, pp. 1-8.

* cited by examiner

*Primary Examiner* — Marianne P Allen
(74) *Attorney, Agent, or Firm* — HelixIP LLP

(57) ABSTRACT

The present disclosure provides chimeric, humanized and human monoclonal antibodies (mAbs) and fragments thereof that specifically bind to marinobufagenin (MBG) with high affinity. The anti-MBG mAbs and fragments thereof can be used to treat MBG-associated disorders, including hypertensive disorders and fibrotic disorders, optionally in combination with an additional therapeutic agent. Furthermore, the anti-MBG mAbs and fragments thereof can be used for diagnostic purposes, including to detect MBG in biological samples and to diagnose MBG-associated disorders.

17 Claims, 7 Drawing Sheets

Specification includes a Sequence Listing.

ANTI-MARINOBUFAGENIN ANTIBODIES AND USES THEREOF

STATEMENT AS TO FEDERALLY SPONSORED RESEARCH

This invention was made with government support under Grant No. 1R43HD072745-01 awarded by the government agency NIH/NICHD (National Institute of Child Health and Development). The government has certain rights in the invention.

REFERENCE TO SEQUENCE LISTING, TABLE OR COMPUTER PROGRAM

The official copy of the Sequence Listing is submitted concurrently with the specification as an ASCII formatted text file via EFS-Web, with a file name of "PRI002 ST25.txt", a creation date of Jun. 7, 2018, and a size of 52 kilobytes. The Sequence Listing filed via EFS-Web is part of the specification and is incorporated in its entirety by reference herein.

BACKGROUND OF THE DISCLOSURE

Hypertension is associated with a wide range of disorders. One hypertensive disorder is pre-eclampsia (PE). PE is a serious complication of pregnancy characterized by high blood pressure (diastolic ≥90 mmHg) and proteinuria (≥300 mg in 24 hr) after 20 weeks of gestation. PE is sometimes or often accompanied by edema (e.g., pulmonary edema), encephalopathy, seizures, renal insufficiency, liver failure, intrauterine growth restriction (IUGR), and premature birth, the latter two prejudicing the survival and well-being of the fetus and neonate. PE occurs in about 5-10% of pregnancies, and is a major cause of maternal and fetal morbidity and mortality worldwide. The only known effective therapy for PE is early delivery of the newborn.

In addition, fibrosis contributes to many disorders. One fibrotic disorder is diabetic nephropathy (DN), which is also characterized by high blood pressure. DN affects about 15-25% of type 1 diabetes patients and about 30-40% of type 2 diabetes patients, and is the most common cause of end-stage renal disease (ESRD) in the world. Clinical DN involves a series of pathological events, including initial increases in intraglomerular capillary pressure and glomerular filtration rate (GFR), glomerular hypertrophy, mesangial matrix expansion, thickening of the glomerular basement membrane, arteriolar hyalinosis, nodular glomerulosclerosis, tubulointerstitial fibrosis and injury, and proteinuria (including albuminuria). For instance, scarring of glomerular capillaries (glomerulosclerosis) impairs the filtering process of the renal corpuscle and allows proteins to leak from the blood into the urine, resulting in proteinuria. Poor glycemic control in DN patients exacerbates the disease progression to renal insufficiency and decline in GFR that can lead to ESRD.

SUMMARY OF THE DISCLOSURE

The present disclosure provides antibodies, including fragments thereof that specifically bind to marinobufagenin (MBG) with high affinity. The antibodies can be monoclonal, and can be human, chimeric or humanized antibodies. Chimeric anti-MBG antibodies including fragments thereof may have non-human (e.g., murine) complementarity-determining regions (CDRs) and non-human framework region(s), and optionally one or more human constant domains. Humanized anti-MBG antibodies including fragments thereof may have non-human (e.g., murine) CDRs and human framework region(s), and optionally non-human framework amino acid residues adjacent to CDRs and optionally one or more human constant domains. Human anti-MBG antibodies and fragments thereof may have human CDRs and human framework region(s), and optionally one or more human constant domains.

The human antibodies disclosed represent the anti-marinobufagenin antibodies from a library representing the naïve, human genomic repertoire of antibodies that bind to marinobufagenin. Panning on a human phagemid library (representing the naïve, human genomic repertoire of antibodies) identified several dozen MBG-specific clones. Subsequent characterization of >100 human antibodies (Fab) reduced the human antibodies to 14 unique antibodies that were shown to bind MBG in a competitive ELISA screen. Thus, the human antibodies obtained from the library represent those antibodies found in a naïve, human genomic library that can bind marinobufagenin.

The anti-MBG antibodies described herein may include modifications that provide a desired property to the antibody. For example, modifications can increase the serum half-life of the antibody, or the modification can decrease serum half-life. The modification can also increase the effector function of the antibody, e.g., increase clearance of antibody-MBG complexes. The modification could decrease immunogenicity, or reduce other unwanted side effects or adverse events caused by the anti-MBG antibodies.

The anti-MBG antibodies described herein can neutralize or inhibit the biological actions and effects of MBG, and thus can be used to treat MBG-associated disorders. For example, the anti-MBG antibodies described herein can be used to inhibit receptor binding by MBG on a cell. The antibodies described herein can be used to inhibit nuclear translocation of PKC-δ induced in a cell by marinobufagenin. The antibodies described herein can be used to reduce the inhibition of proliferation by endothelial cells caused by marinobufagenin. The antibodies described herein can be used to reduce the inhibition of angiogenesis by endothelial cells caused by marinobufagenin. MBG-associated disorders can include, for example, acute respiratory distress syndrome, and/or traumatic brain injury. Other MBG-associated disorders include, for example, hypertension (e.g., essential hypertension), hypertension-associated disorders (e.g., pre-eclampsia), and fibrosis-associated disorders (e.g., nonalcoholic steatohepatitis, diabetic nephropathy). These MBG-associated disorders can be treated by administering one or more of the antibodies described herein to a subject suffering from the MBG-associated disorder.

The anti-MBG antibodies described herein can be used for diagnostic purposes. Such MBG diagnostics use the antibody to detect MBG. These diagnostics can be performed in vitro or in vivo. Such diagnostics can, for example, quantitate the MBG in a sample or detect the location of MBG and/or the concentration of MBG at that location. These diagnostics can be used to determine whether a subject is suffering from an MBG-associated disorder, and optionally, the degree of severity of the MBG-associated disorder.

BRIEF DESCRIPTION OF THE DRAWINGS

A better understanding of features and advantages of the present disclosure will be obtained by reference to the following detailed description, which sets forth illustrative embodiments of the disclosure, and the accompanying drawings.

FIG. 1a compares the 6 humanized anti-MBG antibodies whereas FIG. 1b compares the humanized anti-MBG and the parent 3E9 antibody.

DETAILED DESCRIPTION OF THE DISCLOSURE

Figure 1A:
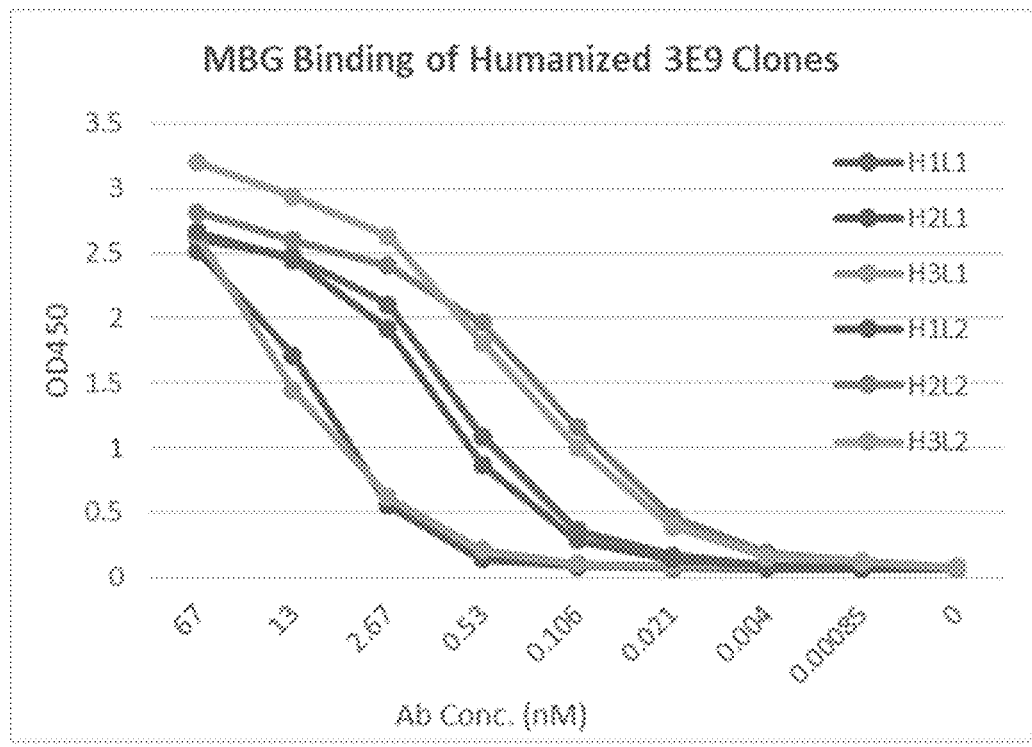
FIG. 1a and FIG. 1b show the antigen binding of humanized anti-MBG in a direct ELISA binding experiment.

While various embodiments of the present disclosure are described herein, it will be obvious to those skilled in the art that such embodiments are provided by way of example only. Numerous modifications and changes to, and variations and substitutions of, the embodiments described herein will be apparent to those skilled in the art without departing from the disclosure. It is understood that various alternatives to the embodiments described herein can be employed in practicing the disclosure. It is also understood that every embodiment of the disclosure can optionally be combined with any one or more of the other embodiments described herein which are consistent with that embodiment.

Where elements are presented in list format (e.g., in a Markush group), it is understood that each possible subgroup of the elements is also disclosed, and any one or more elements can be removed from the list or group.

It is also understood that, unless clearly indicated to the contrary, in any method described or claimed herein that includes more than one act or step, the order of the acts or steps of the method is not necessarily limited to the order in which the acts or steps of the method are recited, but the disclosure encompasses embodiments in which the order is so limited.

It is further understood that, in general, where an embodiment in the description or the claims is referred to as comprising one or more features, the disclosure also encompasses embodiments that consist of, or consist essentially of, such feature(s).

It is also understood that any embodiment of the disclosure, e.g., any embodiment found within the prior art, can be explicitly excluded from the claims, regardless of whether or not the specific exclusion is recited in the specification.

It is further understood that reference to a peptide, a polypeptide or a protein herein, such as an antibody or a fragment thereof, includes pharmaceutically acceptable salts thereof unless specifically stated otherwise or the context clearly indicates otherwise. Such salts can have a positive net charge, a negative net charge or no net charge.

Headings are included herein for reference and to aid in locating certain sections. Headings are not intended to limit the scope of the embodiments and concepts described in the sections under those headings, and those embodiments and concepts may have applicability in other sections throughout the entire disclosure.

All patent literature and all non-patent literature cited herein are incorporated herein by reference in their entirety to the same extent as if each patent literature or non-patent literature were specifically and individually indicated to be incorporated herein by reference in its entirety.

I. Definitions

Unless defined otherwise or clearly indicated otherwise by their use herein, all technical and scientific terms used herein have the same meaning as commonly understood by those of ordinary skill in the art to which this application belongs.

As used in the specification and the appended claims, the indefinite articles "a" and "an" and the definite article "the" can include plural referents as well as singular referents unless specifically stated otherwise or the context clearly indicates otherwise.

The term "about" or "approximately" means an acceptable error for a particular value as determined by one of ordinary skill in the art, which depends in part on how the value is measured or determined. In certain embodiments, the term "about" or "approximately" means within one standard deviation. In some embodiments, when no particular margin of error (e.g., a standard deviation to a mean value given in a chart or table of data) is recited, the term "about" or "approximately" means that range which would encompass the recited value and the range which would be included by rounding up or down to the recited value as well, taking into account significant figures. In certain embodiments, the term "about" or "approximately" means within ±10%, 5%, 4%, 3%, 2% or 1% of the specified value. Whenever the term "about" or "approximately" precedes the first numerical value in a series of two or more numerical values or in a series of two or more ranges of numerical values, the term "about" or "approximately" applies to each one of the numerical values in that series of numerical values or in that series of ranges of numerical values.

The term "antibody" refers to a protein functionally defined as a binding protein and structurally defined as comprising an amino acid sequence that is recognized as being derived from the framework region of an immunoglobulin encoding gene. An antibody can consist of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

A typical gamma immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist as intact immunoglobulins or as a number of well-characterized fragments. Thus, for example, pepsin digests an antibody below the disulfide linkages in the hinge region to produce F(ab)'$_2$, a dimer of Fab' which itself is naturally a light chain joined to VH-CH1-Hinge by a disulfide bond. The F(ab)'$_2$ may be reduced under mild conditions to break the disulfide linkage/s in the hinge region thereby converting the (Fab')$_2$ dimer into an Fab' monomer. The Fab' monomer is essentially a Fab with part of the hinge region (see, Fundamental Immunology, W. E. Paul, ed., Raven Press, N.Y. (1993), for a more detailed description of other antibody fragments). While various antibody fragments are defined in terms of the digestion of an intact antibody, one of skill in the art will appreciate that fragments can be synthesized de novo either chemically or by utilizing recombinant DNA methods. Thus, the term antibody, as used herein also includes antibody fragments either produced by the modification of whole antibodies or synthesized using recombinant DNA methodologies. Preferred antibodies include $V_H$—$V_L$ dimers, including single chain antibodies (antibodies that exist as a single polypeptide chain), such as single chain Fv antibodies (sFv or scFv) in which a variable heavy and a variable light region are joined together (directly or through a peptide linker) to form a continuous polypeptide. The single chain Fv antibody is a covalently linked $V_H$-$V_L$ heterodimer which may be expressed from a nucleic acid including $V_H$- and $V_L$-encoding sequences either joined directly or joined by a peptide-encoding linker (e.g., Huston, et al. Proc. Nat. Acad. Sci. USA, 85:5879-5883, 1988, which is hereby incorporated by reference in its entirety). While the $V_H$ and $V_L$ are connected to each as a single polypeptide chain, the $V_H$ and $V_L$ domains associate non-covalently. Alternatively, the antibody can be another fragment. Other fragments can also be generated, including using recombinant techniques. For example Fab molecules can be displayed on phage if one of the chains (heavy or light) is fused to g3 capsid protein and the complementary chain exported to the periplasm as a soluble molecule. The two chains can be encoded on the same or on different replicons; the two antibody chains in each Fab molecule assemble post-translationally and the dimer is incorporated into the phage particle via linkage to one of the chains of g3p (see, e.g., U.S. Pat. No. 5,733,743, which is hereby incorporated by reference in its entirety). The scFv antibodies and a number of other structures converting the naturally aggregated, but chemically separated light and heavy polypeptide chains from an antibody V region into a molecule that folds into a three dimensional structure substantially similar to the structure of an antigen-binding site are known to those of skill in the art (see e.g., U.S. Pat. Nos. 5,091,513, 5,132,405, and 4,956,778, all of which are hereby incorporated by reference in their entirety). Particularly preferred antibodies include all those that have been displayed on phage or generated by recombinant technology using vectors where the chains are secreted as soluble proteins, e.g., scFv, Fv, Fab, (Fab')$_2$. Antibodies can also include diabodies and minibodies.

Antibodies also include heavy chain dimers, such as antibodies from camelids. Since the $V_H$ region of a heavy chain dimer IgG in a camelid does not have to make hydrophobic interactions with a light chain, the region in the heavy chain that normally contacts a light chain is changed to hydrophilic amino acid residues in a camelid. $V_H$ domains of heavy-chain dimer IgGs are called $V_{HH}$ domains.

In camelids, the diversity of antibody repertoire is determined by the complementary determining regions (CDR) 1, 2, and 3 in the $V_H$ or $V_{HH}$ regions. The CDR3 in the camel $V_{HH}$ region is characterized by its relatively long length averaging 16 amino acids (Muyldermans et al., 1994, Protein Engineering 7(9): 1129, which is hereby incorporated by reference in its entirety). This is in contrast to CDR3 regions of antibodies of many other species. For example, the CDR3 of mouse $V_H$ has an average of 9 amino acids.

Libraries of camelid-derived antibody variable regions, which maintain the in vivo diversity of the variable regions of a camelid, can be made by, for example, the methods disclosed in U.S. Patent Application publication No. US20050037421, published Feb. 17, 2005, which is hereby incorporated by reference in its entirety.

Antibody-dependent cell-mediated cytotoxicity (ADCC) is an important mechanism of action of antibodies. ADCC may be enhanced by several methods, many of which involve an end product antibody with improved Fc-receptor binding. Amino acid substitutions in the antibody Fc region have been shown to increase Fc binding affinity for FcγRIIIa receptor on NK cells (Natsume et al., Drug Design, Development and Therapy, 2009, vol. 3, pp. 7-16, which is hereby incorporated by reference in its entirety) and to improve ADCC activity. Another method for improving ADCC is to change the sugar composition of the antibody glycosylation. This is done by making antibodies that lack fucose residues, which is to say, an 'a-fucosylated' or 'de-fucosylated' antibody. One method involves changing/modifying the glycosylation site of the antibody so that fucose cannot be added to the antibody (U.S. Pat. No. 6,194,551, Feb. 27, 2001). Another method is to remove a pre-existing fucose on an antibody by, for example, enzymatic degradation or removal of the fucose by any other means. Another method involves the genetic engineering of the host expression system so that fucose cannot be transferred to or added to the antibody, for example by suppression or deletion of fucosyl transferase activity (U.S. Patent Application publication Nos.: 20070134759. Jun. 14, 2007; and 20080166756, Jul. 10, 2008, both of which are hereby incorporated by reference in their entirety).

As used herein, the term "antigen" refers to substances that are capable, under appropriate conditions, of inducing a specific immune response and of reacting with the products of that response, such as, with specific antibodies or specifically sensitized T-lymphocytes, or both. Antigens may be soluble substances, such as toxins and foreign proteins, or particulates, such as bacteria and tissue cells; however, only the portion of the protein or polysaccharide molecule known as the antigenic determinant (epitopes) combines with the antibody or a specific receptor on a lymphocyte. More broadly, the term "antigen" may be used to refer to any substance to which an antibody binds, or for which antibodies are desired, regardless of whether the substance is immunogenic. For such antigens, antibodies may be identified by recombinant methods, independently of any immune response.

As used herein, the term "binding specificity" of an antibody refers to the identity of the antigen to which the antibody binds, preferably to the identity of the epitope to which the antibody binds.

As used herein, the term "chimeric polynucleotide" means that the polynucleotide comprises regions which are wild-type and regions which are mutated. It may also mean that the polynucleotide comprises wild-type regions from one polynucleotide and wild-type regions from another related polynucleotide.

As used herein, the term "complementarity-determining region" or "CDR" refer to the art-recognized term as exemplified by Kabat and Chothia. CDRs are also generally known as hypervariable regions or hypervariable loops (Chothia and Lesk (1987) J Mol. Biol. 196: 901; Chothia et al. (1989) Nature 342: 877; E. A. Kabat et al., Sequences of Proteins of Immunological Interest (National Institutes of Health, Bethesda, Md.) (1987); and Tramontano et al. (1990) J Mol. Biol. 215: 175, all of which are hereby incorporated by reference in their entirety). "Framework region" or "FR" refers to the region of the V domain that flank the CDRs. The positions of the CDRs and framework regions can be determined using various well known definitions in the art, e.g., Kabat, Chothia, international ImMunoGeneTics database (IMGT), and AbM (see, e.g., Johnson et al., supra; Chothia & Lesk, 1987, Canonical structures for the hypervariable regions of immunoglobulins. J. Mol. Biol. 196, 901-917; Chothia C. et al., 1989, Conformations of immunoglobulin hypervariable regions. Nature 342, 877-883; Chothia C. et al., 1992, structural repertoire of the human VH segments J. Mol. Biol. 227, 799-817; Al-Lazikani et al., J. Mol. Biol 1997, 273(4)). Definitions of antigen combining sites are also described in the following: Ruiz et al., IMGT, the international ImMunoGeneTics database. Nucleic Acids Res., 28, 219-221 (2000); and Lefranc, M.-P. IMGT, the international ImMunoGeneTics database. Nucleic Acids Res. January 1; 29(1):207-9 (2001); MacCallum et al, Antibody-antigen interactions: Contact analysis and binding site topography, J. Mol. Biol., 262 (5), 732-745 (1996); and Martin et al, Proc. Natl Acad. Sci. USA, 86, 9268-9272 (1989); Martin, et al, Methods Enzymol., 203, 121-153, (1991); Pedersen et al, Immunomethods, 1, 126, (1992); and Rees et al, In Sternberg M. J. E. (ed.), Protein Structure Prediction. Oxford University Press, Oxford, 141-172 1996, all of which are hereby incorporated by reference in their entirety).

Whenever the term "at least" or "greater than" precedes the first numerical value in a series of two or more numerical values, the term "at least" or "greater than" applies to each one of the numerical values in that series of numerical values.

The term "heterologous" refers to an amino acid or nucleotide sequence that is not naturally found in association with the amino acid or nucleotide sequence with which it is associated.

The term "natural" or "naturally occurring" as applied to an object refers to the fact that the object can be found in nature. For example, a polypeptide or polynucleotide sequence which is present in an organism (including viruses) and can be isolated from a source in nature, and which has not been intentionally modified by man in the laboratory, is naturally occurring.

Whenever the term "no more than" or "less than" precedes the first numerical value in a series of two or more numerical values, the term "no more than" or "less than" applies to each one of the numerical values in that series of numerical values.

The term "polynucleotide" refers to a polymer composed of nucleotide units. Polynucleotides include naturally occurring nucleic acids, such as deoxyribonucleic acid ("DNA") and ribonucleic acid ("RNA"), as well as nucleic acid analogs. Nucleic acid analogs include those which contain non-naturally occurring bases, nucleotides that engage in linkages with other nucleotides other than the naturally occurring phosphodiester bond, or/and bases attached through linkages other than phosphodiester bonds. Non-limiting examples of nucleotide analogs include phosphorothioates, phosphorodithioates, phosphorotriesters, phosphoramidates, boranophosphates, methylphosphonates, chiral-methyl phosphonates, 2-O-methyl ribonucleotides, peptide-nucleic acids (PNAs), and the like. Such polynucleotides can be synthesized, e.g., using an automated DNA synthesizer. The term "nucleic acid molecule" typically refers to larger polynucleotides. The term "oligonucleotide" typically refers to shorter polynucleotides. In certain embodiments, an oligonucleotide contains no more than about 50 nucleotides. It is understood that when a nucleotide sequence is represented by a DNA sequence (i.e., A, T, G, C), this also includes an RNA sequence (i.e., A, U, G, C) in which "U" replaces "T".

The term "polypeptide" refers to a polymer composed of natural or/and unnatural amino acid residues, naturally occurring structural variants thereof, or/and synthetic non-naturally occurring analogs thereof, linked via peptide bonds. Synthetic polypeptides can be synthesized, e.g., using an automated polypeptide synthesizer. Polypeptides can also be produced recombinantly in cells expressing nucleic acid sequences that encode the polypeptides. The term "protein" typically refers to larger polypeptides. The term "peptide" typically refers to shorter polypeptides. In certain embodiments, a peptide contains no more than about 50, 40 or 30 amino acid residues. Polypeptides include antibodies and fragments thereof. Conventional notation is used herein to portray polypeptide sequences: the left-hand end of a polypeptide sequence is the amino (N)-terminus; the right-hand end of a polypeptide sequence is the carboxyl (C)-terminus.

Polypeptides can include one or more modifications that may be made during the course of synthetic or cellular production of the polypeptide, such as one or more post-translational modifications, whether or not the one or more modifications are deliberate. Modifications can include without limitation glycosylation (e.g., N-linked glycosylation and O-linked glycosylation), lipidation, phosphorylation, sulfation, acetylation (e.g., acetylation of the N-terminus), amidation (e.g., amidation of the C-terminus), hydroxylation, methylation, formation of an intramolecular or intermolecular disulfide bond, formation of a lactam between two side chains, formation of pyroglutamate, and ubiquitination. As another example, a polypeptide can be attached to a natural polymer (e.g., a polysaccharide) or a synthetic polymer (e.g., polyethylene glycol [PEG]), lipidated (e.g., acylated with a $C_8$-$C_{20}$ acyl group), or labeled with a detectable agent (e.g., a radionuclide, a fluorescent dye or an enzyme). PEGylation can increase the protease resistance, stability and half-life, increase the solubility and reduce the aggregation of the polypeptide.

The term "conservative substitution" refers to substitution of an amino acid in a polypeptide with a functionally, structurally or chemically similar natural or unnatural amino acid. In certain embodiments, the following groups each contain natural amino acids that are conservative substitutions for one another:
  1) Glycine (Gly/G), Alanine (Ala/A);
  2) Isoleucine (Ile/I), Leucine (Leu/L), Methionine (Met/M), Valine (Val/V);
  3) Phenylalanine (Phe/F), Tyrosine (Tyr/Y), Tryptophan (Trp/W);
  4) Serine (Ser/S), Threonine (Thr/T), Cysteine (Cys/C);
  5) Asparagine (Asn/N), Glutamine (Gln/Q);
  6) Aspartic acid (Asp/D), Glutamic acid (Glu/E); and
  7) Arginine (Arg/R), Lysine (Lys/K), Histidine (His/H).

In further embodiments, the following groups each contain natural amino acids that are conservative substitutions for one another:
1) non-polar: Ala, Val, Leu, Ile, Met, Pro (proline/P), Phe, Trp;
2) hydrophobic: Val, Leu, Ile, Phe, Tyr, Trp;
3) aliphatic: Ala, Val, Leu, Ile;
4) aromatic: Phe, Tyr, Trp, His;
5) uncharged polar or hydrophilic: Gly, Ala, Pro, Ser, Thr, Cys, Asn, Gln, Tyr (tyrosine may be regarded as a hydrophobic amino acid with a polar side group);
6) aliphatic hydroxyl- or sulfhydryl-containing: Ser, Thr, Cys;
7) amide-containing: Asn, Gln;
8) acidic: Asp, Glu;
9) basic: Lys, Arg, His; and
10) small: Gly, Ala, Ser, Cys.

In other embodiments, amino acids may be grouped as set out below:
1) hydrophobic: Val, Leu, Ile, Met, Phe, Trp, Tyr;
2) aromatic: Phe, Tyr, Trp, His;
3) neutral hydrophilic: Gly, Ala, Pro, Ser, Thr, Cys, Asn, Gln;
4) acidic: Asp, Glu;
5) basic: Lys, Arg, His; and
6) residues that influence backbone orientation: Pro, Gly.

A polypeptide having one or more modifications relative to a parent polypeptide may be called an "analog", "derivative" or "variant" of the parent polypeptide as appropriate.

The disclosure encompasses pharmaceutically acceptable salts of polypeptides, including those with a positive net charge, those with a negative net charge, and those with no net charge.

The term "pharmaceutically acceptable" refers to a substance (e.g., an active ingredient or an excipient) that is suitable for use in contact with the tissues and organs of a subject without excessive irritation, allergic response, immunogenicity and toxicity, is commensurate with a reasonable benefit/risk ratio, and is effective for its intended use. A "pharmaceutically acceptable" excipient or carrier of a pharmaceutical composition is also compatible with the other ingredients of the composition.

The term "stringent hybridization conditions" refers to hybridizing in 50% formamide at 5×SSC at a temperature of 42° C. and washing the filters in 0.2×SSC at 60° C. (1×SSC is 0.15M NaCl, 0.015M sodium citrate.) Stringent hybridization conditions also encompasses low ionic strength and high temperature for washing, for example 0.015 M sodium chloride/0.0015 M sodium citrate/0.1% sodium dodecyl sulfate at 50° C.; hybridization with a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or 50% formamide, 5XSSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

The term "subject" refers to an animal, including but not limited to a mammal, such as a primate (e.g., a human, a chimpanzee or a monkey), a rodent (e.g., a rat, a mouse, a guinea pig, a gerbil or a hamster), a lagomorph (e.g., a rabbit), a swine (e.g., a pig), an equine (e.g., a horse), a canine (e.g., a dog) or a feline (e.g., a cat).

The term "substantially homologous" or "substantially identical" in the context of two polypeptides or polynucleotides refers to two or more sequences or subsequences that have at least about 50%, 60%, 65%, 70%, 75%, 80%, 85%, 90%, 95%, 96%, 97%, 98% or 99% amino acid or nucleic acid residue identity, when compared and aligned for maximum correspondence, as measured using a sequence comparison algorithm or by visual inspection. The terms "substantially homologous" or "substantially identical" can mean at least about 70% amino acid or nucleic acid residue identity. The term "substantially homologous" or "substantially identical" can mean at least about 85% amino acid or nucleic acid residue identity. The substantial homology or identity can exist over a region of the sequences that is at least about 20, 30, 40, 50, 100, 150 or 200 residues in length. The sequences can be substantially homologous or identical over the entire length of either or both comparison biopolymers.

Optimal alignment of sequences for comparison can be conducted, e.g., by the local homology algorithm of Smith and Waterman, *Adv. Appl. Math.*, 2:482 (1981); by the homology alignment algorithm of Needleman and Wunsch, *J. Mol. Biol.*, 48:443 (1970); by the search for similarity method of Pearson and Lipman, *Proc. Natl. Acad. Sci. USA*, 85:2444 (1988); by computerized implementations of these algorithms (e.g., GAP, BESTFIT, FASTA, and TFASTA in the Wisconsin Genetics Software Package, Genetics Computer Group, Madison, Wis.); or by visual inspection.

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng and Doolittle, *J. Mol. Evol.*, 35:351-360 (1987). The method used is similar to the method described by Higgins and Sharp, *CABIOS*, 5:151-153 (1989). The program can align up to about 300 sequences, each having a maximum length of about 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps. Another algorithm that is useful for generating multiple alignments of sequences is Clustal W (see, e.g., Thompson et al., *Nucleic Acids Research*, 22:4673-4680 [1994]).

Another example of an algorithm that is suitable for determining percent sequence identity and sequence similarity is the BLAST algorithm, which is described in Altschul et al., *J. Mol. Biol.*, 215:403-410 (1990). Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul 1990). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction is halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults, e.g., a wordlength (W) of 11, an expectation (E) of 10, M=5, N=−4, and a comparison of both strands. For amino acid sequences, the BLASTP program uses as defaults, e.g., a wordlength (W) of 3, an expectation (E) of 10, and the BLOSUM62 scoring matrix (see Henikoff and Henikoff, *Proc. Natl. Acad. Sci. USA,* 89:10915 [1989]).

In addition to calculating percent sequence identity, the BLAST algorithm also performs a statistical analysis of the similarity between two sequences (see, e.g., Karlin and Altschul, *Proc. Natl. Acad. Sci. USA,* 90:5873-5787 [1993]). One measure of similarity provided by the BLAST algorithm is the smallest sum probability [P(N)], which provides an indication of the probability by which a match between two nucleotide or amino acid sequences would occur by chance. In certain embodiments, a polynucleotide is considered similar to a reference sequence if the smallest sum probability in a comparison of the test polynucleotide to the reference polynucleotide is less than about 0.1, 0.01 or 0.001.

In some embodiments, a polypeptide is substantially homologous or identical to a second polypeptide if the two polypeptides differ only by conservative amino acid substitutions. In certain embodiments, two nucleic acid sequences are substantially homologous or identical if the two polynucleotides hybridize to each other under stringent conditions, or under highly stringent conditions, as described herein.

The term "therapeutically effective amount" refers to an amount of a compound that, when administered to a subject, is sufficient to prevent, reduce the risk of developing, delay the onset of, slow the progression or cause regression of the medical condition being treated, or to alleviate to some extent the medical condition or one or more symptoms or complications of that condition. The term "therapeutically effective amount" also refers to an amount of a compound that is sufficient to elicit the biological or medical response of a cell, tissue, organ, system, animal or human which is sought by a researcher, veterinarian, medical doctor or clinician.

The terms "treat", "treating" and "treatment" include alleviating, ameliorating or abrogating a medical condition or one or more symptoms or complications associated with the condition, and alleviating, ameliorating or eradicating one or more causes of the condition. Reference to "treatment" of a medical condition includes prevention of the condition. The terms "prevent", "preventing" and "prevention" include precluding, reducing the risk of developing and delaying the onset of a medical condition or one or more symptoms or complications associated with the condition.

II. Anti-Marinobufagenin Antibodies

Antibodies described herein have specificity for marinobufagenin (MBG) and include all the forms described above. The antibody can be engineered for use in a particular organism. The organism can be a human, canine, or a commercially valuable livestock, such as, for example, pigs, horses, dogs, cats, chickens, or other birds. Such engineering of the antibody includes, for example, humanization, humaneering, chimerization, or isolating human (or other organism) antibodies using any of the repertoire technologies or monoclonal technologies known in the art.

Affinity maturation can be used with an antibody disclosed herein to obtain an anti-MBG antibody of a desired affinity. When an anti-MBG antibody is obtained from an animal (e.g., a transgenic animal carrying a human antibody repertoire), the antibodies made in the transgenic animal can undergo affinity maturation. Alternatively, antibodies from a transgenic animal, or from other technologies (such as a display technology) can be affinity matured using chain shuffling approaches and/or mutation of the nucleic acids encoding VH and VL followed by screening and/or selecting for antibodies with greater affinity.

The most widely used methods for minimizing the immunogenicity of non-human antibodies while retaining specificity and affinity involve grafting the CDRs of the non-human antibody onto human frameworks typically selected for their structural homology to the non-human framework (Jones et al., 1986, Nature 321:522-5; U.S. Pat. No. 5,225,539, both of which are hereby incorporated by reference in their entirety). Originally these methods resulted in drastic losses of affinity. However, it was then shown that some of the affinity could be recovered by restoring the non-human residues at key positions in the framework that are required to maintain the canonical structures of the non-human CDRs 1 and 2 (Bajorath et al., 1995, J Biol Chem 270:22081-4; Martin et al., 1991, Methods Enzymol. 203:121-53; Al-Lazikani, 1997, J Mol Biol 273:927-48, all of which are hereby incorporated by reference in their entirety). Recovering the native conformations of CDR3s is a much more uncertain enterprise because their structures are more variable.

Improvements to the traditional CDR-grafting approaches use various hybrid selection approaches, in which portions of the non-human antibody have been combined with libraries of complementary human antibody sequences in successive rounds of selection for antigen binding, in the course of which most of the non-human sequences are gradually replaced with human sequences. Other methodologies include chain replacement techniques where the non-human CDR3s were retained and only the remainder of the V-regions, including the frameworks and CDRs 1 and 2, were individually replaced in steps performed.

These technologies can be used to make antibodies suitable for use in non-human subjects by engineering the CDRs into framework regions of the subject species using analogous approaches to the CDR grafting methods used for make antibodies for use in humans.

Chimeric anti-MBG antibodies can be made using a starting anti-MBG antibody and grafting the variable region of the starting anti-MBG antibody onto a desired variable domain constant region. Chimeric antibodies were made, for example, by combining mouse VL and VH regions with human constant regions CL (light chain constant region) and at least CH1 (heavy chain constant region 1). The VH region used in the chimeric antibodies was:

(SEQ ID NO: 1)
EVQLQESGPSLVKPSQTLSLTCSVTGDSITSGYWNWIRKFPGNKLEYNIG

YISYSGTTYYNPSLKSRISITRDTSKNQYYLQLNSVTTEDTATYYCARAR

YGYGFDYWGQGTTLTVSS

The VL region used in the chimeric antibodies was:

(SEQ ID NO: 2)
DVLMTQTPLSLPVSLGDQASISCRSSQSIVHSNRNTYLEWYLQKPGQSPK

LLIYKVSNRFSGVPDRFSGSGSGTDFTLKISRVEAEDLGVYYCFQGSHVP

LTFGAGTKLELK

Anti-MBG, humanized antibodies were made, for example, using the CDRs:

```
VH CDR1:
                                            (SEQ ID NO: 3)
DSITSGYWN

VH CDR2:
                                            (SEQ ID NO: 4)
YISYSGTTYYNPSLKS

VH CDR3:
                                            (SEQ ID NO: 5)
ARYGYGFDY

V_L CDR1:
                                            (SEQ ID NO: 6)
RSSQSIVHSNRNTYLE

V_L CDR2:
                                            (SEQ ID NO: 7)
KVSNRFS

V_L CDR3:
                                            (SEQ ID NO: 8)
FQGSHVPLT
```

The three VH CDRs were placed into the framework sequences of a human variable region for a heavy chain to produce the VH chain:

(SEQ ID NO: 9)
QVQLQESGPGLVKPSETLSLTCTVSGDSITSGYWNWIRQPPGKGLEWIGY

ISYSGTTYYNPSLKSRVTISVDTSKNQFSLKLSSVTAADTAVYYCARARY

GYGFDYWGQGTLVTVSS

This VH was designated H1. Substitutions were introduced into the framework regions of the SEQ ID NO: 9 to make two additional VH chains:

(SEQ ID NO: 10)
EVQLQESGPGLVKPSETLSLTCTVSGDSITSGYWNWIRQPPGKGLEYIGY

ISYSGTTYYNPSLKSRVTISRDTSKNQFSLKLSSVTAADTAVYYCARARY

GYGFDYWGQGTLVTVSS (SEQ ID NO: 11)
EVQLQESGPGLVKPSETLSLTCTVSGDSITSGYWNWIRQPPGKGLEYMGY

ISYSGTTYYNPSLKSRITISRDTSKNQYSLKLSSVTAADTAVYYCARARY

GYGFDYWGQGTLVTVSS

SEQ ID NO: 10 was designated H2 and SEQ ID NO: 11 was designated H3.

The three VL CDRs were placed into the framework sequences for a human variable region from a light chain to produce the VL chain:

(SEQ ID NO: 12)
DVVMTQSPLSLPVTLGQPASISCRSSQSIVHSNRNTYLEWFQQRPGQSPR

RLIYKVSNRFSGVPDRFSGSGSGTDFTLKISRVEAEDVGVYYCFQGSHVP

LTFGGGTKVEIK

SEQ ID NO: 12 was designated L1. Substitutions were introduced into the framework regions of SEQ ID NO: 12 to make an additional VL chain:

(SEQ ID NO: 13)
DVVMTQSPLSLPVTLGQPASISCRSSQSIVHSNRNTYLEWYQQRPGQSPR

LLIYKVSNRFSGVPDRFSGSGSGTDFTLKISRVEAEDVGVYYCFQGSHVP

LTFGGGTKVEIK

SEQ ID NO: 13 was designated L2. The VL chain SEQ ID NO: 12 was combined with each of the HL chains (SEQ ID NOs: 9, 10, and 11) to make three different antibodies (H1L1, H2L1, and H3L1). The VL chain SEQ ID NO: 13 was also combined with each of the HL chains (SEQ ID NOs: 9, 10, and 11) to make three different antibodies (H1L2, H2L2, and H3L2).

Human, anti-MBG antibodies were obtained from the human display library. Fourteen anti-MBG antibodies were obtained, and the sequence of these fourteen human antibody heavy and light chains are as follows. The human antibody designated as 236/237 had VH and VL sequences:

236/237 VH
(SEQ ID NO: 14)
QVQLQESGPGLVKPSETLSLTCTVSGGSISSSSYYWGWIRQPPGKGLEWI

GSIYYSGSTYYNPSLKSRVTISVDTSKNQFSLKLSSVTAADTAVYYCARA

RYNWNYVLFDYWGQGTLV

TVSS

236/237 VL
(SEQ ID NO: 15)
QAVLTQPSSVSAAPRQRVTISCSGSASNIGRNGVSWYHQVPGKAPRLLLS

HDGLVTSGVPDRLSVSKSGTSASLAISGLHSDDEGDYYCAVWDDSLNAVV

FGGGTKLTVLS

The VH CDR sequences for 236/237 VH are:

```
        236/237 VH CDR1
                                            (SEQ ID NO: 16)
        GGSISSSSYY

236/237 VH CDR2
                                            (SEQ ID NO: 17)
        IYYSGST
```

```
236/237 VH CDR3
                                   (SEQ ID NO: 18)
ARARYNWNYVLFDY
```

The VL CDR sequences for 236/237 VL are

```
236/237 VL CDR1
                                   (SEQ ID NO: 19)
ASNIGRNG

236/237 VL CDR2
                                   (SEQ ID NO: 20)
HDG

236/237 VL CDR3
                                   (SEQ ID NO: 21)
AVWDDSLNAVV
```

The human antibody designated as 201/202 had VH and VL sequences:

```
201/202 VH
                                   (SEQ ID NO: 22)
QLQLQESGPGLVKPSQTLSLTCTVSGGSISSGGYYWGWIRQPPGKGLEWI
GSIYYSGNTYYNPSLKSRVTISVDTSKNQFSLKLSSVTAADTAVYYCARA
SIAARTFDYWGQGTLVTVSS

201/202 VL
                                   (SEQ ID NO: 23)
QSVLTQPPSVSAAPGQKVTISCSGSSSNIGNNYVSWYQQLPGTAPKLLIY
DNNKRPSGIPDRFSGSKSGTSATLGITGLQTGDEADYYCGTWDSSLSAYV
FGTGTKVTVL
```

The VH CDR sequences for 201/202 VH are:

```
201/202 VH CDR1
                                   (SEQ ID NO: 24)
GGSISSGGYY

201/202 VH CDR2
                                   (SEQ ID NO: 25)
IYYSGNT

201/202 VH CDR3
                                   (SEQ ID NO: 26)
ARASIAARTFDY
```

The VL CDR sequences for 201/202 VL are

```
201/202 VL CDR1
                                   (SEQ ID NO: 27)
SSNIGNNY

201/202 VL CDR2
                                   (SEQ ID NO: 28)
DNN

201/202 VL CDR3
                                   (SEQ ID NO: 29)
GTWDSSLSAYV
```

The human antibody designated as 203/204 had VH and VL sequences:

```
203/204 VH
                                   (SEQ ID NO: 30)
QLQLQESGPGLVKPSETLSLTCTVSGGSISSYYWGWIRQPPGKGLEWIGS
IYYSGSTYYNPSLKSRVTISVDTSKNQFSLQLKSVTPEDTAVYYCARVRP
PAATFDYWGQGTLVTVSS

203/204 VL
                                   (SEQ ID NO: 31)
QSVVTQPPSVSAAPGQKVSISCSGGSSNIGNNYVSWYQQLPGTAPRLLIY
ENNNRPSGIPDRFSGSKSGTSATLGITGLQTGDEADYYCGTWDSSLRAVV
FGGGTKLTVL
```

The VH CDR sequences for 203/204 VH are:

```
203/204 VH CDR1
                                   (SEQ ID NO: 32)
GGSISSYY

203/204 VH CDR2
                                   (SEQ ID NO: 17)
IYYSGST

203/204 VH CDR3
                                   (SEQ ID NO: 33)
ARVRPPAATFDY
```

The VL CDR sequences for 203/204 VL are

```
203/204 VL CDR1
                                   (SEQ ID NO: 27)
SSNIGNNY

203/204 VL CDR2
                                   (SEQ ID NO: 34)
ENN

203/204 VL CDR3
                                   (SEQ ID NO: 35)
GTWDSSLRAVV
```

The human antibody designated as 206/208 had VH and VL sequences:

```
206/208 VH
                                   (SEQ ID NO: 36)
QVQLQESGPGLVKPSETLSLTCTVSGGSISSSSYYWGWIRQPPGKGLEWI
GSIYYSGSTYYNPSLKSRVTISVDTSKNQFSLKLSSVTAADTAVYYCARV
NLRGAFDIWGQGTTVTVSS

206/208 VL
                                   (SEQ ID NO: 37)
QSVVTQPPSVSGAPGQRVTISCTGSSSNIGAGYDVHWYQQLPGTAPKLLI
YENNKRPSGIPDRFSGSKSGTSATLGITGLQTGDEADYYCGTWDSSLSAV
VFGGGTKLTVL
```

The VH CDR sequences for 206/208 VH are:

```
206/208 VH CDR1
                                   (SEQ ID NO: 16)
GGSISSSSYY

206/208 VH CDR2
                                   (SEQ ID NO: 17)
IYYSGST

206/208 VH CDR3
                                   (SEQ ID NO: 38)
ARVNLRGAFDI
```

The VL CDR sequences for 206/208 VL are

```
206/208 VL CDR1
                             (SEQ ID NO: 39)
SSNIGAGYD

206/208 VL CDR2
                             (SEQ ID NO: 34)
ENN

206/208 VL CDR3
                             (SEQ ID NO: 40)
GTWDSSLSAVV
```

The human antibody designated as 238/239 had VH and VL sequences:

```
238/239 VH
                             (SEQ ID NO: 41)
QLQLQESGPGLVKPSETLSLTCTVSGGSISSSSYYWGWIRQPPGKGLEWI
GSIYYSGSTYYNPSLKSRVTISVDTSKNQFSLKLSSVTAADTAVYYCARV
VVARTGTTISWFDPWGQGTLVTVSS

238/239 VL
                             (SEQ ID NO: 42)
QAVLTQPSSLSASPGASASLTCTLRSGINVDTYRIYWYQQKPGSPPQYLL
RYKSDSDKQQGSGVPSRFSGSKDASANAGILLISGLQSEDEADYYCVIWH
SSAWVFGGGTKLTVL
```

The VH CDR sequences for 238/239 VH are:

```
238/239 VH CDR1
                             (SEQ ID NO: 16)
GGSISSSSYY

238/239 VH CDR2
                             (SEQ ID NO: 17)
IYYSGST

238/239 VH CDR3
                             (SEQ ID NO: 43)
ARVVVARTGTTISWFDP
```

The VL CDR sequences for 238/239 VL are

```
238/239 VL CDR1
                             (SEQ ID NO: 44)
SGINVDTYR

238/239 VL CDR2
                             (SEQ ID NO: 45)
YKSDSDK

238/239 VL CDR3
                             (SEQ ID NO: 46)
VIWHSSAWV
```

The human antibody designated as 240/241 had VH and VL sequences:

```
240/241 VH
                             (SEQ ID NO: 47)
QVQLQESGPGLVKPSETLSLTCTVSGGSISSSSYYWGWIRQPPGKGLEWI
GSIYYSGSTYYNPSLKSRVTISVDTSKNQFSLKLSSVTAADTAVYYCARL
RYSSGWYADPWGQGTLVTVSS

240/241 VL
                             (SEQ ID NO: 48)
LPVLTQPPSASGTPGQRVTISCSGSSSNIGSNIVNWYQQLPGTAPKWYNN
NQRPSGVPDRFSGSKSGASASLAISGLQSEDEADYYCVAWDGSLSGVVFG
GGTKLTVL
```

The VH CDR sequences for 240/241 VH are:

```
240/241 VH CDR1
                             (SEQ ID NO: 16)
GGSISSSSYY

240/241 VH CDR2
                             (SEQ ID NO: 17)
IYYSGST

240/241 VH CDR3
                             (SEQ ID NO: 49)
ARLRYSSGWYADP
```

The VL CDR sequences for 240/241 VL are

```
240/241 VL CDR1
                             (SEQ ID NO: 50)
SSNIGSNI

240/241 VL CDR2
                             (SEQ ID NO: 51)
NNN

240/241 VL CDR3
                             (SEQ ID NO: 52)
VAWDGSLSGVV
```

The human antibody designated as 205/207 had VH and VL sequences:

```
205/207 VH
                             (SEQ ID NO: 53)
QLQLQESGPGLVKPSETLSLTCTVSGGSISSSSYYWGWIRQPPGKGLEWI
GSIYYSGSTYYNPSLKSRVTISVDTSKNQFSLKLSSVTAADTAVYYCARF
HTWAPRAFDIWGQGTMVTVSS

205/207 VL
                             (SEQ ID NO: 54)
QSVVTQPPSVSAAPGQEVTISCSGSSSNIGNNYVSWYQQLPGTAPKWYDN
NKRPSGIPDRFSGSKSGTSATLGITGLQTGDEADYYCGTWDSSLSALFGG
GTKLTVL
```

The VH CDR sequences for 205/207 VH are:

```
205/207 VH CDR1
                             (SEQ ID NO: 16)
GGSISSSSYY

205/207 VH CDR2
                             (SEQ ID NO: 17)
IYYSGST

205/207 VH CDR3
                             (SEQ ID NO: 55)
ARFHTWAPRAFDI
```

The VL CDR sequences for 205/207 VL are

```
              205/207 VL CDR1
                                      (SEQ ID NO: 27)
              SSNIGNNY

205/207 VL CDR2
                                      (SEQ ID NO: 28)
              DNN

205/207 VL CDR3
                                      (SEQ ID NO: 56)
              GTWDSSLSAL
```

The human antibody designated as R4CE-1E had VH and VL sequences:

```
R4CE-1E VH
                                              (SEQ ID NO: 57)
QVQLQESGSGLVKPSQTLSLTCTVSGGSISSSGYYWGWIRQPPGKGLEWI
GSIYHSGSTYYNPSLKSRVTISVDTSKNQFSLKLSSVTAADTAVYYCARV
QLWQRGFDYWGQGTLVTVSS

R4CE-1EVL
                                              (SEQ ID NO: 58)
DVVMTQSPLSLPVTPGEPASISCRSSQSLLHSNGYNYLDWYLQKPGQSPQ
LLIYLGSNRASGVPDRFSGSGSGTDFTLKINRVEAEDVGVYYCMQALQAP
LTFGGGTKVEIK
```

The VH CDR sequences for R4CE-1E VH are:

```
              R4CE-1E 8 VH CDR1
                                      (SEQ ID NO: 59)
              GGSISSSGYY

R4CE-1E 8 VH CDR2
                                      (SEQ ID NO: 60)
              IYHSGST

R4CE-1E 8 VH CDR3
                                      (SEQ ID NO: 61)
              ARVQLWQRGFDY
```

The VL CDR sequences for R4CE-1E VL are

```
              R4CE-1E 8 VL CDR1
                                      (SEQ ID NO: 62)
              QSLLHSNGYNY

R4CE-1E 8 VL CDR2
                                      (SEQ ID NO: 63)
              LGS

R4CE-1E 8 VL CDR3
                                      (SEQ ID NO: 64)
              MQALQAPLT
```

The human antibody designated as 2A-F8 had VH and VL sequences:

```
2A-F8 VH
                                              (SEQ ID NO: 65)
QVQLQQWGAGLLKPSETLSLTCAVYGGSFSGYYWSWIRQPPGKGLEWIGE
INHSGSTNYNPSLKSRVTISVDTSKNQFSLKLSSVTAADTAVYYCVTWSD
YRDYWGQGTLVTVSS

2A-F8VL
                                              (SEQ ID NO: 66)
EIVMTQSPGTLSLSPGERATLSCRASQSVTSRRVAWFQQKPGQAPRLLIY
GASSRATGIPDRFSGSGSGTDFTLTISRLEPEDFAVYYCQQYGSSPLTFG
GGTKVEIRRTVAAPSVFIFPPSDEQLKSGTASVVCLLNNFYPREAKVQWK
VDNALQSGNSQESVTEQDSKDSTYSLSSTLTLSKADYEKHKVYACEVTHQ
GLSSPVTKSFNRGEC
```

The VH CDR sequences for 2A-F8 VH are:

```
              2A-F8 9 VH CDR1
                                      (SEQ ID NO: 67)
              GGSFSGYY

2A-F8 9 VH CDR2
                                      (SEQ ID NO: 68)
              INHSGST

2A-F8 9 VH CDR3
                                      (SEQ ID NO: 69)
              VTWSDYRDY
```

The VL CDR sequences for 2A-F8 VL are

```
              2A-F8 9 VL CDR1
                                      (SEQ ID NO: 70)
              QSVTSRR

2A-F8 9 VL CDR2
                                      (SEQ ID NO: 71)
              GAS

2A-F8 9 VL CDR3
                                      (SEQ ID NO: 72)
              QQYGSSPLT
```

The human antibody designated as R4CE-7G had VH and VL sequences:

```
R4CE-7G VH
                                              (SEQ ID NO: 73)
QLQLQESGPGLVKPSETLSLTCTVSGGSISSSSYYWGWIRQPPGKGLEWI
GSIYYSGGTYYNPSLKSRVTISVDTSKNQFSLKLSSVTAADTAVYYCART
TYSYGPGFDPWGQGTLVTVSSASTKG

R4CE-7GVL
                                              (SEQ ID NO: 74)
QSVVTQPPSVSAAPGQKVTISCSGSSSNIGTYYVSWYQQFPGTVPKLLIY
DNTQRPSEIPDRFSASKSGTSVTLDITGLQTGDEGDYYCATWDSNLKSVV
FGGGTKVAVLGQPKAAPSVTLFPPSSEELQANKATLVCLISDFYPGAVTV
AWKADGSPVKAGVETTTPSKQSNNKYAASSYLSLTPEQWKSHRSYSCQVT
HEGSTVEKTVAPTECS
```

The VH CDR sequences for R4CE-7G are:

```
              R4CE-7G 10 VH CDR1
                                      (SEQ ID NO: 16)
              GGSISSSSYY

R4CE-7G 10 VH CDR2
                                      (SEQ ID NO: 75)
              IYYSGGT
```

-continued

R4CE-7G 10 VH CDR3
(SEQ ID NO: 76)
ARTTYSYGPGFDP

The VL CDR sequences for R4CE-7G are

R4CE-7G 10 VL CDR1
(SEQ ID NO: 77)
SSNIGTYY

R4CE-7G 10 VL CDR2
(SEQ ID NO: 78)
DNT

R4CE-7G 10 VL CDR3
(SEQ ID NO: 79)
ATWDSNLKSVV

The human antibody designated as R4CE-10H had VH and VL sequences:

R4CE-10H VH
(SEQ ID NO: 80)
QLQLQESGPGLVKPSQTLSLTCTVSGGSISSGGYYWSWIRQPPGKGLEWI

GSIYHSGSTYYNPSLKSRVTISVDTSKNQFSLKLSSVTAADTAVYYCARV

MYYYGSGSPYWYFDLWGRGTLVTVSS

R4CE-10H VL
(SEQ ID NO: 81)
QSVVTQPPSVSAAPGQKVTISCSGSSSNIGKNFVSWYQQFPGTAPKFLI

YENSKRPSGIPDRISGSKSGTSATLAITGLQTGDEADYYCGTWDSSLSAV

VFGGGTKLTVLSQPKAAPSVTLFPPSSEELQANKATLVCLISDFYPGAV

TVAWKADSSPVKAGVETTTPSKQSNNKYAASSY

The VH CDR sequences for R4CE-10H are:

R4CE-10H 11 VH CDR1
(SEQ ID NO: 82)
GGSISSGGYY

R4CE-10H 11 VH CDR2
(SEQ ID NO: 83)
IYHSGST

R4CE-10H 11 VH CDR3
(SEQ ID NO: 84)
ARVMYYYGSGSPYWYFDL

The VL CDR sequences for R4CE-10H are

R4CE-10H 11 VL CDR1
(SEQ ID NO: 85)
SSNIGKNF

R4CE-10H 11 VL CDR2
(SEQ ID NO: 86)
ENS

R4CE-10H 11 VL CDR3
(SEQ ID NO: 40)
GTWDSSLSAVV

The human antibody designated as 1B-6C had VH and VL sequences:

1B-6C VH
(SEQ ID NO: 87)
QVQLQESGPGLVKPSETLSLTCTVSGGSISSSSYYWGWIRQPPGKGLEWI

GSIYYSGSTYYNPSLKSRVTISLDTSKNQFSLKLSSLTAADTAVYYCARV

PAIRSSAIFDYWGQGTLVTVSS 1B-6C VL
(SEQ ID NO: 88)
QSVVTQPPSVSAAPGQKVTISCFGSRSNIGNNYVSWYQQFPGTAPQLLIF

DNNKRPSGIPDRFSGSKSGTSASLGITGVQTGDEAEYYCGAWDSSLSAG

AVFGGGTKLTVLGQPKAAPSVTLFPPSSEELQANKATLVCLISDFYPGAV

TVAWKADSSPVKAGVETTTPSKQSNNKYAASSYLSLTPEQWKSHRSYS

CQVTHEGSTVEKTVAPTECS

The VH CDR sequences for 1B-6C are:

1B-6C-12 VH CDR1
(SEQ ID NO: 16)
GGSISSSSYY 1B-6C-12 VH CDR2
(SEQ ID NO: 17)
IYYSGST 1B-6C-12 VH CDR3
(SEQ ID NO: 89)
ARVPAIRSSAIFDY

The VL CDR sequences for 1B-6C are 1B-6C-12 VL CDR1
(SEQ ID NO: 90)
RSNIGNNY 1B-6C-12 VL CDR2
(SEQ ID NO: 28)
DNN 1B-6C-12 VL CDR3
(SEQ ID NO: 91)
GAWDSSLSAGAV The human antibody designated as 1B-6E had VH and VL sequences:

1B-6E-13 VH
(SEQ ID NO: 92)
QVQLQESGPGLVKPSETLSLTCTVSGYSISSGYYWGWIRQPPGKGLEWIG

SIYHSGSTYYNPSLKSRVTISVDTSKNQFSLKLSSVTAADTAVYYCARVA

PYSSSPSFDYWGQGTLVTVSS 1B-6E VL
(SEQ ID NO: 93)
LPVLTQPPSASGTPGQRVTISCSGSSSNIGRNTGNWYQQLPGTAPKLLIY

SNNQRPSGVPDRFSGSKSGTSASLAISGLQSEDEADYYCAAWDDSLNGVV

FGGGTKVTVLGQPKAAPSVTLFPPSSEELQANKATLVCLISDFYPGAVTV

AWKADSSPVKAGVETTTPSKQSNNKYAASSYLSLTPEQWKSHRSYSCQV

THEGSTVEKTVAPAECS

The VH CDR sequences for 1B-6E are:

1B-6E-13 VH CDR1
(SEQ ID NO: 94)
GYSISSGYY 1B-6E-13 VH CDR2
(SEQ ID NO: 95)
IYHSGST 1B-6E-13 VH CDR3
(SEQ ID NO: 96)
ARVAPYSSSPSFDY

The VL CDR sequences for 1B-6E are 1B-6E-13 VL CDR1
(SEQ ID NO: 97)
SSNIGRNT 1B-6E-13 VL CDR2
(SEQ ID NO: 98)
SNN 1B-6E-13 VL CDR3
(SEQ ID NO: 99)
AAWDDSLNGVV The human antibody designated as 2A-5A had VH and VL sequences:

2A-5A VH
(SEQ ID NO: 100)
QVQLQESGPGLVKPSETLSLTCTVSGGSISSSSYYWGWIRQPPGKGLEWI
GSIYYSGSTYYNPSLKSRVTISVDTSKNQFSLKLSSVTAADTAVYYCARF
SRGGPFLWGRGTLVTVSS 2A-5AVL
(SEQ ID NO: 101)
QSVVTQPPSVSAAPGQKVTISCSGSSSNIGSYSVSWYQQLPGTAPKWY
DNNKRPSGIPDRFSGSKSGTSATLGITGLQTGDEADYYCGTWDSSLSAY
VFGSGTKVTVLGQPKANPTVTLFPPSSEELQANKATLVCLISDFYPGAV
TVAWKADGSPVKAGVETTKPSKQSNNKYAASSYLSLTPEQWKSHRSY
SCQVTHEGSTVEKTVAPTECS

The VH CDR sequences for 2A-5A are:

2A-5A-14 VH CDR1
(SEQ ID NO: 16)
GGSISSSSYY 2A-5A-14 VH CDR2
(SEQ ID NO: 17)
IYYSGST 2A-5A-14 VH CDR3
(SEQ ID NO: 102)
ARFSRGGPFL

The VL CDR sequences for 2A-5A are 2A-5A-14 VL CDR1
(SEQ ID NO: 103)
SSNIGSYS 2A-5A-14 VL CDR2
(SEQ ID NO: 28)
DNN 2A-5A-14 VL CDR3
(SEQ ID NO: 29)
GTWDSSLSAYV Eight of the human VH regions have the same CDR1 of GGSISSSSYY (SEQ ID NO: 16). Eight of the human VH regions have the same CDR2 of IYYSGST (SEQ ID NO: 17). Four of the human VL regions have the same CDR2 of DNN (SEQ ID NO: 28). Three of the human VL regions have the same CDR1 of SSNIGNNY (SEQ ID NO: 27). The above CDR sequences of the human antibodies can be grafted onto framework regions of antibodies from other species. The above human CDR sequences can also be mixed and matched in a combinatorial fashion to make new anti-MBG antibodies. The human anti-MBG antibodies can also be affinity matured using, for example, parsimonious mutagenesis (e.g., Balint and Larrick, 1993) to obtain anti-MBG antibodies with greater binding affinity for MBG.

Any of the anti-MBG antibodies disclosed herein can be put into a variety of formats including, for example, antibody fragments (including Fab, Fab', $F(ab')_2$, $F_v$, and other digestion fragments, as well as recombinant fragments such as, for example, scFv, diabody, triabody, tetrabody, Bis-scFv, minibody, Fab2, or Fab3) or a full length antibody such as IgA, IgD, IgE, IgG, and IgM. The IgG full length antibodies can be IgG1, IgG2, IgG3 or IgG4. Full length IgA can be IgA1 or IgA2.

The disclosure encompasses pharmaceutically acceptable salts of anti-MBG antibodies, including those with a positive net charge, those with a negative net charge, and those with no net charge, and including without limitation salts of anti-MBG antibodies including fragments thereof as compounds, in pharmaceutical compositions, in their therapeutic and diagnostic uses, and in their production.

III. Anti-MBG Antibody Modifications

An anti-MBG antibody can include a moiety that extends a half-life ($T_{1/2}$) or/and the duration of action of the antibody fragment. The moiety can extend the circulation $T_{1/2}$, blood $T_{1/2}$, plasma $T_{1/2}$, serum $T_{1/2}$, terminal $T_{1/2}$, biological $T_{1/2}$, elimination $T_{1/2}$ or functional $T_{1/2}$, or any combination thereof, of the antibody.

In certain embodiments, an anti-MBG antibody fragment comprises a single moiety. In other embodiments, an anti-MBG antibody fragment comprises two or more substantially similar or identical moieties or two or more moieties of the same type. In yet other embodiments, an anti-MBG antibody fragment comprises two or more moieties of different types, or two or more different types of moieties.

The moiety can be human serum albumin (HSA) or a portion thereof (e.g., domain III) that binds to the neonatal Fc receptor (FcRn). HSA has a nominal serum half-life of about 19 days due in part to its molecular weight (MW) of about 67 kDa and its highly anionic surface.

Covalent or non-covalent binding of a protein to HSA confers additional benefits. For example, HSA can shield the protein, thereby rendering the protein less susceptible to proteolytic cleavage and less immunogenic.

The main FcRn-binding site is in domain III of HSA. Domain III spans positions 388-585 of the 609-aa full-length HSA. Domain I also contributes to HSA binding to FcRn, which may partly explain why domain III as a single domain has an approximately 10-fold lower affinity for FcRn than full-length HSA.

The HSA or FcRn-binding portion thereof can optionally have one or more mutations that confer a beneficial property or effect. In some embodiments, the HSA or FcRn-binding portion thereof has one or more mutations that enhance pH-dependent HSA binding to FcRn or/and increase HSA half-life, such as K573P or/and E505G/V547A.

HSA or an FcRn-binding portion thereof can be attached to any suitable location or site on an anti-MBG antibody fragment. In some embodiments, HSA or an FcRn-binding portion thereof is recombinantly fused or chemically conjugated to the N-terminus or/and the C-terminus of the heavy chain or/and the light chain of an anti-MBG antibody fragment, optionally via a linker.

In further embodiments, the protracting moiety comprises or is a moiety that non-covalently binds to albumin (HSA). Attachment of an anti-MBG antibody fragment to an albumin-binding moiety allows the antibody fragment to enjoy the same benefits as attachment of the antibody fragment to HSA. Furthermore, non-covalent binding to HSA enables slow and sustained release of the antibody fragment from the HSA-antibody fragment complex. In addition, the albumin-binding moiety enables affinity purification of the antibody fragment based on binding to albumin.

In further embodiments, the protracting moiety comprises or is an unstructured polypeptide. Attachment of an unstructured polypeptide to a protein increases its half-life by increasing its MW, hydrodynamic radius/volume and overall size and thus reducing its renal clearance. Unstructured polypeptides generally have a backbone that adopts a random chain conformation in aqueous solution at body temperature and side chains that have a low tendency to engage in intramolecular interactions or intermolecular interactions other than those with water molecules, which generally favors small, hydrophilic amino acids with an uncharged side chain under physiological conditions. Hydrophobic amino acids may engage in intramolecular interactions or intermolecular interactions, including non-specific hydrophobic interactions with cell membranes and cell components. Among the uncharged, hydrophilic amino acids, threonine may form a β-sheet, cysteine may form a disulfide bond, tyrosine is rather large and its phenyl ring can engage in hydrophobic interaction, and asparagine and glutamine may form aggregates.

An unstructured polypeptide can be attached to any suitable location or site on an anti-MBG antibody fragment. In some embodiments, an unstructured polypeptide is recombinantly fused or chemically conjugated to the N-terminus or/and the C-terminus of the heavy chain or/and the light chain of an anti-MBG antibody fragment, optionally via linker. Likewise, an anti-MBG antibody fragment can be attached to any suitable location or site on an unstructured polypeptide. In some embodiments, an anti-MBG antibody fragment is recombinantly fused or chemically conjugated to the N-terminus or the C-terminus of an unstructured polypeptide, optionally via a linker.

In additional embodiments, the protracting moiety comprises or is a carboxy-terminal peptide (CTP) derived from the β-subunit of human chorionic gonadotropin (hCG). The protracting CTP (a CTP attached to a protein as a protracting moiety) can have the wild-type sequence of the hCG-β CTP, or can have one or more substitutions, additions or deletions, or any combination or all thereof, relative to the hCG-β CTP. A CTP can be attached to any suitable location or site on an anti-MBG antibody fragment. In some embodiments, a CTP is recombinantly fused or chemically conjugated to the N-terminus or/and the C-terminus of the heavy chain or/and the light chain of an anti-MBG antibody fragment, optionally via linker. Likewise, an anti-MBG antibody fragment can be attached to any suitable location or site on a CTP. In some embodiments, an anti-MBG antibody fragment is recombinantly fused or chemically conjugated to the N-terminus or the C-terminus of a CTP, optionally via a linker.

In some embodiments, a polypeptide protracting moiety is recombinantly fused to the N-terminus or the C-terminus of the heavy chain or the light chain of an anti-MBG antibody fragment, optionally via a linker. Recombinant fusion of a polypeptide protracting moiety to an antibody fragment facilitates manufacturing, avoids additional conjugation and purification steps, and minimizes product heterogeneity. In certain embodiments, a polypeptide protracting moiety is recombinantly fused to an anti-MBG antibody fragment via a linker. A linker/spacer decreases steric hindrance and promotes independent functioning of the antibody fragment and the protracting moiety. Use of a linker may also enhance expression of the fusion protein. In some embodiments, the linker contains about 4-30 amino acid residues. In certain embodiments, the linker contains from about 6 or 8 amino acid residues to about 20 amino acid residues, or from about 6 or 8 amino acid residues to about 15 amino acid residues.

In other embodiments, the protracting moiety comprises or is 1, 2, 3, 4, 5 or more moieties of a synthetic polymer. The synthetic polymer can be biodegradable or non-biodegradable. Biodegradable polymers useful as protracting moieties include, but are not limited to, poly(2-methacryloyloxyethyl phosphorylcholine) (PMPC) and poly[oligo (ethylene glycol) methyl ether methacrylate] (POEGMA). Non-biodegradable polymers useful as protracting moieties include without limitation poly(ethylene glycol) (PEG), polyglycerol, poly(N-(2-hydroxypropyl)methacrylamide) (PHPMA), polyoxazolines and poly(N-vinylpyrrolidone) (PVP).

In some embodiments, the synthetic polymer comprises or is PEG. Conjugation of one or more PEG moieties to a protein increases its half-life by increasing its MW, hydrodynamic radius/volume and overall size and thus reducing its renal clearance. PEGylation can increase the solubility, reduce the aggregation and immunogenicity, and avoid phagocytosis of the protein. PEG is flexible, uncharged and non-biodegradable, has relatively low immunogenicity, and has been approved by the US Food and Drug Administration as GRAS (generally recognized as safe). The one or more PEG moieties independently can be linear or branched. Furthermore, the one or more PEG moieties independently can terminate in a hydroxyl group, a methoxy group (mPEG) or another capped group.

In some embodiments, the individual mass (e.g., average molecular weight), or the total mass, of the one or more synthetic polymer moieties is about 10-50, 10-20, 20-30, 30-40 or 40-50 kDa, or about 10, 20, 30, 40 or 50 kDa. The individual mass (e.g., average MW), or the total mass, of the one or more synthetic polymer moieties can also be greater than about 50 kDa, such as about 50-100, 50-60, 60-70, 70-80, 80-90 or 90-100 kDa, or about 60, 70, 80, 90 or 100 kDa. Moreover, the mass (e.g., average MW) of an individual synthetic polymer moiety can be less than about 10 kDa, such as about 1-5 or 5-10 kDa, or about 5 kDa. In certain embodiments, the individual mass (e.g., average MW), or the total mass, of the one or more synthetic polymer (e.g., PEG) moieties is about 20 or 40 kDa. The half-life of the modified protein can be tuned based on the length of the synthetic polymer, with a longer polymer generally conferring a longer half-life.

One or more synthetic polymer moieties can be coupled to any suitable location(s) or site(s) on an anti-MBG antibody fragment. In some embodiments, one or more synthetic polymer moieties are chemically conjugated to the N-terminus, the C-terminus or/and one or more side chains [e.g., accessible lysine side-chain amino group(s) or cysteine thiol group(s)] of the heavy chain or/and the light chain of an anti-MBG antibody fragment, optionally via linker.

In some embodiments, the anti-MBG antibody fragment comprising one or more protracting moieties is a sdAb, scFv, Fv or Fab. In certain embodiments, the anti-MBG antibody fragment is the Fab 2A-F8.

As a non-limiting example, a non-human (e.g., murine), humanized or human MBG-binding $V_H$ or $V_L$ domain can be recombinantly fused to a polypeptide protracting moiety. Such an anti-MBG $V_H$- or $V_L$-protracting moiety fusion protein can be used alone or can be linked (e.g., via a disulfide bond or a linker) to a corresponding $V_L$ or $V_H$ domain that can optionally be fused to the same protracting moiety, a different protracting moiety or a non-protracting polypeptide (e.g., $V_H$-protracting moiety linked to $V_L$-protracting moiety).

IV. Pharmaceutical Compositions

Additional embodiments of the disclosure relate to pharmaceutical compositions comprising a chimeric, humanized or human anti-MBG antibody or a fragment thereof described herein, or a pharmaceutically acceptable salt, solvate or hydrate thereof, and one or more pharmaceutically acceptable excipients or carriers. The compositions can optionally contain an additional therapeutic agent. In general, a pharmaceutical composition contains a therapeutically effective amount of an anti-MBG antibody or a fragment thereof, one or more pharmaceutically acceptable excipients or carriers and optionally a therapeutically effective amount of an additional therapeutic agent, and is formulated for administration to a subject for therapeutic use. An anti-MBG antibody or a fragment thereof can also be administered to a subject for diagnostic use, such as for imaging.

Pharmaceutical compositions generally are prepared according to current good manufacturing practice (GMP), as recommended or required by, e.g., the Federal Food, Drug, and Cosmetic Act § 501(a)(2)(B) and the International Conference on Harmonisation Q7 Guideline.

Pharmaceutical compositions/formulations can be prepared in sterile form. For example, pharmaceutical compositions/formulations for parenteral administration by injection or infusion generally are sterile. Sterile pharmaceutical compositions/formulations are compounded or manufactured according to pharmaceutical-grade sterilization standards known to those of skill in the art, such as those disclosed in or required by the United States Pharmacopeia Chapters 797, 1072 and 1211, and 21 Code of Federal Regulations 211.

Pharmaceutically acceptable excipients and carriers include pharmaceutically acceptable substances, materials and vehicles. Non-limiting examples of types of excipients include liquid and solid fillers, diluents, binders, lubricants, glidants, surfactants, dispersing agents, disintegration agents, emulsifying agents, wetting agents, suspending agents, thickeners, solvents, isotonic agents, buffers, pH adjusters, absorption-delaying agents, stabilizers, antioxidants, preservatives, antimicrobial agents, antibacterial agents, antifungal agents, chelating agents, adjuvants, sweetening agents, flavoring agents, coloring agents, encapsulating materials and coating materials. The use of such excipients in pharmaceutical formulations is known in the art. For example, conventional vehicles and carriers include without limitation oils (e.g., vegetable oils such as olive oil and sesame oil), aqueous solvents {e.g., saline, buffered saline (e.g., phosphate-buffered saline [PBS]) and isotonic solutions (e.g., Ringer's solution)}, and organic solvents (e.g., dimethyl sulfoxide [DMSO] and alcohols [e.g., ethanol, glycerol and propylene glycol]). Except insofar as any conventional excipient or carrier is incompatible with an anti-MBG antibody or a fragment thereof, the disclosure encompasses the use of conventional excipients and carriers in formulations containing an anti-MBG antibody or a fragment thereof. See, e.g., Remington: The Science and Practice of Pharmacy, 21st Ed., Lippincott Williams & Wilkins (Philadelphia, Pa.) (2005); Handbook of Pharmaceutical Excipients, 5th Ed., Rowe et al., Eds., The Pharmaceutical Press and the American Pharmaceutical Association (2005); Handbook of Pharmaceutical Additives, 3rd Ed., Ash and Ash, Eds., Gower Publishing Co. (2007); and Pharmaceutical Pre-formulation and Formulation, Gibson, Ed., CRC Press (Boca Raton, Fla.) (2004).

Appropriate formulation can depend on various factors, such as the route of administration chosen. Potential routes of administration of a pharmaceutical composition comprising an anti-MBG antibody or a fragment thereof include without limitation oral, parenteral (including intradermal, subcutaneous, intramuscular, intravascular, intravenous, intraarterial, intraperitoneal, intramedullary, intrathecal and topical), intracavitary, and topical (including dermal/epicutaneous, transdermal, mucosal, transmucosal, intranasal [e.g., by nasal spray or drop], intraocular [e.g., by eye drop], pulmonary [e.g., by oral or nasal inhalation], buccal, sublingual, rectal [e.g., by suppository], and vaginal [e.g., by suppository]). Topical formulations can be designed to produce a local or systemic therapeutic effect. In certain embodiments, an anti-MBG antibody or a fragment thereof is administered parenterally (e.g., intravenously, subcutaneously, intramuscularly or intraperitoneally) by injection (e.g., as a bolus) or by infusion over a period of time.

Excipients and carriers that can be used to prepare parenteral formulations include without limitation solvents (e.g., aqueous solvents such as water, saline, physiological saline, buffered saline [e.g., phosphate-buffered saline], balanced salt solutions [e.g., Ringer's BSS] and aqueous dextrose solutions), isotonic/iso-osmotic agents (e.g., salts [e.g., NaCl, KCl and $CaCl_2$] and sugars [e.g., sucrose]), buffering agents and pH adjusters (e.g., sodium dihydrogen phosphate [monobasic sodium phosphate]/disodium hydrogen phosphate [dibasic sodium phosphate], citric acid/sodium citrate and L-histidine/L-histidine HCl), and emulsifiers (e.g., non-ionic surfactants such as polysorbates [e.g., polysorbate 20 and 80] and poloxamers [e.g., poloxamer 188]). Protein formulations and delivery systems are discussed in, e.g., A. J. Banga, Therapeutic Peptides and Proteins: Formulation, Processing, and Delivery Systems, 3rd Ed., CRC Press (Boca Raton, Fla.) (2015).

The excipients can optionally include one or more substances that increase protein stability, increase protein solubility, inhibit protein aggregation or reduce solution viscosity, or any combination or all thereof. Examples of such substances include without limitation hydrophilic amino acids (e.g., arginine and histidine), polyols (e.g., myo-inositol, mannitol and sorbitol), saccharides {e.g., glucose (including D-glucose [dextrose]), lactose, sucrose and trehalose}, osmolytes (e.g., trehalose, taurine, amino acids [e.g., glycine, sarcosine, alanine, proline, serine, β-alanine and γ-aminobutyric acid], and betaines [e.g., trimethylglycine and trimethylamine N-oxide]), and non-ionic surfactants {e.g., alkyl polyglycosides, ProTek® alkylsaccharides (e.g., a monosaccharide [e.g., glucose] or a disaccharide [e.g., maltose or sucrose] coupled to a long-chain fatty acid or a corresponding long-chain alcohol), and polypropylene glycol/polyethylene glycol block co-polymers (e.g., poloxamers [e.g., Pluronic™ F-68], and Genapol® PF-10 and variants thereof)}. Because such substances increase protein solubility, they can be used to increase protein concentration in a formulation. Higher protein concentration in a formulation is particularly advantageous for subcutaneous administration, which has a limited volume of bolus administration (e.g., ≤about 1.5 mL). In addition, such substances can be used to stabilize proteins during the preparation, storage and reconstitution of lyophilized proteins.

For parenteral (e.g., intravenous, subcutaneous or intramuscular) administration, a sterile solution or suspension of an anti-MBG antibody or a fragment thereof in an aqueous solvent containing one or more excipients can be prepared beforehand and can be provided in, e.g., a pre-filled syringe. Alternatively, an anti-MBG antibody or a fragment thereof can be dissolved or suspended in an aqueous solvent that can optionally contain one or more excipients prior to lyophilization (freeze-drying). Shortly prior to parenteral administration, the lyophilized anti-MBG antibody or fragment thereof stored in a suitable container (e.g., a vial) can be reconstituted with, e.g., sterile water that can optionally contain one or more excipients. If the anti-MBG antibody or fragment thereof is to be administered by infusion (e.g., intravenously), the solution or suspension of the reconstituted anti-MBG antibody or fragment thereof can be added to and diluted in an infusion bag containing, e.g., sterile saline (e.g., about 0.9% NaCl).

Excipients that enhance transmucosal penetration of smaller proteins include without limitation cyclodextrins, alky saccharides (e.g., alkyl glycosides and alkyl maltosides [e.g., tetradecylmaltoside]), and bile acids (e.g., cholic acid, glycocholic acid, taurocholic acid, deoxycholic acid, glycodeoxycholic acid, chenodeoxycholic acid and dehydrocholic acid).

Excipients that enhance transepithelial or transdermal penetration of smaller proteins include without limitation chemical penetration enhancers (CPEs, including fatty acids [e.g., oleic acid]), cell-penetrating peptides {CPPs, including arginine-rich CPPs [e.g., polyarginines such as $R_6$-$R_{11}$ (e.g., $R_6$ and $R_9$) and TAT-related CPPs such as TAT(49-57)] and amphipathic CPPs [e.g., Pep-1 and penetratin]}, and skin-penetrating peptides (SPPs, such as the skin-penetrating and cell-entering [SPACE] peptide). Transdermal penetration of smaller proteins can be further enhanced by use of a physical enhancement technique, such as iontophoresis, cavitational or non-cavitational ultrasound, electroporation, thermal ablation, radio frequency, microdermabrasion, microneedles or jet injection. US 2007/0269379 provides an extensive list of CPEs. F. Milletti, *Drug Discov. Today,* 17:850-860 (2012) is a review of CPPs. R. Ruan et al., *Ther. Deliv.,* 7:89-100 (2016) discuss CPPs and SPPs for transdermal delivery of macromolecules, and M. Prausnitz and R. Langer, *Nat. Biotechnol.,* 26:1261-1268 (2008) discuss a variety of transdermal drug-delivery methods.

In some embodiments, an anti-MBG antibody or a fragment thereof is delivered from a sustained-release composition. As used herein, the term "sustained-release composition" encompasses sustained-release, prolonged-release, extended-release, slow-release and controlled-release compositions, systems and devices. Protein delivery systems are discussed in, e.g., Banga (supra). A sustained-release composition can deliver a therapeutically effective amount of an anti-MBG antibody or a fragment thereof over a prolonged time period. In some embodiments, a sustained-release composition delivers an anti-MBG antibody or a fragment thereof over a period of at least about 3 days, 1 week, 2 weeks, 3 weeks, 1 month (4 weeks), 6 weeks, 2 months, 3 months or longer. A sustained-release composition can be administered, e.g., parenterally (e.g., intravenously, subcutaneously or intramuscularly).

A sustained-release composition of a protein can be in the form of, e.g., a particulate system, a lipid or oily composition, or an implant. Particulate systems include without limitation nanoparticles, nanospheres, nanocapsules, microparticles, microspheres and microcapsules. Nanoparticulate systems generally have a diameter or an equivalent dimension smaller than about 1 µm. In certain embodiments, a nanoparticle, nanosphere or nanocapsule has a diameter or an equivalent dimension of no more than about 500, 400 or 300 nm, or no more than about 200, 150 or 100 nm. In some embodiments, a microparticle, microsphere or microcapsule has a diameter or an equivalent dimension of about 1-200, 100-200 or 50-150 µm, or about 1-100, 1-50 or 50-100 µm. A nano- or microcapsule typically contains the therapeutic agent in the central core, while the therapeutic agent typically is dispersed throughout a nano- or microparticle or sphere. In certain embodiments, a nanoparticulate system is administered intravenously, while a microparticulate system is administered subcutaneously or intramuscularly.

In some embodiments, a sustained-release particulate system or implant is made of a biodegradable polymer or/and a hydrogel. In certain embodiments, the biodegradable polymer comprises lactic acid or/and glycolic acid [e.g., an L-lactic acid-based copolymer, such as poly(L-lactide-co-glycolide) or poly(L-lactic acid-co-D,L-2-hydroxyoctanoic acid)]. Non-limiting examples of polymers of which a hydrogel can be composed include polyvinyl alcohol, acrylate polymers (e.g., sodium polyacrylate), and other homopolymers and copolymers having a relatively large number of hydrophilic groups (e.g., hydroxyl or/and carboxylate groups). The biodegradable polymer of the particulate system or implant can be selected so that the polymer substantially completely degrades around the time the period of treatment is expected to end, and so that the byproducts of the polymer's degradation, like the polymer, are biocompatible.

Alternatively, a sustained-release composition of a protein can be composed of a non-biodegradable polymer. Examples of non-biodegradable polymers include without limitation poloxamers (e.g., poloxamer 407). Sustained-release compositions of a protein can be composed of other natural or synthetic substances or materials, such as hydroxyapatite.

Sustained-release lipid or oily compositions of a protein can be in the form of, e.g., liposomes, micelles (e.g., those composed of biodegradable natural or/and synthetic polymers, such as lactosomes), and emulsions in an oil.

A sustained-release composition can be formulated or designed as a depot, which can be injected or implanted, e.g., subcutaneously or intramuscularly. A depot can be in the form of, e.g., a polymeric particulate system, a polymeric implant, or a lipid or oily composition. A depot formulation can comprise a mixture of a protein and, e.g., a biodegradable polymer [e.g., poly(lactide-co-glycolide)] or a semi-biodegradable polymer (e.g., a block copolymer of lactic acid and PEG) in a biocompatible solvent system, whether or not such a mixture forms a particulate system or implant.

A pharmaceutical composition can be presented in unit dosage form as a single dose wherein all active and inactive ingredients are combined in a suitable system, and components do not need to be mixed to form the composition to be administered. The unit dosage form generally contains an effective dose of the therapeutic agent. A representative example of a unit dosage form is a single-use pen comprising a pre-filled syringe, a needle and a needle cover for parenteral (e.g., intravenous, subcutaneous or intramuscular) injection of the therapeutic agent.

Alternatively, a pharmaceutical composition can be presented as a kit in which the therapeutic agent, excipients and carriers (e.g., solvents) are provided in two or more separate containers (e.g., ampules, vials, tubes, bottles or syringes) and need to be combined to form the composition to be administered. The kit can contain instructions for storing, preparing and administering the composition (e.g., a solution to be injected intravenously or subcutaneously).

A kit can contain all active and inactive ingredients in unit dosage form or the active ingredient and inactive ingredients in two or more separate containers, and can contain instructions for administering or using the pharmaceutical composition to treat a medical condition.

In some embodiments, a kit contains an anti-MBG antibody or a fragment thereof or a pharmaceutical composition comprising the same, and instructions for administering or using the anti-MBG antibody or fragment thereof or the pharmaceutical composition comprising the same to treat an MBG-associated disorder.

V. Therapeutic Uses of Anti-MBG Antibodies and Fragments Thereof

The anti-MBG antibodies described above can be administered to subjects suffering from MBG-associated diseases or syndromes. When the subject is a human, the anti-MBG antibody can be a chimeric mouse-human antibody, a humanized antibody, or a human antibody. Such chimeric, humanized and human antibodies are described above. MBG-associated diseases and syndromes include, for example, acute respiratory distress syndrome, traumatic brain injury, hypertension (e.g., essential hypertension), hypertension-associated disorders (e.g., pre-eclampsia), and fibrosis-associated disorders (e.g., nonalcoholic steatohepatitis, diabetic nephropathy). MBG-associated diseases also include severely ill patients with a background of sepsis, trauma, and complicated severe pneumonia and burns.

Elevated levels of marinobufagenin (MBG) is associated with subjects afflicted with acute respiratory distress syndrome. Acute respiratory distress syndrome (ARDS) is a life-threatening disorder with a prevalence rate of 64 cases per 100,000 person-years and a mortality rate of 40-52%. The MBG related effects of acute respiratory distress syndrome can be address by administering anti-MBG antibodies to the subject. The anti-MBG antibodies remove MBG from the subject and so lower the elevated levels of MBG. The reduction in MBG levels should reduce the deleterious impacts from the elevated MBG.

Elevated levels of marinobufagenin (MBG) is associated with subjects suffering from traumatic brain injuries (e.g., a concussion). MBG not only initiates inflammation but also maintains the inflammatory response. Traumatic brain injury is associated with increased permeability of the blood-brain-barrier and MBG can cross the BBB and enter the central nervous system. Administration of anti-MBG antibodies either systemically or to the CNS directly can lower MBG in the CNS by clearing the MBG from the system (and lowering CNS MBG by allowing more CNS MBG to enter the blood), or lowering MBG in the CNS by antibody mediated clearance. The reduction in MBG levels can reduce CNS inflammation in the subject, and reduce other MBG associated effects in the CNS.

Essential hypertension, also known as primary or idiopathic hypertension, affects about 90-95% of hypertensive patients. Essential hypertension mainly results from vasoconstriction or volume expansion (Laragh 1982). Volume expansion is an increase of fluid in the blood due to increased sodium and water retention. Excessive volume expansion can be caused by, e.g., high dietary NaCl intake or compromised sodium handling in patients with a disorder such as congestive heart failure (CHF), kidney failure or liver failure. Marinobufagenin (MBG) is a cardiotonic steroid (CTS) with effects similar to digitalis. MBG is an important regulator of blood pressure and is implicated in the pathogenesis of hypertension and hypertension-associated disorders. MBG is a potent vasoconstrictor (Bagrov, *EJP* 1995). In addition, volume expansion induces MBG synthesis and secretion, including in volume expansion-associated conditions such as essential hypertension, primary aldosteronism, pre-eclampsia (PE), CHF and chronic renal failure (Bagrov 2009). MBG is a causative factor in pre-eclampsia, for example, via induction of vasoconstriction and vascular fibrosis. Administration of MBG to normal pregnant rats causes an increase in blood pressure similar to that observed in pregnant rats drinking saline water and injected with the aldosterone precursor desoxycorticosterone acetate (DOCA), a volume-expansion rat model of PE (Vu 2005). Plasma MBG level is 5-fold higher in PE patients than in normotensive pregnant women, and plasma MBG level correlates with PE severity (Lopatin 1999 and Agunanne 2011). Furthermore, plasma MBG level increases 7-fold in patients with essential hypertension or CHF, and over 70-fold in patients with chronic renal failure (Puschett, AJKD 2010).

Elevated plasma MBG levels are associated with a variety of disorders that are characterized by reduced $Na^+/K^+$-ATPase (NKA) pumping activity, including pre-eclampsia (Graves 1987), congestive heart failure (Schwinger 1999), myocardial ischemia/infarction (Bagrov 1991), diabetes (including types 1 and 2) (Bagrov 2005), and obstructive sleep apnea (Bagrov, *Hypertension* 1995 and Paci 2000).

MBG inhibits proliferation, migration and invasion of cytotrophoblast (CTB) cells, which are critical for normal placental development (LaMarca 2006 and Uddin, *Placenta* 2008). In about 7% of all births, PE is characterized by failure of CTB cells to invade the uterus and its vasculature, particularly the spiral arteries that endovascular CTB cells should invade. This results in decreased blood flow through the placenta to the fetus, which can cause intrauterine growth restriction (IUGR). Furthermore, MBG binding to NKA induces p38-mediated apoptosis and stress signaling in an extravillous CTB cell line (Ehrig 2015). Moreover, MBG induces apoptosis mediated by the MAPKs p38 and c-Jun $NH_2$-terminal kinase (Jnk), and p38-mediated production and secretion of IL-6 (which mediates cell proliferation, cell differentiation, apoptosis and inflammation), in an extravillous CTB cell line (Uddin, *JBC* 2008).

In addition, MBG causes endothelial dysfunction by inducing apoptosis of and disrupting tight junctions between endothelial cells, which increases vascular permeability/leakage characteristic of PE (Uddin, *AJN* and *AJPRICP* 2009). Endothelial dysfunction as well as vascular inflammation also contribute to increased peripheral resistance and vascular damage in hypertension (Versari 2009 and Marchesi 2008).

MBG binding to NKA stimulates EGFR-mediated cell signaling that results in oxidative stress and fibrosis (Bagrov 2008). MBG induces fibrosis in renal and cardiovascular tissues, including cardiac fibrosis in uremic cardiomyopathy (Kennedy 2006 and Elkareh 2007 and 2009). Fibrosis is formation of excess fibrous connective tissue in an organ or tissue in a reparative or reactive process, typically in response to damage or inflammation. Fibrosis involves stimulated fibroblasts laying down connective tissue, including collagen and glycosaminoglycans. Collagen, along with elastin, is the principal fibrous scleroprotein in connective tissues. The transcription factor Fli-1 is a negative regulator (suppressor) of transcription of procollagens I and III and inhibits TGF-β-induced collagen synthesis (Kubo 2003 and Czuwara-Ladykowska 2001). Binding of MBG at low concentrations to NKA on fibroblasts leads to activation of PLC and then PKC-δ as described above. Activation of PKC-δ induces its translocation into the nucleus, where it phosphorylates Fli-1, thereby rendering Fli-1 prone to proteolytic degradation. Proteolysis of phosphorylated Fli-1 results in increased expression of procollagens I and III and collagen synthesis and hence fibrosis (Elkareh 2009). Type I collagen is the most abundant collagen of the human body, forms collagen fibers, and is present in scar tissue. Type III collagen is present in extensible connective tissues such as the lungs, the skin and the vascular system, often in association with type I collagen. Fli-1 participates in the pathogenesis of a range of fibrotic diseases including localized and systemic scleroderma, where Fli-1 deficiency promotes production of collagen in fibrotic dermal and vascular lesions (Kubo 2003, and Asano AJP and JDS 2010).

MBG induces vascular fibrosis in PE (Nikitina 2011), and arterial stiffness characterizes pre-eclamptic and chronic hypertensive pregnancies (Tihtonen 2006 and Kaihura 2009). Umbilical arteries from PE patients exhibit reduced Fli-1 expression, increased expression of procollagens I and III, and impaired response to the vasorelaxant effect of sodium nitroprusside following endothelin-1-induced vasoconstriction, and ex vivo treatment of normal umbilical arteries explants with 1 and 10 nM MBG for 24 hr mimics the same features of PE (Nikitina 2011).

MBG triggers periglomerular and peritubular fibrosis in the renal cortex and formation of fibrotic scars in the corticomedullary junction of the kidney, in part by inducing an epithelial-to-mesenchymal transition (EMT) in renal epithelial cells (Fedorova 2009). MBG at subnanomolar concentrations potently stimulates collagen synthesis by normal renal and cardiac fibroblasts (Elkareh 2009 and 2007). NKA binds to Src kinase and functions as a signaling complex in response to binding of a CTS such as MBG to NKA on renal and cardiovascular cells (Tian 2006). Activation of Src is required for induction of collagen synthesis by fibroblasts (Elkareh 2007).

Fibrosis impairs the structure and function of the affected organ (e.g., heart or kidney) or tissue (e.g., vascular system or renal tubular system). With respect to DN, MBG binds to NKA on renal fibroblasts and renal epithelial cells (including those of the renal tubular system), and at low concentrations MBG induces NKA/Src-initiated signaling cascades that lead to collagen production and fibrosis without inhibiting NKA pumping activity. MBG preferentially binds to the $\alpha_1$ isoform of NKA, which is the main isoform in the kidney, including renal fibroblasts and renal epithelial cells (including those of the renal tubular system) (Bagrov 2009). MBG activation of the NKA/Src signaling complex leads to collagen production by renal fibroblasts and fibrosis via promotion of proteolytic degradation of the transcription factor Fli-1, a suppressor of expression of procollagens I and III, by PKC-δ phosphorylation of Fli-1, as described above. In addition, MBG causes fibrotic changes in epithelial cells of the renal tubular system, including the proximal tubule, by inducing EMT (Fedorova 2009).

Fibrosis is associated with a wide variety of disorders. Examples of disorders in which fibrosis occurs include without limitation pre-eclampsia, cardiomyopathy (e.g., diabetic cardiomyopathy and uremic cardiomyopathy), cardiac fibrosis, myocardial fibrosis, collagen-vascular diseases (e.g., arterial stiffness and vascular fibrosis), atherosclerosis, chronic heart failure, diabetic nephropathy, glomerulosclerosis, renal fibrosis, tubulointerstitial fibrosis, chronic kidney disease (e.g., chronic renal failure), hepatic fibrosis, cirrhosis, non-alcoholic fatty liver disease. non-alcoholic steatohepatitis), alcoholic liver disease (e.g., alcoholic steatohepatitis), chronic liver disease, liver failure (e.g., cirrhosis and chronic liver failure), pulmonary fibrosis, nephrogenic systemic fibrosis (which may affect the skin and internal organs such as the heart, liver and lungs), and scleroderma (including localized scleroderma and systemic scleroderma/systemic sclerosis [which may affect the skin, blood vessels, muscles and internal organs such as the heart, kidneys, lungs and gastrointestinal tract]).

Hypertension also characterizes (e.g., is a clinical feature or complication of) or is a major risk factor for (e.g., causes or contributes to) a wide range of disorders. Non-limiting examples of disorders with which hypertension is associated include pre-eclampsia, eclampsia, edema (e.g., systemic edema, peripheral edema, pulmonary edema and cerebral edema), cardiovascular diseases {e.g., hypertensive heart disease, fibrotic disorders (e.g., cardiomyopathy [e.g., diabetic cardiomyopathy and uremic cardiomyopathy], myocardial fibrosis and collagen-vascular diseases [e.g., arterial stiffness]), arteriosclerosis (e.g., atherosclerosis and arteriolosclerosis), heart failure (e.g., congestive heart failure, left-sided heart failure and right-sided heart failure), coronary artery diseases (e.g., myocardial ischemia/infarction), aortic dissection, peripheral vascular diseases (e.g., peripheral artery disease), and stroke}, kidney disorders (e.g., hypertensive nephropathy, diabetic nephropathy, glomerulonephritis, renal ischemia, nephrotic syndrome, kidney failure [e.g., acute kidney injury and chronic kidney disease], hematuria, proteinuria and uremia), liver failure (e.g., cirrhosis), cerebral disorders (e.g., hypertensive encephalopathy, cerebral hemorrhage, intracranial hemorrhage, intracranial hypertension, stroke [e.g., ischemic stroke and hemorrhagic stroke], and cerebral infarction), eye disorders (e.g., retinopathy [e.g., hypertensive retinopathy], damage to blood vessels in the eye, papilledema, retinal hemorrhage and vision loss), fibrinoid necrosis (e.g., of arterioles), metabolic syndrome, diabetes (e.g., type 2), and sleep apnea (e.g., obstructive sleep apnea).

The chimeric, humanized and human anti-MBG antibodies and fragments thereof described herein can be used to treat any MBG-associated disorders. In certain embodiments, the antibody or fragment thereof is H2L2, H3L2, 201/202, 206/208, 236/237 or 2A-F8. In some embodiments, the disorders are associated with an elevated level of MBG, such as in the blood, urine or cerebrospinal fluid (CSF). Non-limiting examples of MBG-associated disorders include hypertension (e.g., essential [primary or idiopathic] hypertension, secondary hypertension [e.g., renovascular hypertension, portal hypertension or pulmonary hypertension], volume expansion-associated hypertension, resistant hypertension and hypertensive emergency [malignant hypertension]), hypertensive disorders of pregnancy (e.g., chronic hypertension, pre-eclampsia, eclampsia and gestational hypertension), edema (e.g., systemic edema and peripheral edema), cardiovascular disorders {e.g., hypertensive heart disease, fibrotic disorders (e.g., cardiomyopathy [e.g., diabetic cardiomyopathy and uremic cardiomyopathy], cardiac fibrosis, myocardial fibrosis [e.g., endomyocardial fibrosis] and collagen-vascular diseases [e.g., arterial stiffness and vascular fibrosis]), arteriosclerosis (e.g., atherosclerosis and arteriolosclerosis), heart failure (e.g., acute heart failure, chronic heart failure, congestive heart failure, left-sided heart failure/left ventricular dysfunction, and right-sided heart failure), coronary artery diseases (e.g., angina and myocardial ischemia/infarction), aortic dissection, peripheral vascular diseases (e.g., peripheral artery disease), and stroke}, kidney/renal disorders {e.g., hypertensive nephropathy, diabetic nephropathy, glomerulonephritis, glomerulosclerosis, renal fibrosis, tubulointerstitial fibrosis, renal ischemia, nephrotic syndrome, renal failure (e.g., acute kidney injury, acute-on-chronic kidney failure, and chronic kidney disease [e.g., chronic renal failure and end-stage renal disease]), hematuria, proteinuria and uremia}, liver disorders {e.g., hepatic fibrosis, cirrhosis, non-alcoholic fatty liver disease (e.g., non-alcoholic steatohepatitis), alcoholic liver disease (e.g., alcoholic steatohepatitis), chronic liver disease, and liver failure (e.g., cirrhosis and chronic liver failure)}, lung disorders (e.g., pulmonary edema and pulmonary fibrosis [e.g., idiopathic pulmonary fibrosis]), cerebral disorders (e.g., hypertensive encephalopathy, cerebral hemorrhage, intracranial hemorrhage, cerebral edema, intracranial hypertension, brain swelling, stroke [e.g., ischemic stroke and hemorrhagic stroke], and cerebral infarction), eye disorders (e.g., retinopathy [e.g., hypertensive retinopathy], damage to blood vessels in the eye, papilledema [papilloedema], retinal hemorrhage, and vision impairment and loss), skin disorders (e.g., nephrogenic systemic fibrosis [which may also affect internal organs such as the heart, liver and lungs] and scleroderma [including localized scleroderma and systemic scleroderma/systemic sclerosis [which may also affect blood vessels, muscles and internal organs such as the heart, kidneys, lungs and gastrointestinal tract), fibrinoid necrosis (e.g., of arterioles), metabolic syndrome, diabetes mellitus (including types 1 and 2), and sleep apnea (e.g., obstructive sleep apnea).

In some embodiments, a chimeric, humanized or human anti-MBG antibody or a fragment thereof (e.g., H2L2, H3L2, 201/202, 206/208, 236/237 or 2A-F8) is used to treat a hypertensive disorder. In certain embodiments, the hypertension comprises, or is, high arterial blood pressure. In some embodiments, the hypertensive disorder is hypertension (e.g., essential hypertension, volume expansion-associated hypertension or resistant hypertension), a hypertensive disorder of pregnancy (e.g., chronic hypertension or pre-eclampsia), or other hypertension-associated disorder {e.g., a cardiovascular disorder (e.g., hypertensive heart disease, heart failure [e.g., congestive heart failure] or a coronary artery disease [e.g., myocardial ischemia/infarction]) or a kidney disorder (e.g., hypertensive nephropathy, diabetic nephropathy or kidney failure [e.g., chronic kidney disease])}. In certain embodiments, the hypertensive disorder is essential hypertension, pre-eclampsia, congestive heart failure or chronic kidney disease.

In further embodiments, a chimeric, humanized or human anti-MBG antibody or a fragment thereof (e.g., H2L2, H3L2, 201/202, 206/208, 236/237 or 2A-F8) is used to treat a fibrotic disorder. In some embodiments, the fibrotic disorder is pre-eclampsia, cardiomyopathy (e.g., diabetic cardiomyopathy or uremic cardiomyopathy), cardiac fibrosis, myocardial fibrosis, a collagen-vascular disease (e.g., arterial stiffness or vascular fibrosis), atherosclerosis, chronic heart failure, diabetic nephropathy, renal fibrosis, chronic kidney disease (e.g., chronic renal failure), hepatic fibrosis, cirrhosis, non-alcoholic steatohepatitis, chronic liver disease, liver failure (e.g., chronic liver failure), or scleroderma (e.g., localized scleroderma or systemic scleroderma/systemic sclerosis). In certain embodiments, the fibrotic disorder is uremic cardiomyopathy, myocardial fibrosis, diabetic nephropathy, renal fibrosis or cirrhosis.

A chimeric, humanized or human anti-MBG antibody or a fragment thereof (e.g., H2L2, H3L2, 201/202, 206/208, 236/237 or 2A-F8) can be administered to a subject via any suitable route. Potential routes of administration of the antibody or fragment thereof include without limitation oral, parenteral (including intradermal, subcutaneous, intramuscular, intravascular, intravenous, intraarterial and intraperitoneal), and intracavitary. In some embodiments, the antibody or fragment thereof is administered parenterally (e.g., intravenously, subcutaneously, intramuscularly or intraperitoneally) by injection or infusion (e.g., with an osmotic pump). The antibody or fragment thereof can also be administered by other routes depending in part on the type of disorder. For instance, the antibody or fragment thereof can be administered by, e.g., oral inhalation using, e.g., a metered-dose inhaler, a dry powder inhaler or a nebulizer to treat a lung disorder. As another example, the antibody or fragment thereof can be administered by, e.g., intramedullary, intrathecal, intracranial, intracerebral or intracerebroventricular injection to treat a cerebral disorder. As a further example, the antibody or fragment thereof can be administered by, e.g., intravitreal, subconjunctival, subretinal or sub-Tenon's injection or implant to treat an eye disorder. Alternatively, the antibody or fragment thereof can be administered topically by eye drop to treat an eye disorder, where penetration of the antibody or fragment thereof into the posterior segment or/and the anterior segment of the eye can by enhanced by co-administration of a cell-penetrating peptide (CPP), such as an arginine-rich CPP [e.g., a polyarginine such as $R_6$—$R_{11}$ (e.g., $R_6$ or $R_9$) or a TAT-related CPP such as TAT(49-57)] or an amphipathic CPP (e.g., Pep-1 or penetratin). As an additional example, the antibody or fragment thereof can be administered, e.g., transdermally to treat a skin disorder, where penetration of the antibody or fragment thereof into and through the skin can be enhanced by co-administration of a chemical penetration enhancer (CPE) (e.g., a fatty acid such as oleic acid), a CPP (e.g., an arginine-rich CPP such as a polyarginine or a TAT-related CPP) or a skin-penetrating peptide (SPP) (e.g., the skin-penetrating and cell-entering [SPACE] peptide), or any combination or all thereof, or/and by use of a physical enhancement technique, such as iontophoresis, cavitational or non-cavitational ultrasound, electroporation, thermal ablation, radio frequency, microdermabrasion, microneedles or jet injection.

The therapeutically effective amount and the frequency of administration of, and the length of treatment with, a chimeric, humanized or human anti-MBG antibody or a fragment thereof to treat an MBG-associated disorder may depend on various factors, including the nature and severity of the disorder, the potency of the antibody or fragment thereof, the mode of administration, the age, body weight, general health, gender and diet of the subject, and the response of the subject to the treatment, and can be determined by the treating physician. In some embodiments, the therapeutically effective amount of the antibody or fragment thereof (e.g., H2L2, H3L2, 201/202, 206/208, 236/237 or 2A-F8) for the treatment of an MBG-associated disorder is from about 1, 5 or 10 mg to about 200 mg, from about 1, 5 or 10 mg to about 150 mg, from about 1, 5 or 10 mg to about 100 mg, or from about 1, 5 or 10 mg to about 50 mg, or as deemed appropriate by the treating physician, which can be administered in a single dose or in divided doses. In further embodiments, the therapeutically effective amount of the antibody or fragment thereof is about 1-5 mg, 5-10 mg, 10-20 mg, 20-30 mg, 30-40 mg, 40-50 mg, 50-100 mg, 100-150 mg or 150-200 mg. In some embodiments, the therapeutically effective amount of the antibody or fragment thereof is about 1, 5, 10, 15, 20, 25, 30, 40, 50, 60, 70, 80, 90, 100, 150 or 200 mg. In certain embodiments, the therapeutically effective amount of the antibody or fragment thereof is about 1-5 mg, 5-10 mg or 10-50 mg. In additional embodiments, the therapeutically effective amount of the antibody or fragment thereof (e.g., H2L2, H3L2, 201/202, 206/208, 236/237 or 2A-F8) for the treatment of an MBG-associated disorder is about 0.01-0.1 mg/kg, 0.1-0.5 mg/kg, 0.5-1 mg/kg, 1-2 mg/kg or 2-3 mg/kg body weight, or as deemed appropriate by the treating physician. In certain embodiments, the therapeutically effective amount of the antibody or fragment thereof is about 0.01-0.1 mg/kg, 0.1-0.5 mg/kg or 0.5-1 mg/kg body weight.

A chimeric, humanized or human anti-MBG antibody or a fragment thereof can be administered in any suitable frequency to treat an MBG-associated disorder. In some embodiments, the antibody or fragment thereof (e.g., H2L2, H3L2, 201/202, 206/208, 236/237 or 2A-F8) is administered once daily, once every 2 days, once every 3 days, twice weekly, once weekly, once every 2 weeks, once every 3 weeks, once monthly, once every 6 weeks, once every 2 months or once every 3 months, or as deemed appropriate by the treating physician. In certain embodiments, the antibody or fragment thereof is administered once weekly or once every 2 weeks.

Likewise, a chimeric, humanized or human anti-MBG antibody or a fragment thereof can be administered for any suitable length of time, or in any suitable total number of doses, to treat an MBG-associated disorder. In some embodiments, the antibody or fragment thereof (e.g., H2L2, H3L2, 201/202, 206/208, 236/237 or 2A-F8) is administered over a period of at least about 1 week, 2 weeks, 1 month (4 weeks), 6 weeks, 2 months, 3 months, 6 months, 1 year, 2 years, 3 years or longer, or as deemed appropriate by the treating physician. In some embodiments, the MBG-associated disorder is a chronic condition. A chronic condition can exist for, e.g., at least about 6 weeks or 2 months. In certain embodiments, the antibody or fragment thereof is administered over a period of at least about 6 weeks, 2 months, 3 months or 6 months. In additional embodiments, 1, 2, 3, 4, 5 or 6 doses of the antibody or fragment thereof (e.g., H2L2, H3L2, 201/202, 206/208, 236/237 or 2A-F8) are administered for the entire treatment regimen. In certain embodiments, 1, 2 or 3 doses of the antibody or fragment thereof are administered for the entire treatment regimen.

A chimeric, humanized or human anti-MBG antibody or a fragment thereof (e.g., H2L2, H3L2, 201/202, 206/208, 236/237 or 2A-F8) can also be administered in an irregular manner to treat an MBG-associated disorder. For example, the antibody or fragment thereof can be administered 1, 2, 3, 4, 5 or more times in a period of 1 week, 2 weeks, 3 weeks, 1 month, 2 months or 3 months in an irregular manner. Furthermore, an anti-MBG antibody or a fragment thereof (e.g., H2L2, H3L2, 201/202, 206/208, 236/237 or 2A-F8) can be taken pro re nata (as needed) for treatment of an MBG-associated disorder. For instance, the antibody or fragment thereof can be administered 1, 2, 3, 4, 5 or more times, whether in a regular or irregular manner, for treatment of hypertension until blood pressure is lowered to a certain level. Once blood pressure is reduced to a certain level, dosing of the antibody or fragment thereof can optionally be discontinued. If blood pressure reaches or surpasses a certain level, administration of the antibody or fragment thereof, whether in a regular or irregular manner, can be resumed. The appropriate dosage of, frequency of dosing of and length of treatment with the antibody or fragment thereof can be determined by the treating physician.

For a more rapid establishment of a therapeutic level of a chimeric, humanized or human anti-MBG antibody or a fragment thereof, at least one loading dose of the antibody or fragment thereof can be administered prior to the maintenance dose. In some embodiments, a loading dose of the antibody or fragment thereof (e.g., H2L2, H3L2, 201/202, 206/208, 236/237 or 2A-F8) is administered, followed by (i) one or more additional loading doses and then one or more therapeutically effective maintenance doses, or (ii) one or more therapeutically effective maintenance doses without an additional loading dose, as deemed appropriate by the treating physician. A loading dose of a drug is typically larger (e.g., about 1.5, 2, 3, 4 or 5 times larger) than a subsequent maintenance dose and is designed to establish a therapeutic level of the drug more quickly. The one or more therapeutically effective maintenance doses can be any therapeutically effective amount described herein. In certain embodiments, the loading dose is about 2 or 3 times larger than the maintenance dose. In some embodiments, a loading dose of the antibody or fragment thereof is administered on day 1, and a maintenance dose of the antibody or fragment thereof is administered, e.g., once weekly or once every 2 weeks thereafter for the duration of treatment. In certain embodiments, the antibody or fragment thereof (e.g., H2L2, H3L2, 201/202, 206/208, 236/237 or 2A-F8) is administered in a loading dose of about 2-10 mg, 10-20 mg or 20-100 mg, or about 3-15 mg, 15-30 mg or 30-150 mg, on day 1, followed by a maintenance dose of about 1-5 mg, 5-10 mg or 10-50 mg once weekly or once every 2 weeks for the duration of treatment (e.g., for at least about 2, 3 or 6 months), where the loading dose is about 2 or 3 times larger than the maintenance dose and the antibody or fragment thereof is administered parenterally (e.g., intravenously, subcutaneously or intramuscularly).

In some embodiments, two loading doses of the antibody or fragment thereof are administered prior to the maintenance dose. In some embodiments, a first loading dose of the antibody or fragment thereof is administered on day 1, a second loading dose is administered, e.g., about 1 or 2 weeks later, and a maintenance dose is administered, e.g., once weekly or once every 2 weeks thereafter for the duration of treatment. In certain embodiment, the first loading dose is about 3 or 4 times larger than the maintenance dose, and the second loading dose is about 2 times larger than the maintenance dose. In some embodiments, the antibody or fragment thereof (e.g., H2L2, H3L2, 201/202, 206/208, 236/237 or 2A-F8) is administered in a first loading dose of about 3-15 mg, 15-30 mg or 30-150 mg, or about 4-20 mg, 20-40 mg or 40-200 mg, on day 1, in a second loading dose of about 2-10 mg, 10-20 mg or 20-100 mg about 1 or 2 weeks later, followed by a maintenance dose of about 1-5 mg, 5-10 mg or 10-50 mg once weekly or once every 2 weeks for the duration of treatment (e.g., for at least about 2, 3 or 6 months), where the first loading dose is about 3 or 4 times larger than the maintenance dose, the second loading dose is about 2 times larger than the maintenance dose, and the antibody or fragment thereof is administered parenterally (e.g., intravenously, subcutaneously or intramuscularly).

In some embodiments, one or more additional therapeutic agents are used in combination with a chimeric, humanized or human anti-MBG antibody or a fragment thereof (e.g., H2L2, H3L2, 201/202, 206/208, 236/237 or 2A-F8) to treat an MBG-associated disorder, as described below.

The disclosure provides a method of treating an MBG-associated disorder, comprising administering to a subject in need of treatment a therapeutically effective amount of a chimeric, humanized or human anti-MBG antibody or a fragment thereof described herein, optionally in combination with an additional therapeutic agent. The disclosure further provides a chimeric, humanized or human anti-MBG antibody or a fragment thereof described herein, or a composition comprising a chimeric, humanized or human anti-MBG antibody or a fragment thereof described herein, for use as a medicament, optionally in combination with an additional therapeutic agent. In addition, the disclosure provides for the use of a chimeric, humanized or human anti-MBG antibody or a fragment thereof described herein in the preparation of a medicament, optionally in combination with an additional therapeutic agent. In some embodiments, the medicament is used for treatment of an MBG-associated disorder.

VI. Combination Therapies with Additional Therapeutic Agents

One or more additional therapeutic agents can optionally be used in combination with a chimeric, humanized or human anti-MBG antibody or a fragment thereof (e.g., H2L2, H3L2, 201/202, 206/208, 236/237 or 2A-F8) to treat an MBG-associated disorder. The optional additional therapeutic agent(s) can be administered to a subject concurrently with (e.g., in the same composition as the antibody or fragment thereof or in separate compositions) or sequentially to (before or after) administration of the antibody or fragment thereof.

In some embodiments, the optional additional therapeutic agent(s) are selected from MBG inhibitors, magnesium sulfate, antihypertensive agents, antidyslipidemic agents, antiplatelet agents, anticoagulants, anti-inflammatory agents, antioxidants, antifibrotic agents, and combinations thereof.

Examples of MBG inhibitors include without limitation resibufogenin (RBG), spironolactone, canrenone, and analogs, derivatives and salts thereof. Spironolactone is a competitive antagonist of the $Na^+/K^+$-ATPase CTS-binding site. Canrenone is the major metabolite of spironolactone.

Magnesium sulfate can have antihypertensive effect and can potentiate the activity of anti-MBG antibodies and fragments thereof. Magnesium also lowers high blood pressure in a dose-dependent manner.

In some embodiments, one or more antihypertensive agents are used in combination with a chimeric, humanized or human anti-MBG antibody or a fragment thereof (e.g., H2L2, H3L2, 201/202, 206/208, 236/237 or 2A-F8) to treat hypertension or a hypertension-associated disorder. Antihypertensive agents include without limitation: MBG inhibitors, antagonists of the renin-angiotensin-aldosterone system (RAAS), diuretics, calcium channel blockers, $\alpha_2$-adrenoreceptor agonists, $\alpha_1$-adrenoreceptor antagonists (alpha blockers), β-adrenoreceptor ($β_1$ or/and $β_2$) antagonists (beta blockers), mixed alpha/beta blockers, vasodilators, endothelin receptor antagonists, protein kinase C inhibitors (PKC exerts a vasoconstricting effect on VSMCs), inhibitors of the accumulation or effects of advanced glycation end-products (AGEs, which inhibit vasodilation by interfering with nitric oxide), minerals, and analogs, derivatives and salts thereof.

In further embodiments, a chimeric, humanized or human anti-MBG antibody or a fragment thereof (e.g., H2L2, H3L2, 201/202, 206/208, 236/237 or 2A-F8) is used in conjunction with an antidyslipidemic agent, an antiplatelet agent or an anticoagulant, or any combination or all thereof, to treat a cardiovascular or cerebrovascular disorder. In certain embodiments, the antidyslipidemic agent includes or is a statin (e.g., atorvastatin or a salt thereof) or/and a fibrate (e.g., fenofibrate), the antiplatelet agent includes or is a COX-1 inhibitor (e.g., aspirin) or/and a $P2Y_{12}$ inhibitor (e.g., clopidogrel), and the anticoagulant includes or is a direct factor Xa inhibitor (e.g., apixaban or rivaroxaban) or/and a direct thrombin inhibitor (e.g., dabigatran). In addition, an antidyslipidemic agent (e.g., a statin such as atorvastatin or a salt thereof) can be used in combination with an anti-MBG antibody or a fragment thereof (e.g., H2L2, H3L2, 201/202, 206/208, 236/237 or 2A-F8) to treat an obesity-associated disorder (e.g., metabolic syndrome or type 2 diabetes). Statins also possess anti-inflammatory (e.g., inhibit secretion of pro-inflammatory IL-6 and IL-8) and antioxidant (e.g., reduce oxidative stress-induced cell injury) properties.

Antidyslipidemic agents include without limitation: HMG-CoA reductase inhibitors, acetyl-CoA carboxylase (ACC) inhibitors, peroxisome proliferator-activated receptor-alpha (PPAR-α) agonists, PPAR-δ agonists, PPAR-γ agonists, liver X receptor (LXR) agonists, retinoid X receptor (RXR) agonists, inhibitors of acyl-CoA cholesterol acyltransferase (ACAT, also called sterol O-acyltransferase [SOAT], including ACAT1 [SOAT1] and ACAT2 [SOAT2]), inhibitors of stearoyl-CoA desaturase-1 (SCD-1, also called stearoyl-CoA delta-9 desaturase) activity or expression, cholesterylester transfer protein (CETP) inhibitors, inhibitors of microsomal triglyceride transfer protein (MTTP) activity or expression, glucagon-like peptide-1 (GLP-1) receptor agonists, dipeptidyl peptidase 4 (DPP-4) inhibitors, inhibitors of pro-protein convertase subtilisin/kexin type 9 (PCSK9) activity or expression, apolipoprotein mimetic peptides, omega-3 fatty acids, and analogs, derivatives and salts thereof.

Antiplatelet agents include without limitation: cyclooxygenase (e.g., COX-1) inhibitors, thromboxane (e.g., $A_2$) synthase inhibitors, thromboxane (e.g., $A_2$) receptor antagonists, adenosine diphosphate (ADP) receptor/$P2Y_{12}$ inhibitors, adenosine reuptake inhibitors, glycoprotein IIb/IIIa inhibitors, phosphodiesterase (e.g., PDE3 or/and PDE5) inhibitors, protease-activated receptor 1 (PAR1) antagonists, prostacyclin and analogs thereof, and analogs, derivatives and salts thereof.

Anticoagulants include without limitation: vitamin K antagonists, indirect factor Xa inhibitors, direct factor Xa inhibitors, direct thrombin (factor IIa) inhibitors (DTIs), and analogs, derivatives and salts thereof.

Inflammation contributes to the pathophysiology of a wide range of disorders. Inflammatory disorders include without limitation autoimmune diseases (e.g., type 1 diabetes, multiple sclerosis and systemic sclerosis), hypertension, pre-eclampsia, edema, cardiovascular disorders (e.g., atherosclerosis, myocardial ischemia/infarction, ischemia-reperfusion injury [IRI] and peripheral artery disease), cerebral disorders (e.g., stroke and IRI), kidney disorders (e.g., glomerulonephritis), liver disorders (e.g., cirrhosis, non-alcoholic and alcoholic steatohepatitis, and chronic liver disease), eye disorders (e.g., age-related macular degeneration [AMD]), metabolic syndrome, diabetes (types 1 and 2), and sleep apnea (e.g., obstructive sleep apnea). Furthermore, inflammation is a major stimulant of fibrosis.

In some embodiments, one or more anti-inflammatory agents are used in combination with a chimeric, humanized or human anti-MBG antibody or a fragment thereof (e.g., H2L2, H3L2, 201/202, 206/208, 236/237 or 2A-F8) to treat an inflammatory disorder. In certain embodiments, the one or more anti-inflammatory agents include, or are, an inhibitor of a pro-inflammatory cytokine or a receptor therefor or the production thereof (e.g., TNF-α or/and IL-6 or IL-6R).

Anti-inflammatory agents include without limitation: non-steroidal anti-inflammatory drugs (NSAIDs), immunomodulators, immunosuppressants, anti-inflammatory cytokines and compounds that increase their production, inhibitors of pro-inflammatory cytokines or receptors therefor, inhibitors of the production of pro-inflammatory cytokines or receptors therefor, inhibitors of pro-inflammatory transcription factors or their activation or expression, inhibitors of pro-inflammatory prostaglandins (e.g., prostaglandin $E_2$ [$PGE_2$]) or receptors therefor (e.g., $EP_3$) or the production thereof, inhibitors of leukotrienes or receptors therefor or the production thereof, inhibitors of phospholipase A2 (e.g., secreted and cytosolic PLA2), suppressors of C-reactive protein (CRP) activity or level, mast cell stabilizers, phosphodiesterase inhibitors, specialized pro-resolving mediators (SPMs), other kinds of anti-inflammatory agents, and analogs, derivatives, fragments and salts thereof.

Non-steroidal anti-inflammatory drugs (NSAIDs) include without limitation: acetic acid derivatives, anthranilic acid derivatives (fenamates), enolic acid derivatives (oxicams), propionic acid derivatives, salicylates, COX-2-selective inhibitors, other kinds of NSAIDs, such as monoterpenoids (e.g., eucalyptol and phenols [e.g., carvacrol]), anilinopyridinecarboxylic acids (e.g., clonixin), sulfonanilides (e.g., nimesulide), and dual inhibitors of lipooxygenase (e.g., 5-LOX) and cyclooxygenase (e.g., COX-2) (e.g., chebulagic acid, licofelone, 2-(3,4,5-trimethoxyphenyl)-4-(N-methylindol-3-yl)thiophene, and di-tert-butylphenol-based compounds [e.g., DTPBHZ, DTPINH, DTPNHZ and DTPSAL]); and analogs, derivatives and salts thereof.

The glucocorticoid class of corticosteroids has anti-inflammatory and immunosuppressive properties. Glucocorticoids include without limitation hydrocortisone types, halogenated steroids, carbonates, and analogs, derivatives and salts thereof.

Oxidative stress involving, e.g., reactive oxygen species (ROS, such as superoxide radical, singlet oxygen, hydroxyl radical, peroxyl radicals, hydrogen peroxide and organic hydroperoxides [e.g., lipid hydroperoxides]), reactive nitrogen species (RNS, such as nitric oxide radical, peroxynitrite, nitrogen dioxide and dinitrogen trioxide) and radicals (e.g., carbonate radical) also plays an important role in the pathophysiology of a wide variety of disorders. Oxidative disorders characterized by, e.g., oxidative stress or/and oxidative damage/injury include without limitation pre-eclampsia, cardiovascular disorders (e.g., atherosclerosis, heart failure, myocardial ischemia/infarction and IRI), cerebral disorders (e.g., stroke and IRI), neurodegenerative diseases (e.g., amyotrophic lateral sclerosis, multiple sclerosis and Alzheimer's, Huntington's and Parkinson's diseases), kidney disorders (e.g., diabetic nephropathy), liver disorders (e.g., cirrhosis), eye disorders (e.g., AMD), metabolic syndrome, diabetes (types 1 and 2), and sleep apnea (e.g., obstructive sleep apnea). Furthermore, oxidants (e.g., ROS and RNS) and oxidized molecules (e.g., oxidized lipids) can be highly inflammatory.

In some embodiments, one or more antioxidants are used in conjunction with a chimeric, humanized or human anti-MBG antibody or a fragment thereof (e.g., H2L2, H3L2, 201/202, 206/208, 236/237 or 2A-F8) to treat an oxidative disorder. In certain embodiments, the one or more antioxidants include, or are, a vitamin or an analog thereof (e.g., vitamin E or an analog thereof such as α-tocopherol or trolox) or/and an ROS, RNS or radical scavenger (e.g., melatonin or/and glutathione).

Antioxidants include without limitation: vitamins and analogs thereof, carotenoids, sulfur-containing antioxidants, scavengers of ROS, RNS and radicals, inhibitors of enzymes that produce ROS, substances that mimic or increase the activity or production of antioxidant enzymes, activators of transcription factors that upregulate expression of antioxidant enzymes, mitochondria-targeted antioxidants, other kinds of antioxidants, and analogs, derivatives and salts thereof.

In additional embodiments, one or more antifibrotic agents are used in combination with a chimeric, humanized or human anti-MBG antibody or a fragment thereof (e.g., H2L2, H3L2, 201/202, 206/208, 236/237 or 2A-F8) to treat a fibrosis-associated disorder. In some embodiments, the one or more antifibrotic agents include, or are, an anti-inflammatory agent or/and an antioxidant (e.g., vitamin E or an analog thereof [e.g., α-tocopherol or trolox], a sulfur-containing antioxidant or an ROS, RNS or radical scavenger [e.g., melatonin], or any combination thereof). In certain embodiments, the one or more antifibrotic agents include, or are, pirfenidone (which among its various antifibrotic and anti-inflammatory properties described herein also reduces fibroblast proliferation) or/and nintedanib (which blocks signaling of FGFR, PDGFR and VEGFR involved in fibroblast proliferation, migration and transformation).

In further embodiments, the one or more antifibrotic agents include, or are, one or more agents that have anti-hyperglycemic or/and insulin-sensitizing activity for treatment of a fibrotic disorder in which hyperglycemia, diabetes or insulin resistance contributes to development of fibrosis. Examples of such disorders include without limitation diabetic nephropathy, which is characterized by renal fibrosis, and non-alcoholic steatohepatitis (NASH) and cirrhosis, both of which are characterized by hepatic fibrosis. Use of anti-hyperglycemic or/and insulin-sensitizing agent(s) can curtail or prevent, e.g., renal inflammation and fibrosis or hepatic inflammation and fibrosis. In certain embodiments, the one or more antifibrotic agents include, or are, a PPAR-γ agonist (e.g., a thiazolidinedione [supra], such as pioglitazone or rosiglitazone). PPARγ-activating thiazolidinediones have both anti-hyperglycemic and insulin-sensitizing properties.

Antifibrotic agents include without limitation: MBG inhibitors, inhibitors of collagen accumulation, inhibitors of pro-fibrotic growth factors (e.g., TGF-β [including TGF-β1], CTGF and platelet-derived growth factor [including PDGF-B, PDGF-C and PDGF-D]) or their production, activation or signaling, receptor tyrosine kinase (TK) inhibitors, anti-EGFR antibodies, anti-inflammatory agents, including those listed above, antioxidants, including those listed above, antagonists of the renin-angiotensin-aldosterone system (RAAS), including those listed above, inhibitors of the accumulation or effects of advanced glycation end-products (AGEs, which inter alia increase arterial stiffness and stimulate mesangial matrix expansion), other kinds of antifibrotic agents, including but not limited to RGD mimetics and analogs (inhibit adhesion of fibroblasts and immune cells to ECM glycoproteins) (e.g., NS-11, SF-6,5 and GRGDS), galectin-3 inhibitors (e.g., GM-CT-01 and GR-MD-02), trichostatin A (inhibits TGFβ1-induced EMT), and PPAR-γ agonists (e.g., thiazolidinediones [supra]); and analogs, derivatives, fragments and salts thereof.

The optional additional therapeutic agent(s) independently can be administered in any suitable mode. Potential modes of administration include without limitation oral, parenteral (including intradermal, subcutaneous, intramuscular, intravascular, intravenous, intraarterial, intraperitoneal, intramedullary, intrathecal and topical), intracavitary, and topical (including dermal/epicutaneous, transdermal, mucosal, transmucosal, intranasal [e.g., by nasal spray or drop], intraocular [e.g., by eye drop], pulmonary [e.g., by oral or nasal inhalation], buccal, sublingual, rectal [e.g., by suppository] and vaginal [e.g., by suppository]). In some embodiments, the optional additional therapeutic agent(s) independently are administered orally or parenterally (e.g., intravenously, subcutaneously or intramuscularly).

The optional additional therapeutic agent(s) independently can be administered in any suitable frequency, including without limitation daily (1, 2 or more times per day), every two or three days, twice weekly, once weekly, every two weeks, every three weeks, monthly, every two months or every three months, or in an irregular manner or on an as-needed basis. The dosing frequency can depend on, e.g., the mode of administration chosen. The length of treatment with the optional additional therapeutic agent(s) can be determined by the treating physician and can independently be, e.g., at least about 1 day, 2 days, 3 days, 4 days, 1 week, 2 weeks, 3 weeks, 4 weeks (1 month), 6 weeks, 2 months, 3 months, 6 months, 1 year, 2 years, 3 years or longer.

VII. Diagnostic Uses of Anti-MBG Antibodies and Fragments Thereof

The chimeric, humanized and human anti-MBG antibodies and fragments thereof disclosed herein are also useful in diagnostic and prognostic assessment of MBG-associated disorders, including those associated with elevated MBG levels (e.g., hypertensive disorders). Furthermore, such antibodies and fragments thereof can be used to facilitate treatment decisions.

An anti-MBG antibody or a fragment thereof can be employed to detect the presence of MBG in an original or processed sample obtained from a subject. A biological sample can comprise, e.g., blood, plasma, serum, urine, cerebrospinal fluid (CSF), cells or tissue. A sample can be analyzed directly, extracted before analysis, or expanded in volume by the addition of a suitable solvent.

In some embodiments, a biological sample is contacted with an anti-MBG antibody or a fragment thereof, and the sample is screened to detect binding of the antibody or fragment thereof to MBG. Detection of such binding indicates the presence of MBG in the sample. In certain embodiments, the anti-MBG antibody or fragment thereof is labeled with a detectable agent (e.g., a fluorescent dye), so that binding of the antibody or fragment thereof to MBG evokes a signal. In other embodiments, MBG in a biological sample is immobilized on a surface prior to introduction of a labeled anti-MBG antibody or a fragment thereof (a direct assay), and the amount of the signal, corresponding to the amount of labeled antibody or fragment thereof bound to MBG, correlates to the amount of MBG in the sample. In yet other embodiments, MBG in a biological sample is captured by an unlabeled first antibody immobilized on a surface, and then is detected by a labeled second antibody that binds to the captured MBG and produces a signal in proportion to the amount of captured MBG (a sandwich assay), where the unlabeled first antibody and the labeled second antibody bind to different epitopes of MBG, and the unlabeled first antibody or/and the labeled second antibody independently can be an anti-MBG antibody or a fragment thereof disclosed herein.

In additional embodiments, MBG in a biological sample is detected in a competitive assay. In some embodiments, a sample (optionally suspended in a buffer) is mixed with a labeled anti-MBG antibody or a fragment thereof. The resulting mixture is then contacted with an MBG-coated substrate. To facilitate MBG coating of the substrate (e.g., a well of a microtiter plate), MBG can be conjugated to, e.g., a carrier protein (e.g., bovine serum albumin [BSA], keyhole limpet hemocyanin [KLH] or ovalbumin) that adsorbs onto the substrate. The greater the amount of MBG in the sample, the more antibody/MBG complexes are formed and the less unbound (free) antibody is available to bind to MBG on the substrate ("competition"), and hence the lower the signal produced.

In the direct, sandwich and competitive assays described above, the primary anti-MBG antibody or fragment thereof can be labeled with a detectable agent. Alternatively, in the direct, sandwich and competitive assays, the primary anti-MBG antibody or fragment thereof can be unlabeled and can be bound by a labeled secondary antibody (one that binds to, e.g., the Fc region of the primary antibody) after binding of the primary antibody to MBG. If the secondary antibody is conjugated to an enzyme, addition of a substrate of the enzyme results in an enzyme/substrate reaction that generates a signal (e.g., a chromogenic, fluorescent or electrochemical signal). The absorbance, fluorescence or electrochemical signal (e.g., current) of the solid support (e.g., a plate well or a bead) is measured to determine the presence and quantity of MBG in the sample. Non-limiting examples of substrates of horseradish peroxidase (HRP) include 3-amino-9-ethylcarbazole (AEC), 3,3'-diaminobenzidine (DAB) and 3,3',5,5'-tetramethylbenzidine (TMB), those of alkaline phosphatase include 5-bromo-4-chloro-3-indolyl phosphate (BCIP), and those of β-glucuronidase include 5-bromo-4-chloro-3-indolyl-β-D-glucuronide (X-Gluc). Such an assay is called an enzyme-linked immunosorbant assay (ELISA).

Detectable agents include without limitation chromophores {e.g., dyes, stains, pigments and chromogens (e.g., 3-amino-9-ethylcarbazole [AEC], 5-bromo-4-chloro-3-indolyl phosphate [BCIP], 3,3'-diaminobenzidine [DAB] and 3,3',5,5'-tetramethylbenzidine [TMB])}, fluorophores/fluorochromes (e.g., fluorescent dyes such as fluorescein, fluorescein isothiocyanate and rhodamine), chemiluminescent compounds (e.g., luciferin and luminol), radioisotopes (e.g., $^3$H, $^{14}$C, $^{32}$P, $^{35}$S and $^{125}$I), radioactive elements (e.g., technetium), electron-dense compounds, magnetic substances and particles (e.g., paramagnetic and superparamagnetic ones), magnetic resonance imaging (MM) contrast agents (e.g., gadolinium-containing ones), enzymes (e.g., horseradish peroxidase [HRP], alkaline phosphatase, luciferase, β-glucuronidase and β-galactosidase), haptens and toxins.

The anti-MBG antibodies and fragments thereof described herein can be employed in a variety of immunometric assays. Such assays include without limitation chromogenic, fluorescence, chemiluminescence, light scattering, radiolabeled, electrochemical, enzyme, precipitation, agglutination, coagulation, Western blot, grid blot, tissue blot, dot blot, dip stick, and biosensor assays. See, e.g., Principles and Practice of Immunoassays, C. Price and D. Newman (Eds.), Stockton Press (1997); and The Immunoassay Handbook, 2nd Ed., D. Wild (Ed.), Nature Publishing Group (2001). Furthermore, the anti-MBG antibodies and fragments thereof can be utilized in imaging, such as by MM.

Detection and measurement of the amount of MBG in a biological sample can facilitate diagnosis, prognosis and treatment of MBG-associated disorders. In some embodiments, a disorder is associated with an elevated level of MBG, and an elevated level of MBG in a sample from a subject compared to the level of MBG in a corresponding sample from other subject(s) without the disorder is indicative of diagnosis of the disorder in the subject. The reference MBG level for purposes of diagnosis of the disorder can be determined based on, e.g., a comparison of the MBG level in a corresponding sample from a statistically or epidemiologically significant number of subjects without the disorder to the MBG level in a corresponding sample from a statistically or epidemiologically significant number of subjects with the disorder. Similarly, for treatment and prognostic purposes the level of MBG in a sample from a subject can be compared to, e.g., a scale of MBG levels correlated with the severity of an MBG-associated disorder to determine the current severity of the disorder and to predict the probable course or outcome (e.g., progression or regression) of the disorder.

In addition, detection and measurement of the amount of MBG in a biological sample can facilitate treatment decisions. In some embodiments, the amount of an anti-MBG antibody or a fragment thereof administered to a subject or/and the frequency of administration of the antibody or fragment thereof to the subject are maintained or adjusted (increased or reduced), or administration of the antibody or fragment thereof to the subject is stopped, based on the presence, absence, amount or level of MBG in a sample from the subject.

In some embodiments, a kit contains an anti-MBG antibody or a fragment thereof that can optionally be labeled with a detectable agent, and optionally instructions for using the anti-MBG antibody or fragment thereof for a diagnostic application (e.g., in an immunoassay).

Blood MBG level is elevated in hypertension and hypertension-associated disorders. For instance, plasma MBG level is 5-fold higher in pre-eclamptic (PE) patients than in normotensive pregnant women, and plasma MBG level correlates with PE severity (Lopatin 1999 and Agunanne 2011). Furthermore, plasma MBG level increases 7-fold in patients with essential hypertension or congestive heart failure (CHF), and over 70-fold in patients with chronic renal failure (Puschett, AJKD 2010). Severity of CHF correlates with plasma MBG level (Fridman 2002). In addition, plasma MBG level is elevated in patients with myocardial ischemia/infarction (Bagrov 1998), and plasma MBG level is elevated in patients with obstructive sleep apnea (OSA) and correlates with severity of OSA (Zvartau 2006).

Other cardiotonic steroids, including other bufadienolides such as telocinobufagin (TCB) and resibufogenin (RBG), may also be diagnostic of disorders. For example, plasma TCB level is elevated in patients with chronic renal failure (Komiyama 2005). RBG blocks the effects of MBG, or has the opposite effects as MBG (Puschett 2012 and Uddin, H P 2012).

Angiogenic imbalance induced by MBG contributes to PE (Uddin, T R 2012). Angiogenic balance involves anti-angiogenic factors (e.g., soluble fms-like tyrosine kinase 1 [sFlt1 or sVEGFR1] and soluble endoglin [sEng]) and pro-angiogenic factors (e.g., vascular endothelial growth factor [VEGF] and placental growth factor [P1GF]). In PE patients, sFlt1 and sEng levels are increased prior to clinical symptoms and also correlate with PE severity, whereas P1GF level is significantly reduced (Verlohren 2012 and Hagmann 2012). For instance, excess placenta-derived sFlt1 contributes to endothelial dysfunction, hypertension and proteinuria in PE (Maynard 2003), and elevated level of placenta-derived sEng, a soluble TGF-β co-receptor, induces vascular permeability, hypertension and IUGR in PE (Venkatesha 2006). MBG at a concentration between 0.1 nM and 1 nM increases expression of sFlt1 and sEng and reduces expression of VEGF and P1GF in a cell line of extravillous CTB (Ehrig 2014). sFLt1:P1GF ratio is particularly useful for determining abnormal placental development and angiogenic imbalance that are characteristic of PE (Hertig 2010 and von Dadelszen 2014), and blood pressure during pregnancy positively correlates with sFlt1:P1GF ratio.

VIII. Production of Anti-MBG Antibodies and Fragments Thereof

The disclosure provides polynucleotides comprising nucleic acid sequences that encode chimeric, humanized and human anti-MBG antibodies and fragments thereof described herein. In some embodiments, a polynucleotide comprises a nucleic acid sequence that encodes the $V_H$ domain or/and the $V_L$ domain of an anti-MBG mAb or a fragment thereof. In further embodiments, a polynucleotide comprises a nucleic acid sequence that encodes the heavy chain or/and the light chain of an anti-MBG mAb or a fragment thereof.

The disclosure further provides vectors (which may also be called expression or cloning vectors) comprising nucleic acid sequences that encode chimeric, humanized and human anti-MBG antibodies and fragments thereof described herein. Suitable vectors include, but are not limited to, plasmids, cosmids, bacterial artificial chromosomes, yeast artificial chromosomes, lambda phages (e.g., those with lysogeny genes deleted), and viruses. In certain embodiments, a vector is a plasmid.

Various vector systems can be employed. One class of vectors utilizes DNA elements derived from animal viruses such as adenovirus, baculovirus, bovine papilloma virus, polyoma virus, SV40 virus, vaccinia virus, and retroviruses (e.g., MMTV, MOMLV and rous sarcoma virus). Another class of vectors utilizes RNA elements derived from RNA viruses such as eastern equine encephalitis virus, flaviviruses and Semliki Forest virus.

A vector can comprise various other elements for optimal expression of mRNA in addition to a nucleic acid sequence that encodes, e.g., the $V_H$ domain or/and the $V_L$ domain, or the heavy chain or/and the light chain, of an anti-MBG mAb or a fragment thereof. For example, a vector can contain a transcriptional promoter, a promoter plus an operator, an enhancer, an open reading frame with or without intron(s) or/and exon(s), a termination signal, a splice signal, a secretion signal sequence or a selectable marker (e.g, a gene conferring resistance to an antibiotic or cytotoxic agent), or any combination or all thereof.

The disclosure also provides host cells comprising or expressing vectors that encode chimeric, humanized and human anti-MBG antibodies and fragments thereof described herein. Suitable host cells include, but are not limited to, eukaryotic cells, mammalian cells (e.g., BHK, CHO, COS, HEK293, HeLa, MDCKII and Vero cells), insect cells (e.g., 519 cells), yeast cells and bacterial cells (e.g., *E coli* cells). In certain embodiments, the host cell is a mammalian cell (e.g., a CHO cell or a HEK293 cell).

In some embodiments, a host cell comprises or expresses a vector that encodes the $V_H$ domain or the $V_L$ domain, or the heavy chain or the light chain, of an anti-MBG mAb or a fragment thereof. In further embodiments, a host cell comprises or expresses a single vector that encodes the $V_H$ domain and the $V_L$ domain, or the heavy chain and the light chain, of an anti-MBG mAb or a fragment thereof. In other embodiments, the same host cell or separate host cells comprise(s) or express(es) a vector that encodes the $V_H$ domain or the heavy chain of an anti-MBG mAb or a fragment thereof, and a separate vector that encodes the $V_L$ domain or the light chain of the mAb or fragment thereof.

A vector can be transfected or introduced into a host cell by any method known in the art. Transfection agents and methods include without limitation calcium phosphate, cationic polymers (e.g., DEAE-dextran and polyethylenimine), dendrimers, fugene, cationic liposomes, electroporation, sonoporation, cell squeezing, gene gun, viral transfection and retroviral transduction.

Methods and conditions for culturing transfected host cells and recovering the recombinantly produced anti-MBG antibody or fragment thereof are known in the art, and may be varied or optimized depending on, e.g., the particular expression vector or/and host cell employed. In some embodiments, the $V_H$ domain or/and the $V_L$ domain, or the heavy chain or/and the light chain, of an anti-MBG mAb or a fragment thereof are recombinantly produced. In certain embodiments, the heavy chain and the light chain of an anti-MBG whole IgG1, IgG2 or IgG4, or the heavy chain and the light chain of an anti-MBG Fab fragment optionally fused with a protracting moiety, are recombinantly produced.

IX. Literature Cited

The following non-patent literature is cited herein:

Agunanne, E. et al., *Am. J. Perinatol.*, 28:509-514 (2011);
Asano, Y. et al., *Am. J. Pathol.*, 176:1983-1998 (2010);
Asano, Y. et al., *J. Dermatol. Sci.*, 59:153-162 (2010);
Bagrov, A. et al., *Cardiovas. Res.*, 25:371-377 (1991);
Bagrov, A. et al., *Eur. J. Pharmacol.*, 274:151-158 (1995);
Bagrov, A. et al., *Hypertension*, 26:781-788 (1995);
Bagrov, A. et al., *Hypertension*, 31:1097-1103 (1998);
Bagrov, Y. et al., *Front. Biosci.*, 10:2257-2262 (2005);
Bagrov, A. and Shapiro, J., *Nat. Clin. Pract. Nephrol.*, 4:378-392 (2008);
Bagrov, A. et al., *Pharmacol. Rev.*, 61:9-38 (2009);
Balint R F et al., *Gene* 137:57-62 (1993);
Blaustein, M., *Am. J. Physiol.*, 264:C1367-1387 (1993);
Chander, P. et al, *J. Am. Soc. Nephrol.*, 15:2391-2403 (2004);
Chappell, L. et al., *Biomark. Med.*, 8:455-458 (2014);
Czuwara-Ladykowska, J. et al., *J. Biol. Chem.*, 276:20839-20848 (2001);
Dinkova-Kostova, A. et al., *Proc. Natl. Acad. Sci. USA*, 102:4584-4589 (2005);
Ehrig, J. et al., *Placenta*, 35:932-936 (2014);
Ehrig, J. et al., *Placenta*, 36:1276-1282 (2015);
Elkareh, J. et al., *Hypertension*, 49:215-224 (2007);
Elkareh, J. et al., *Am. J. Physiol. Renal Physiol.*, 296:F1219-F1226 (2009);
Fedorova, L. et al., *Am. J. Physiol. Renal. Physiol.*, 296:F922-934 (2009);
Fridman, A. et al., *J. Hypertens.*, 20:1189-1194 (2002);
Gagliardini, E. and Benigni, A., *Cytokine Growth Factor Rev.*, 17:89-96 (2006);
Gillis, E. et al., Am. *J. Physiol. Regul. Integr. Comp. Physiol.*, 309:R62-70 (2015);
Graves, S., Hypertension, 10: I84-86 (1987);
Hagmann, H. et al., *Clin. Chem.*, 58:837-845 (2012);
Hertig, A. and Liere, P., *Clin. Chim. Acta*, 411:1591-1595 (2010);
Horvat, D. et al., *Hypertens. Pregnancy*, 29:1-9 (2010);
Ianosi-Irimie, M. et al., *Clin. Exp. Hypertens.*, 27:605-617 (2005);
Kaihura. C. et al., *Am. J. Physiol. Heart Circ. Physiol.*, 297:H759-H764 (2009);
Karihaloo, A., *Curr. Diab. Rep.*, 12:414-422 (2012);
Kato, S. et al., *Kidney Int.*, 56:1037-1048 (1999);
Kennedy, D. et al., *Hypertension*, 47:488-495 (2006);
Kitada, M. et al., *Int. J. Nephrol. Renovasc. Dis.*, 9:279-290 (2016);
Komiyama, Y. et al., *Clin. Biochem.*, 38:36-45 (2005);
Kubo, M. et al., *Am. J. Pathol.*, 163:571-581 (2003);
LaMarca, H. et al., *Placenta*, 27:984-988 (2006);
Lan, H., *Clin. Exp. Pharmacol. Physiol.*, 39:731-738 (2012);
Laragh, J. et al., *Fed. Proc.*, 41:2415-2423 (1982);
Leonard, D. et al., *J. Invest. Med.*, Vol. 62 No. 4 (2014), Combined Annual Meeting Abstracts;
Lim, A. and Tesch, G., *Mediators Inflamm.*, 2012:146154 (2012);
Lopatin, D. et al., *J. Hypertension*, 17:1179-1187 (1999);
Marchesi, C. et al., *Trends Pharmacol. Sci.*, 29:367-374 (2008);
Mason, R., *J. Cell Commun. Signal.*, 3:95-104 (2009);
Maynard, S. and Karumanchi, S., *Semin. Nephrol.*, 31:33e46 (2001);
Maynard, S. et al., *J. Clin. Invest.*, 111:649-658 (2003);
Nikitina, E. et al., *J. Hypertension*, 29:769-776 (2011);
Paci, A. et al., *Hypertens. Res.*, 23(Suppl.):S87-S91 (2000);
Puschett, J. et al., *Am. J. Kidney Dis.*, 56:359-370 (2010);
Puschett, J. et al., *Biochim. Biophys. Acta*, 1802:1246-1253 (2010);
Puschett, J., *Am. J. Perinatol.*, 29:777-785 (2012);
Qi, W. et al., *Int. J. Biochem. Cell Biol.*, 40:9-13 (2008);
Schwinger, R. et al., *Circulation*, 99:2105-2112 (1999);
Sugimoto, H. et al., *Diabetes*, 56:1825-1833 (2007);
Tian, J. et al., *Mol. Biol. Cell*, 17:317-326 (2006);
Tihtonen, K. et al., *J. Obstet. Gynecol. Reprod. Biol.*, 128: 180-186 (2006);
Uddin, M. et al., *J. Biol. Chem.*, 283:17946-17953 (2008);
Uddin, M. et al., *Placenta*, 29:266-273 (2008);
Uddin, M. et al., *Am. J. Nephrol.*, 30:26-33 (2009);
Uddin, M. et al., Am. *J. Physiol. Regul. Integr. Comp. Physiol.*, 296:1726e34 (2009);
Uddin, M. et al., *Hypertens. Pregnancy*, 31:70-78 (2012);
Uddin, M. et al., *Transl. Res.*, 160:99-113 (2012);
Venkatesha, S. et al., *Nat. Med.*, 12:642-649 (2006);
Verlohren, S. et al., *Am. J. Obstet. Gynecol.*, 206:58.e1-8 (2012);
Versari, D. et al., *Br. J. Pharmacol.*, 157:527-536 (2009);
von Dadelszen, P. and Magee, L., *Curr. Hypertens. Rep.*, 16:454 (2014);
Vu, H. et al., *Am. J. Nephrol.*, 25:520-528 (2005);
Wu, Y. and Zhou, B., *Cell Adh. Migr.*, 4:199-203 (2010);
Yuan, Z. et al., *Mol. Biol. Cell*, 16:4034-4045 (2005);
Zhang, M. et al., *Am. J. Physiol. Renal. Physiol.*, 302:F433-438 (2012); and
Zvartau, N. et al., *Cell Mol. Biol.* (Noisy-le-grand), 52:24-27 (2006).

All publications and patents cited in this specification are herein incorporated by reference as if each individual publication or patent were specifically and individually indicated to be incorporated by reference and are incorporated herein by reference to disclose and describe the methods and/or materials in connection with which the publications are cited.

The following examples are intended only to illustrate the disclosure. Other assays, studies, processes, protocols, procedures, methodologies, reagents and conditions may alternatively be used as appropriate.

EXAMPLES

Example 1. Creation of Chimeric Anti-MBG Antibodies

A chimeric antibody was created from a mouse antibody that binds to MBG with high specificity and high affinity. The $V_H$ domain and the $V_L$ domain of mouse antibody (SEQ ID NOs: 1 and 2) were fused to human IgG2 $C_H1$ $C_H2$ and $C_H3$ domains or a human kappa $C_L$ domain, respectively.

Example 2. Creation of Humanized Anti-MBG Antibodies

The mouse antibody that binds MBG was also humanized. The CDRs of the heavy chain (IgG1) and the light chain (kappa) of 3E9 (SEQ ID NOs: 3-8) were grafted to acceptor human framework sequences.

Human framework sequences were selected by aligning the mouse framework sequences with a database of human framework sequences to find the closest human homologs for each chain (generally about 65-70% sequence identity). Human VH4-31 and VH4-59 were most homologous to the mouse framework sequence for the heavy chain, and human VK2-29 and VK2-30 were most homologous to the mouse framework sequence for the light chain. VH4-59 and VK2-30 were selected as the acceptor human framework sequences for the $V_H$ and $V_L$ domains, respectively, because they have high usage in the human antibody repertoire and show high conservation at critical framework positions compared to other human framework sequences.

Three 3D models of the Fv region of a target antibody were built using the three combinations of the $V_H$ domain of 1T4K, 1ORS and 1DQD and the $V_L$ domain of 1TET. In the models, templates matched CDR lengths and canonical structures with those predicted from the 3E9 sequence. Amino acid positions in the framework regions that differed between the mouse and human sequences and may influence antigen binding were identified. Three humanized heavy chain variable sequences (H1, H2 and H3) and two humanized light chain variable sequences (L1 and L2) were designed. The humanized heavy chain and light chain variable sequences had a similarity to human germlines of about 87-94%. Humanized antibodies resulting from all six combinations of the three humanized heavy chains and two humanized light chains—H1L1, H2L1, H3L1, H1L2, H2L2 and H3L2—were created, with each heavy chain containing human IgG2 or IgG4 $C_H1$, $C_H2$ and $C_H3$ domains and each light chain containing a human kappa $C_L$ domain.

Example 3. Creation of Phage-Derived, Human Anti-MBG Antibodies

A human phagemid library with $1.2\times10^{10}$ independent clones was panned against MBG conjugated to bovine serum albumin (BSA). As the panning proceeded to the third round of enrichment for MBG-binding clones, phage were competitively eluted off antigen using first a "non-specific" cardiotonic steroid (CTS, typically ouabain at 1-10 μM free molecule), followed by a second competitive elution with MBG at a single concentration (1-5 For the fourth round of enrichment, the second elution was a series of stepped concentrations of free MBG (0.1, 0.5, 1.0 and 5.0 and clones from the final 5 μM elution were recovered for screening. Phages that remained on antigen after the final competitive elution were also recovered using triethylamine at 100 μM and were also screened for binders, which led to, e.g., the 236/237 antibody with a very high affinity and specificity for MBG.

Around 660 individual clones representing six different pan-enriched fractions were tested for binding to MBG in an enzyme-linked immunosorbent assay (ELISA), which identified several dozen MBG-specific clones. About 110 putative MBG-binding antibodies (Fab fragments expressed on phage) were further characterized by BstN1 fingerprinting, DNA sequencing or/and MBG competitive ELISA, resulting in 14 unique antibodies that bound to and competed with MBG in the ELISA. The relative CTS specificity of the 14 human antibodies is shown in Example 8 below. Seven of the 14 unique anti-MBG Fab fragments (201/202, 203/204, 205/207, 206/208, 236/237, 238/239 and 240/241) were converted into whole human IgG1 by subcloning the heavy chain variable domain and the complete light chain contained within each phage clone into a mammalian expression vector for expression in HEK293 cells. Some of the phage-derived, human anti-MBG Fab fragments and whole IgG1 antibodies had a kappa $C_L$ domain, while others had a lambda $C_L$ domain.

Example 4. Recombinant Production of Chimeric Anti-MBG Antibodies

To produce a chimeric 3E9 IgG mAb, the DNA sequences encoding the $V_H$ domain and the $V_L$ domain of mouse antibody were cloned using a RACE-PCR cDNA approach and were fused to a DNA sequence encoding human IgG2 $C_H1$, $C_H2$ and $C_H3$ domains or a human kappa $C_L$ domain, respectively, in separate expression plasmids that were similar to the expression plasmids used for humanized mAbs (see Example 6). The chimeric mAb was recombinantly produced using similar procedures as described for humanized mAbs in Example 6.

Example 5. Recombinant Production of Humanized Anti-MBG Antibodies

Plasmids encoding the humanized heavy chain H1, H2 or H3 fused to human IgG2 or IgG4 $C_H1$, $C_H2$ and $C_H3$ domains (see Example 2) and plasmids encoding the humanized light chain L1 or L2 fused to a human kappa $C_L$ domain (see Example 2) were prepared. HEK293F cells (Invitrogen) were cultured in serum-free medium and were co-transfected with a plasmid encoding H1, H2 or H3 and a plasmid encoding L1 or L2 (six different combinations to produce H1L1, H2L1, H3L1, H1L2, H2L2 and H3L2). On day 4 post-transfection, cell culture supernatants were harvested. Antibody was purified by Protein A affinity chromatography.

CHO cells are co-transfected with separate plasmids encoding the heavy chain (e.g., H1, H2 or H3) and the light chain (e.g., L1 or L2) of the humanized anti-MBG mAb (e.g., H1L1, H2L1, H3L1, H1L2, H2L2, H3L2) are grown in serum-free media and selected with 10 μg/ml of Puromycin and 500 µg/ml of G418 for 2 weeks. Single cells of the stable pool are sorted into 96-well plates by FACS. The colonies grow up after 2-3 weeks. The antibody levels in the culture media are screened by Elisa. The clones of high antibody expression are expanded to 24-well plates, 6-well plates, and 30 ml shaking cultures. Antibody production levels are characterized in batch cultures. The antibody production levels of the top clones were >300 mg/L.

Example 6. Recombinant Production of Human Anti-MBG Antibodies

HEK293F cells co-transfected with separate plasmids encoding the heavy chain and the light chain of a human anti-MBG mAb (e.g., 201/202, 206/208, 236/237 or 2A-F8) were grown in serum-free medium for 4 days in 200 mL cultures. Culture supernatant was harvested and filter-sterilized. The antibodies were purified by Protein A affinity chromatography.

CHO cells are co-transfected with separate plasmids encoding the heavy chain and the light chain of the human anti-MBG mAb (e.g., 201/202, 206/208, 236/237 or 2A-F8) and are grown in serum-free media and selected with 10 µg/ml of Puromycin and 500 µg/ml of G418 for 2 weeks. Single cells of the stable pool are sorted into 96-well plates by FACS. The colonies are grown for 2-3 weeks. The antibody levels in the culture media are screened by Elisa. The clones of high antibody expression are expanded to 24-well plates, 6-well plates, and 30 ml shaking cultures. Antibody production levels are characterized in batch cultures. The antibody production levels of the top clones are >300 mg/L.

Example 7. Antigen Binding of Humanized Anti-MBG

Figure 1B:
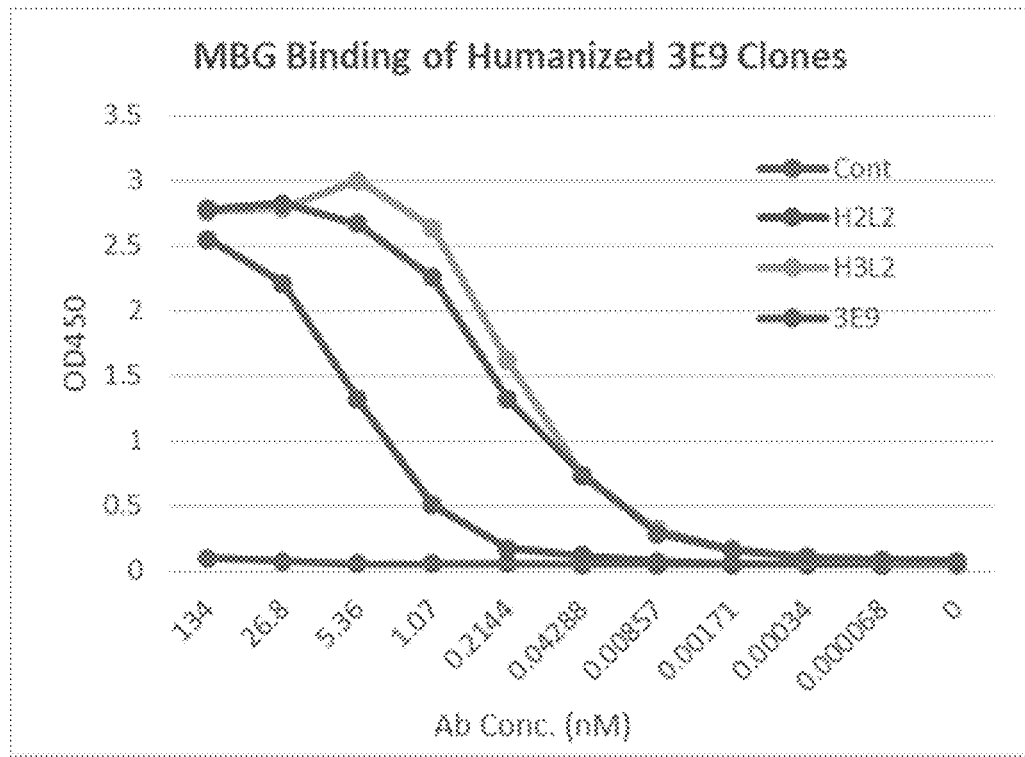

The antigen binding of humanized anti-MGB was assayed in a direct Elisa assay. 2 µg/ml of MBG-conjugated BSA was coated in the Elisa plate. After blocking with 1% BSA, 2-fold dilution series of humanized anti-MBG was added to the plate. After washing, the bound antibody was detected by adding anti-human Fc HRP conjugate, and quantified by adding the TMB substrate. OD absorption at 450 nm was measured in a microplate reader. Among the 6 humanized antibodies, H3L2 exhibited the highest binding affinity (FIG. 1a) which is similar to the parent 3E9 antibody (FIG. 1b)

Example 8. Avidity and Relative CTS Specificity of Anti-MBG Antibodies

The avidity of anti-MBG antibodies for MBG was estimated in an ELISA. Wells of a microtiter plate were coated with 2 µg/ml of either MBG-bovine serum albumin (BSA) or MBG-keyhole limpet hemocyanin (KLH). The wells were then blocked with 1% BSA. A test IgG antibody at varying concentrations (typically from about 0.0001 nM to about 25 nM) was added to the wells. The test IgG bound to immobilized MBG was detected with an anti-human Fc, horseradish peroxidase (HRP)-conjugated secondary antibody (Jackson ImmunoResearch). After washing of the wells, an appropriate HRP reagent (e.g., TMB ultra, Thermo Fisher) was added to the wells. Optical density (OD) at 450 nm was measured by a microplate reader. The concentration of test antibody at the midpoint of the binding curve is an estimate of avidity for MBG.

TABLE 1

Estimated avidity ($K_d$) of anti-MBG antibodies (antibody concentration at 50% maximal binding to antigen, or $EC_{50}$)

| Antibody (Plasmid) | Antigen 1 (MBG-BSA) | Antigen 2 (MBG-KLH) |
|---|---|---|
| 201/202 | 0.33 nM | 0.20 nM |
| 203/204 | 0.32 nM | 0.20 nM |
| 206/208 | 1.35 nM | 0.20 nM |
| 236/237 | 0.12 nM | 0.14 nM |
| 240/241 | 0.22 nM | 0.30 nM |
| H3L2 | 0.6 nM | 1.5 nM |

The specificity (relative affinity) of anti-MBG antibodies for MBG relative to various cardiotonic steroids (CTSs) was determined in a competitive ELISA. Each anti-MBG antibody was tested for its binding to immobilized MBG in the presence of free MBG, resibufogenin (RBG), cinobufagin (CINO), ouabain (OUB) or digoxin (DIG) as a competitor. A constant amount of an anti-MBG antibody (typically 1-5 µg/mL) and varying concentrations of each CTS (from $10^{-12}$M to $10^{-5}$M) were pre-incubated before being added to the MBG-BSA-coated wells. After washing of the wells, an anti-human Fc, HRP-conjugated secondary antibody (at 1:5000 dilution) was added to the wells and incubated at 37° C. for 1 hr. After washing of the wells, an appropriate HRP reagent (e.g., TMB ultra, Thermo Fisher) was added to the wells. OD at 450 nm was measured by a microplate reader. MBG at 10 µM was assumed to be 100% competed, and MBG at 1 pM was assumed to be 0% competed. The data was plotted as a titration of antibody-antigen binding relative to free CTS concentration in the competition reaction to determine the free CTS concentration (µM) giving 50% maximal binding of antibody to immobilized MBG. The relative specificity of an antibody for a CTS was normalized to MBG=100%.

TABLE 2

Relative specificity of anti-MBG antibodies for free CTSs in competition with immobilized MBG (normalized to MBG = 100%), where the free CTS concentration (µM) giving 50% maximal binding of antibody to MBG-BSA was determined

| Antibody (Plasmid or Clone) | Form | Rel. CTS Specificity as % of MBG Binding | | | | |
|---|---|---|---|---|---|---|
| | | MBG | RBG | CINO | OUB | DIG |
| 201/202 | IgG1 | 100 | 50 | 20 | 0 | 0 |
| 203/204 | IgG1 | 100 | 10 | 0 | 0 | 0 |
| 205/207 | Fab | 100 | nt | 0 | 0 | 0 |
| 206/208 | IgG1 | 100 | 20 | 0 | 0 | 0 |
| 236/237* | IgG1 | 100 | 0 | 0 | 0 | 0 |
| 238/239* | Fab | 100 | nt | nt | 10 | nt |
| 240/241* | IgG1 | 100 | nc | nc | nc | nc |
| R4CE-1E (I-2) | Fab | 100 | 12.5 | 4 | 0 | 0 |
| R4CE-7G (II-4) | Fab | nt | nt | nt | nt | nt |
| R4CE-10H (III-3) | Fab | 100 | nt | nt | nt | nt |
| 1B-6C | Fab | 100 | nt | nt | nc | nt |
| 1B-6E | Fab | 100 | nt | nt | 2 | nt |
| 2A-5A | Fab | 100 | 10 | 2.5 | 0 | 2.5 |
| 2A-F8 | Fab | 100 | 0 | 0 | 0 | 0 |
| H3L2 | IgG2 | 100 | 0 | 0 | 0 | 0 |

*10 µM of free CTS was insufficient to see the free CTS concentration giving 50% maximal binding of the antibody to MBG-BSA. When 236/237 was tested for competition with 100 µM free MBG or RBG, a complete binding curve was generated. 238/239 and 240/241 were not tested at 100 µM free CTS.
nc = not calculable from competition assay/chart
nt = not tested Three antibodies, 236/237, 2A-F8, and H3L2, did not react with any of the CTS competitor molecules. Two antibodies, 201/202 and R4CE-1E, reacted with the CTS competitors RBG and CINO. Two antibodies, 203/204 and 206/208, reacted with CTS competitor RBG. One antibody, 2A-5A, reacted with the CTS competitors RBG, CINO and DIG. Two antibodies, 238/239 and 1B-6E, reacted with the CTS competitor OUB (but were not tested against the other CTS competitors).

Example 9. Inhibition of MBG-Induced PKC-45 Nuclear Translocation by Anti-MBG Abs MBG induces fibrosis, including renal fibrosis, cardiac fibrosis and vascular fibrosis (Federova 2009, Elkareh 2007 and Nikitina 2011). MBG binding to NKA induces translocation of PKC-δ from the cytosol to the nucleus, where it phosphorylates the transcription factor Fli-1 and thereby renders Fli-1 prone to proteolysis. Proteolysis of Fli-1 releases its suppression of expression of procollagens I and III (Elkareh 2009). Increased collagen synthesis promotes fibrosis.

MBG was incubated with an anti-MBG antibody prior to addition to cultured primary rat cardiac fibroblasts. Nuclei were isolated 30 min later and analyzed for amount of PKC-6. The mouse anti-MBG mAb 3E9 served as a positive control, and a non-MBG binding human IgG mAb served as a negative and isotype control.

Figure 2A:
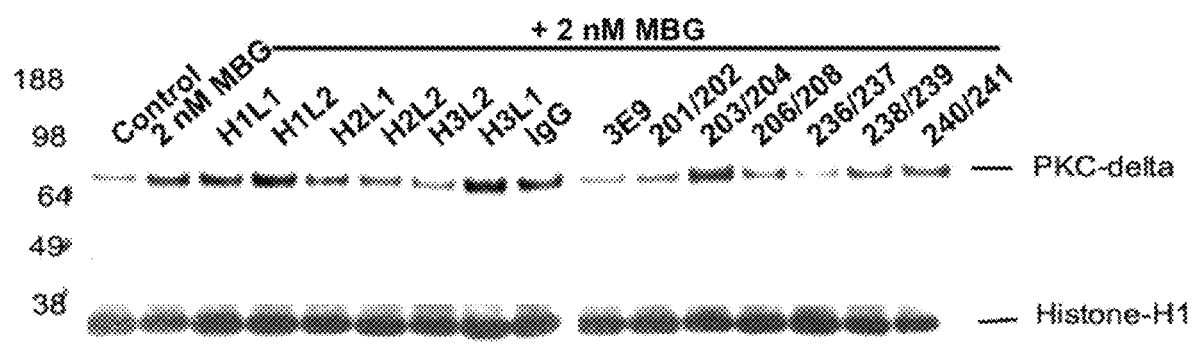
FIG. 2a is a Western blot showing the relative amount of protein kinase C-delta (PKC-δ, 78 kDa) in the nucleus of primary cardiac fibroblasts incubated with MBG alone (2 nM) or with MGB (2 nM) plus an anti-MBG antibody.
Figure 2B:
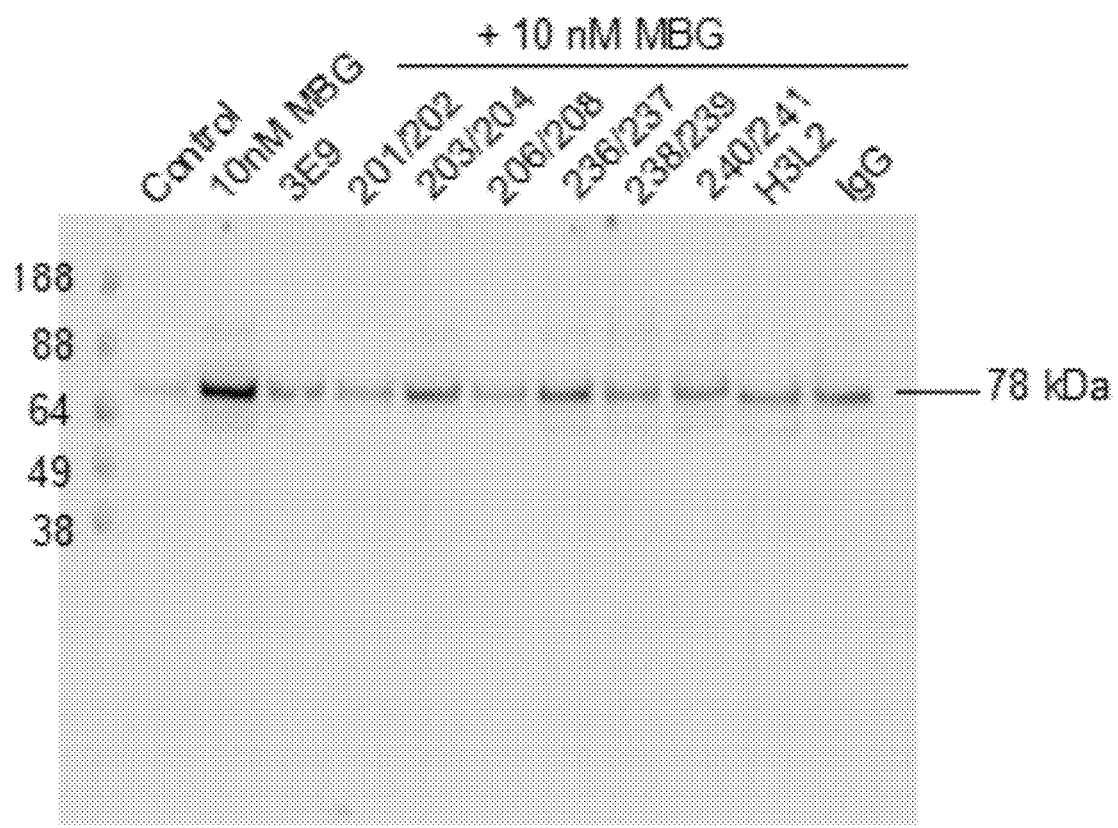
FIG. 2b is a Western blot showing the relative amount of protein kinase C-delta (PKC-δ, 78 kDa) in the nucleus of primary cardiac fibroblasts incubated with MBG (10 nM) or with MBG (10 nM) plus an anti-MBG antibody.

FIG. 2 is a Western blot showing the relative amount of PKC-δ (78 kDa) in the nucleus of primary cardiac fibroblasts incubated with MBG alone or with MBG plus an antibody. MBG at 2 nM induced an increase in the amount of PKC-δ in the nucleus compared to "Control" (treatment with only vehicle, lane 1 in the blot), which was reduced by treatment with the anti-MBG mAbs 3E9, H3L1, 201/202, 206/208 and 236/237, and to a lesser extent by H2L1, H2L2, 238/239 and 240/241 (FIG. 2a). The Western blot in FIG. 2b shows that the humanized 3E9 mAb H3L2 and all six phage-derived, human mAbs (two numbers with a slash) reduced PKC-δ translocation into the nucleus at 10 nM MBG.

Example 10. Reversal of MBG Inhibition of HUVEC Cell Proliferation by Anti-MBG Abs Endothelial dysfunction causes pathological features of pre-eclampsia, including increased vascular permeability/leakage (Puschett, *BBA* 2010). MBG promotes endothelial dysfunction in part by inhibiting endothelial cell proliferation (Uddin, *Placenta* 2008).

Figure 3A:
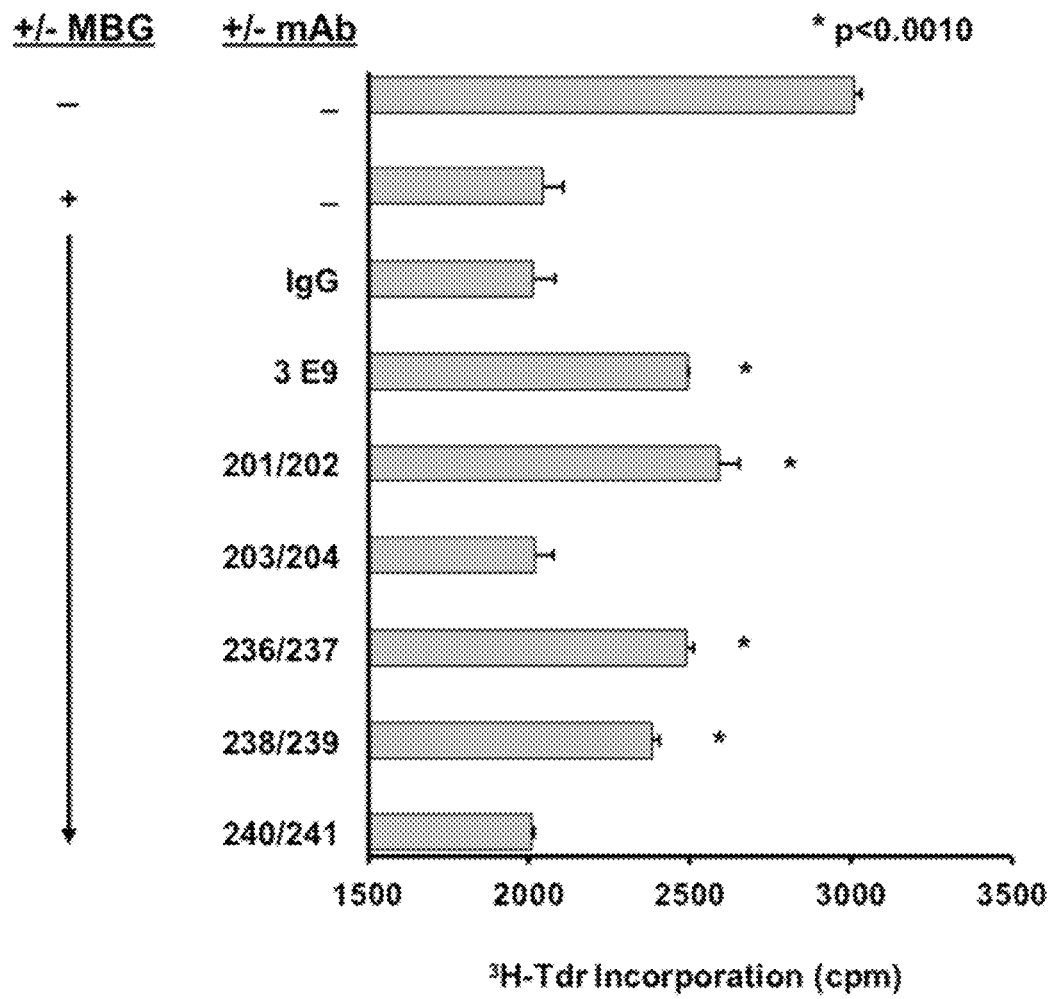
FIG. 3a shows the level of proliferation of human umbilical cord venous endothelial cells (HUVEC) incubated with MBG alone (2 nM) or with MBG (2 nM) plus a human anti-MBG antibody (20 µg/mL).
Figure 3B:
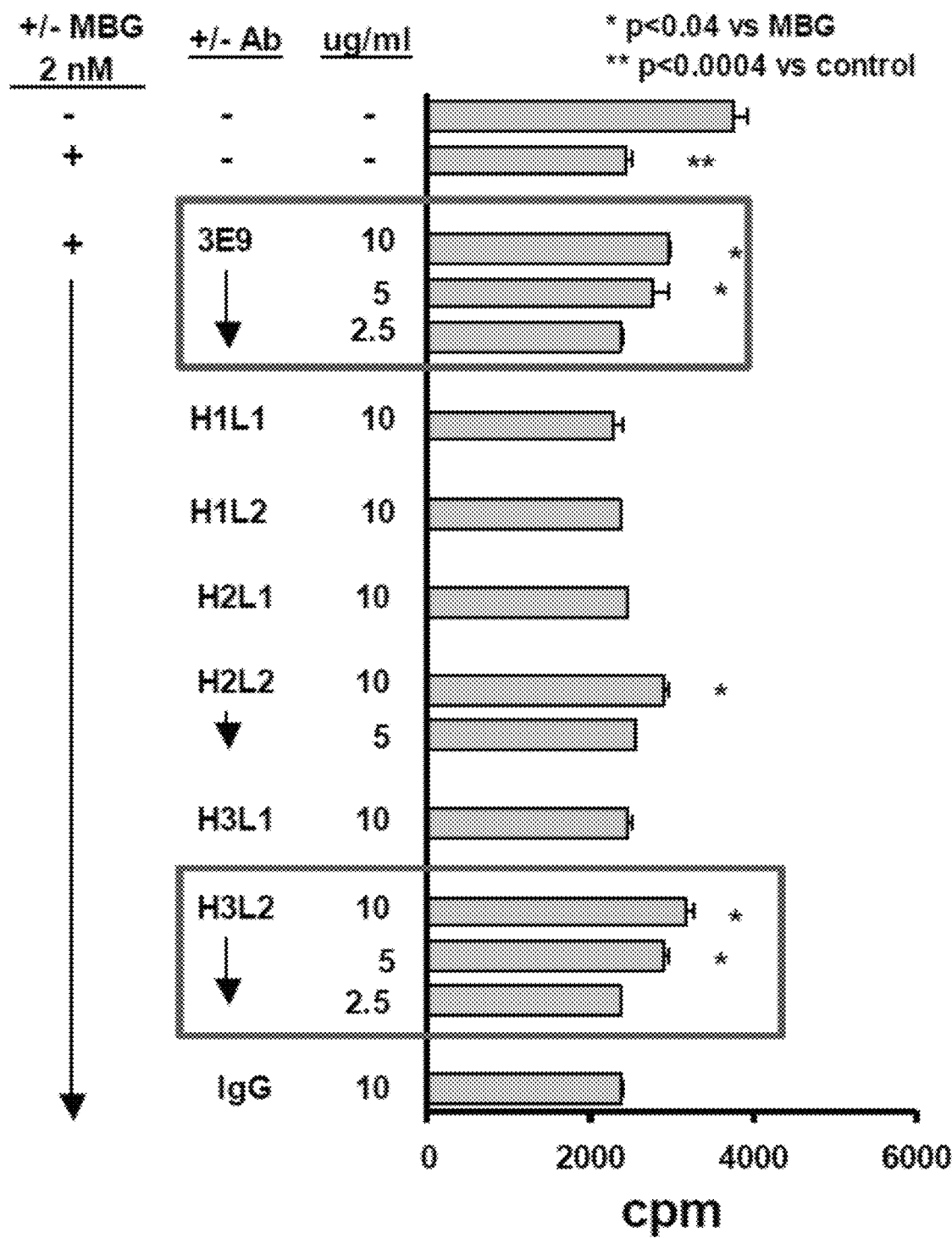
FIG. 3b shows the level of proliferation of human umbilical cord venous endothelial cells (HUVEC) incubated with MBG alone, or MBG (2 nM) plus a humanized anti-MBG antibody (2.5-10 µg/mL).

MBG (2 nM) was incubated with an antibody (20 µg/mL in FIG. 3a with human anti-MBG mAbs, or varying concentrations (2.5-10 µg/mL) in FIG. 3b with humanized anti-MBG mAbs) prior to addition to cultured human umbilical cord venous endothelial cells (HUVEC). After 48 hr, DNA synthesis was assessed by incorporation of $^3$H-thymidine.

HUVEC cells in endothelial cell growth medium were plated onto 96-well plates. The next day, the cells were pretreated with various antibodies (2.5-20 µg/mL) and then incubated with 2 nM MBG for 48 hr. [$^3$H]-Thymidine was added to each well. [$^3$H]-Thymidine-labeled DNA was assayed by harvesting the cells and assaying for $^3$H using a PerkinElmer Wallac Tailux liquid scintillation counter. The mouse anti-MBG mAb served as a positive control, and a non-MBG binding human IgG mAb served as a negative and isotype control. Means were tested for significance using Student's t-test.

MBG inhibition of HUVEC cell proliferation was significantly reduced by 201/202, 236/237 and 238/239 among the phage-derived human mAbs (FIG. 3a), and by H2L2 and H3L2 among the humanized 3E9 mAbs (FIG. 3b).

Example 11. Reversal of MBG-Induced Anti-Proliferative and Anti-Angiogenic Signaling in CTB Cells by Anti-MBG Antibodies MBG inhibits proliferation, migration and invasion of cytotrophoblast (CTB) cells (Uddin, *JBC* and *Placenta* 2008). Furthermore, angiogenic imbalance induced by MBG promotes endothelial dysfunction in pre-eclampsia (Puschett, *BBA* 2010 and Uddin, T R 2012). In PE patients, sFlt1 and sEng levels are increased prior to clinical symptoms and also correlate with PE severity, whereas P1GF level is significantly reduced (Verlohren 2012 and Hagmann 2012). MBG induces anti-angiogenic signaling in CTB cells (Ehrig 2014).

CTB cells were serum-starved in medium and then washed twice, and replicates were subsequently treated with media (to stimulate cell proliferation) containing DMSO (vehicle) or 0.1, 1, 10 or 100 nM of MBG for 48 hr. Some cells were pre-treated with a 30% molar excess of the antibody 206/208, H1L2 or 3E9 prior to addition of MBG. The culture medium was collected for analysis of pro-angiogenic and anti-angiogenic factors. Cell viability was measured using a CellTiter Assay (Promega; Uddin, *JBC* 2008 and *Placenta* 2008).

In a further series of experiments, human CTB cells were treated with DMSO (vehicle) or 0.1, 1, 10 or 100 nM of MBG for 48 hr. Some cells were pre-treated with a 30% molar excess of the antibody 201/202, 206/208, 236/237, H1L2 or 3E9, while other cells were co-treated with the antibody and MBG. The mouse anti-MBG mAb served as a positive control, and a non-MBG binding human IgG mAb served as a negative and isotype control. The culture medium was collected for analysis of secretion of pro-angiogenic and anti-angiogenic factors. The levels of soluble fms-like tyrosine kinase 1 (sFlt1 or sVEGFR1), soluble endoglin (sEng), vascular endothelial growth factor (VEGF), and placental growth factor (P1GF) in the culture medium were measured using ELISA kits (Boster Biotech, Pleasanton, Calif.). Cell lysates were analyzed for expression of proliferating cell nuclear antigen (PCNA) and phosphorylation of p38 MAPK by Western blot. Cell viability was measured using a CellTiter Assay (Promega). Statistical analysis was performed using analysis of variance and Duncan's post hoc test. A p value ≤0.05 was considered statistically significant.

Compared to treatment with vehicle (DMSO), treatment of CTB cells with ≥1 nM MBG significantly downregulated PCNA expression and increased phosphorylation of p38 MAPK, significantly increased secretion of the anti-angiogenic factors sFlt1 and sEng, and significantly reduced secretion of the pro-angiogenic factors VEGF and P1GF (p<0.05 for each). Both pre-treatment and co-treatment of CTB cells with each of the four test anti-MBG mAbs and mouse antibody significantly upregulated PCNA expression and reduced phosphorylation of p38 MAPK, significantly reduced secretion of sFlt1 and sEng, and significantly increased secretion of VEGF and P1GF (p<0.05 for each). All four test anti-MBG mAbs attenuated MBG-induced anti-proliferative and anti-angiogenic signaling in cultured CTB cells to a similar extent as the murine anti-MBG mAb 3E9.

Example 12. DOCA/Saline Rat Model of Pre-Eclampsia (PE)

Humans gain about 40-50% in extracellular fluid (ECF) volume during pregnancy, and volume expansion promotes MBG secretion and ultimately development of PE (Maynard 2001). In a volume-expansion model of PE in pregnant rats (Vu 2005 and Puschett, BBA 2010), substitution of saline for normal drinking water along with injections of the aldosterone precursor desoxycorticosterone acetate (DOCA) induce volume expansion, elevated urine MBG level and caused a syndrome with many of the phenotypic characteristics of human PE: hypertension, proteinuria, IUGR, reduced pup number, and reduced total litter weight (Vu 2005, Ianosi-Irimie 2005, and Horvat 2010).

Female Sprague-Dawley rats (200-250 g, Charles River Laboratories) were acclimatized for 1 week, and mated with male Sprague-Dawley rats (275-300 g). Pregnancy was confirmed by the presence of vaginal plugs or by examination of vaginal smears. Each rat was housed separately.

Five groups of rats were studied (n=10 per group): Group 1 (NP): normal pregnant rats; Group 2 (PDS): pregnant rats injected i.p. initially with 12.5 mg of DOCA in a depot form, followed by a weekly i.p. injection of 6.5 mg of DOCA, and whose drinking water is replaced with 0.9% saline; Group 3 (NPM): Normal pregnant rats given daily injections of MBG (7.65 μg per kg body weight per day) once pregnancy was established on day four of the experiment; Group 4 (PDS-3E9): rats administered DOCA and saline as for Group 2, and also given the murine anti-MBG antibody 3E9 (2.2 mg per kg body weight per day) on days 16, 17, and 18 of pregnancy; and Group 5 (PDS-H3L2): rats administered DOCA and saline as for Group 2, and also given the humanized anti-MBG antibody H3L2 (2.2 mg per kg body weight per day) on days 16, 17, and 18 of pregnancy.

Systolic blood pressure (BP) was measured by tail cuff at days 17-19. At least 3 readings are taken after BP has stabilized, and the mean of these values was calculated. The reported BP values are the mean of the daily measurements. At 18-20 days of pregnancy, 24-hour urine was collected in the absence of food to avoid contamination of the measurement of the protein amount in urine by any fallen food particles. Each rat was housed separately in a metabolic cage during this portion of the study. The 24-hour protein excretion was measured and was normalized to creatinine. The rats were sacrificed after the last measurement on days 18-20, and blood samples were taken. The number of fetal pups was counted and examined. The mean number of pups and any developmental or histological abnormalities in the pups were assessed. Statistical analysis was performed using analysis of variance and Tukey's post hoc test. A p value ≤0.05 was considered statistically significant.

TABLE 1

MBG causes, and anti-MBG normalizes, preeclampsia symptoms in a rat model.

| Groups | Blood Pressure-Initial (mm Hg) * | Blood Pressure-Final (mm Hg) * | Urine Protein (mg/ 24 h) ** | No. Pups | % Malformed Pups |
|---|---|---|---|---|---|
| NP | 103 ± 5 | 98 ± 7 | 2.8 ± 1.1 | 14 ± 1.8 | 0 |
| PDS | 101 ± 8 | 141 ± 9 * | 5.7 ± 1.6 * | 10.2 ± 1.5 * | 16 * |
| NPM | 104 ± 4 | 137 ± 5 * | 6.4 ± 1.8 * | 9.5 ± 1.3 * | 18 * |
| PDS-3E9 | 102 ± 8 | 100.8 ± 8 | 3.1 ± 0.9 | 13.6 ± 2.1 | 0 |
| PDS-H3L2 | 104 ± 5 | 109.4 ± 11 | 3.5 ± 0.7 | 12.9 ± 3.2 | 0 |

NP: normal pregnant
PDS: NP + saline drinking water (DOCA model of preE)
NPM: NP + MBG (Normal pregnant rats given daily injections of MBG (7.65 μg/kg/d) once pregnancy was established on day four of the experiment.)
PDS-3E9: PDS + anti-MBG murine antibody (provided by PRI) (PDS rats injected i.p. with anti-MBG antibody 3E9, 2.2 mg/kg/d; on the 16th, 17th, and 18th days of pregnancy.)
PDS-H3L2: PDS + anti-MBG humanized antibody (provided by PRI) (PDS rats injected i.p. with anti-MBG antibody H3L2, 2.2 mg/kg/d; on the 16th, 17th, and 18th days of pregnancy.)
N = 10 for all treatment groups.
PDS-MAB: PDS rats receiving either anti-MBG antibody.
The final (17-19 d of gestation) BP of PDS and NPM rats was higher compared to initial BP. However, there was no BP change in NP and PDS-MAB rats. The 24 h urinary protein was significantly higher in PDS and NPM rats compared to NP and PDS-MAB. Number of pups decreased in PDS and NPM rats. The percentage of malformed pups was higher in PDS and NPM rats; however, there were no malformed pups in NP or PDS-MAB rats (* p < 0.05).
Either administration of exogenous MBG or saline drinking water results in significant increases in blood pressure (BP) and urinary protein, together with a reduction in litter size and an increase in malformed pups. Anti-MBG antibody rescues the normal phenotype in pregnant rats on saline water.
* Blood pressure measured by tail cuff.
** Urine protein normalized to creatinine.

DOCA and saline treatment increased blood pressure, proteinuria, an overall reduction in litter size, and fetal malformations in pregnant rats. The administration of MBG alone had similar effects. Anti-MBG and humanized anti-MBG antibody prevented this increase in blood pressure, proteinuria, and fetal malformations.

Example 13. Dahl Salt-Sensitive Rat Model of Pre-Eclampsia

Dahl salt-sensitive (Dahl-S) rats spontaneously exhibit during pregnancy many phenotypes characteristic of human PE, including hypertension, severe exacerbation of proteinuria, renal changes such as glomerulomegaly, increased fetal demise, and reduced size of newborns (Gillis 2015). Pregnant Dahl-S rats also have elevated MBG levels.

Female Dahl-S rats (SS/jr, 200-250 g, Charles River) are acclimatized for 1 week, and mated with male Dahl-S rats (275-300 g). Pregnancy is confirmed by the presence of vaginal plugs or by examination of vaginal smears. Each rat is housed separately.

Six groups of rats are studied (n=10 per group): Group 1: non-pregnant female Dahl-S rats; Group 2: pregnant Dahl-S rats; Group 3: pregnant Dahl-S rats given a non-MBG binding human mAb (IgG) as an isotype and negative control intraperitoneally (i.p.) twice weekly from day 10 through day 20 of pregnancy; Group 4: pregnant Dahl-S rats given an anti-MBG antibody (e.g., H3L2, 236/237 or 2A-F8) i.p. twice weekly from day 10 through day 20 of pregnancy; Group 5: as for Group 4, but given 2 mg/kg of the anti-MBG antibody i.p. twice weekly from day 10 through day 20 of pregnancy; and Group 6: as for Group 4, but given 0.5 mg/kg of the anti-MBG antibody i.p. twice weekly from day 10 through day 20 of pregnancy.

Systolic blood pressure is measured and calculated, the amount of protein in urine in a 24-hour period at 18-20 days of pregnancy is measured, and other measurements and evaluations are made similarly as described above for DOCA/saline rats. Statistical analysis is performed using analysis of variance and Tukey's post hoc test, with a p value ≤0.05 indicating statistical significance.

Systolic blood pressure (BP) is measured at day 0 (baseline, T0), days 8-10 (T1), and days 18-20 (T2). On each day, at least 3 readings are taken after BP has stabilized, and the mean of these values is calculated. The reported BP values for T0, T1 and T2 are the mean of the daily measurements.

At 18-20 days of pregnancy, 24-hour urine is collected in the absence of food to avoid contamination of the measurement of the protein amount in urine by any fallen food particles. Each rat is housed separately in a metabolic cage during this portion of the study. The levels of MBG, RBG and TCB in urine are measured in a competitive ELISA, and 24-hour protein excretion is measured. The rats are sacrificed on days 18-20, and blood samples are taken. Pups are counted and examined. The mean number of pups and any developmental or histological abnormalities in the pups are assessed.

Statistical analysis is performed using analysis of variance and Tukey's post hoc test. A p value ≤0.05 is considered statistically significant.

Example 14. STZ-CD1 Mouse Model of Advanced Diabetic Nephropathy

A single i.p. injection of streptozotocin (STZ) (200 mg/kg) into CD1 mice induces type 1 diabetes (T1D) as a result of STZ's toxicity to insulin-producing pancreatic β-cells. STZ-CD1 T1D mice develop chronic renal disease associated with tubulointerstitial fibrosis and decreased renal function within 6 months after STZ injection (Sugimoto 2007). STZ-CD1 mice display severe tubulointerstitial fibrosis, moderate mesangial matrix expansion, and moderate albuminuria (Kitada 2016).

CD1 mice (7 weeks old, Charles River) at 8 weeks of age are injected i.p. with vehicle or STZ (in 10 mM sodium citrate, pH 4.5, 200 mg/kg) to induce T1D. At 3 days after STZ injection, T1D is confirmed by a urine dipstick test. Each mouse is housed separately in a metabolic cage. Mice are randomly divided into 6 groups (n=12 per group) and treated, beginning at 1 month after STZ injection, i.p. twice weekly for 2 months as follows: Group 1: CD1 mice+ vehicle only; Group 2: STZ-CD1 T1D mice+normal human IgG (10 mg/kg) as a negative and isotype control; Group 3: STZ-CD1 T1D mice+murine anti-MBG mAb 3E9 as a positive control; Group 4: STZ-CD1 T1D mice+a test anti-MBG antibody (e.g., H3L2, 236/237 or 2A-F8) (1 mg/kg); Group 5: STZ-CD1 T1D mice+the test anti-MBG antibody; and Group 6: STZ-CD1 T1D mice+the test anti-MBG antibody. Mice are sacrificed 3 months after STZ injection.

Regarding assessment of clinical parameters, systolic blood pressure by tail plethysmography is monitored weekly. 24-hour urine samples are collected during the last week of treatment. Urine albumin is measured by ELISA (Exocell, Philadelphia, Pa.). Serum or urine creatinine is measured by high-pressure liquid chromatography (HPLC). Creatinine is quantitated by comparison to a standard curve of pure creatinine (10-50 ng).

For histopathological analysis, perfused kidneys are removed and fixed overnight in formalin, and sections are stained with periodic acid-Schiff. Slides are analyzed to evaluate the degree of glomerular expansion and sclerosis. Each glomerulus on a single section is graded from 0 to 4, where 0 represents no lesion, and 1, 2, 3 and 4 represent mesangial matrix expansion or sclerosis involving <25, 25-50, 50-75 or >75% of the glomerular tuft area, respectively. Tubulointerstitial fibrosis is evaluated using the picrosirius stain as described by Zhang et al. (2012).

For immunohistology, pro-fibrotic mediators (e.g., TGF-β and CTGF) and pro-inflammatory cytokines (e.g., TNF-α, IL-6 and MCP-1) in the kidney are detected on cryostat sections stained by indirect immunofluorescence and semi-quantitated as described by Kato et al. (1999).

Statistical analysis is performed using Student's t-test. A p value ≤0.05 is considered statistically significant.

Example 15. ZDF Rat Model of Advanced Diabetic Nephropathy

The Zucker diabetic fatty (ZDF, $Lepr^{fa}$/Crl) rat is a spontaneous model of DN. The ZDF rat, which is derived from the ZF strain, exhibits obesity with diabetes and is widely used to study type 2 diabetes (T2D). ZDF rats develop progressive insulin resistance and glucose intolerance at 3-8 weeks of age and become overtly diabetic at 8-10 weeks. Although ZDF rats do not exhibit glomerulosclerosis, tubular cell damage or tubulointerstitial fibrosis at 8 weeks, the glomeruli of ZDF rats appear slightly hypertrophic at 8 weeks compared with those of control lean rats. ZDF rats exhibit a further increase in glomerular lesions after 8 weeks of age, and moderate to severe mesangial matrix expansion at 22 weeks. Furthermore, tubular cell damage, moderate to severe tubulointerstitial fibrosis, inflammation and hypoxia are observed in the kidneys of ZDF rats at 22-39 weeks. ZDF rats develop moderate to severe mesangial matrix expansion, moderate to severe tubulointerstitial fibrosis, and moderate to severe albuminuria (Kitada 2016).

Male ZDF rats (10 weeks old, Charles River) and male lean (ZL) control rats (10 weeks old, Charles River) are housed separately in a metabolic cage. Beginning at 15 weeks, the rats are monitored for elevation of blood glucose level under fasting conditions. Diabetes is defined as a blood glucose level >250 mg/dL. Albuminuria is measured by ELISA (Exocell). Only hyperglycemic rats with significant albuminuria are placed in treatment groups and treated. Significant kidney pathology in ZDF rats is expected to be evident by 22 weeks of age (Chander 2004).

Rats are randomly divided into 6 groups (n=5 per group) and treated i.p. twice weekly after the onset of diabetes as follows: Group 1: ZL rats+vehicle only; Group 2: ZDF diabetic rats+normal human IgG as a negative and isotype control; Group 3: ZDF diabetic mice+murine anti-MBG mAb 3E9 (10 mg/kg) as a positive control; Group 4: ZDF diabetic mice+a test anti-MBG antibody (e.g., H3L2, 236/237 or 2A-F8) (1 mg/kg); Group 5: ZDF diabetic mice+the test anti-MBG antibody; and Group 6: ZDF diabetic mice+ the test anti-MBG antibody. Rats are sacrificed when they show signs of morbidity or are 39 weeks of age.

Assessment of clinical parameters, histopathological analysis, immunohistology and statistical analysis are performed similarly as described above for the STZ-CD1 mouse model of DN.

Example 16. Anti-MBG Antibodies Prevent MBG Inhibition of $Na^+K^+$-ATPase $Na^+K^+$-ATPase (NKA) was purified from rat heart. The NKA was collected as the sarcolemmal/particulate (SLP) fraction and frozen.

$Na^+K^+$-ATPase activity was measured as follows: aliquots of SLP were mixed with Reaction Buffer (200 mM Tris-HCl, pH 7.5, 200 mM NaCL, 30 mM $MgCl_2$, 60 mM KCl, 10 mM EGTA, 100 µg/mL PMSF, 2 µg/mL pepstatin A, and 2 µg/mL aprotinin). Reactions were performed with or without MBG and with or without anti-MBG antibodies (1-100 μg/mL). Ouabain was used as positive control for NKA inhibition. Tubes were prewarmed, and ATP was added. Reactions were stopped and were placed on ice.

Figure 4:
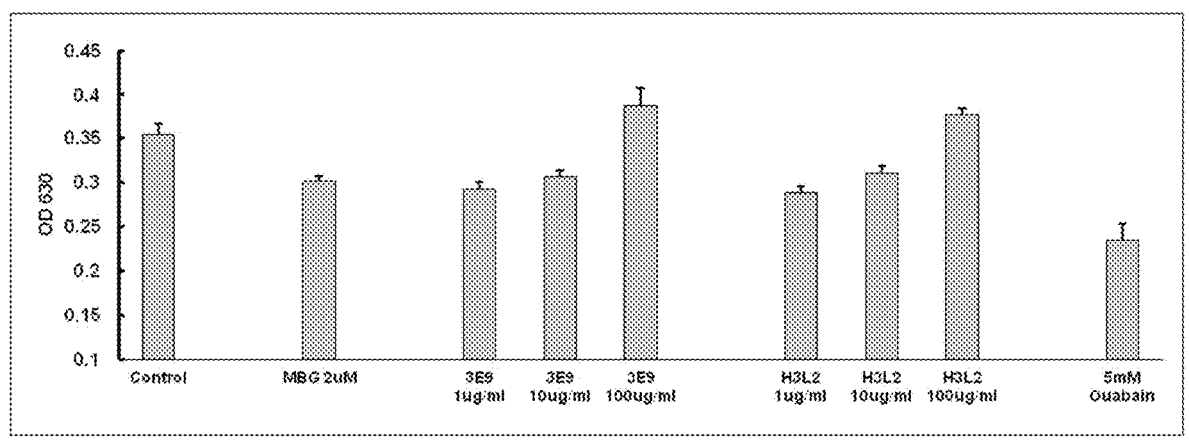
FIG. 4 shows $OD_{630}$ readings as a measurement of Pi which is a measure of $Na^+K^+$-ATPase activity. The bar graphs show the effect of MBG on Pi levels, and the reversal of this effect by anti-MBG antibodies.

Phosphate was assayed using the Malachite Green Phosphate Assay. Phosphate standard or sample was added to each well of a 96-well plate, followed by Reagent A. Reagent B was added, with mixing and incubation. OD was then read at 630 nm in a microplate spectrophotometer. Ouabain or MBG were able to inhibit the NKA activity significantly. The anti-MGB mouse antibody 3E9 and the humanized antibody H3L2 were found to reduce the inhibitory effect of MBG on NKA (FIG. 4).

Example 17: Measurement of MBG in a Biological Sample

Figure 5:
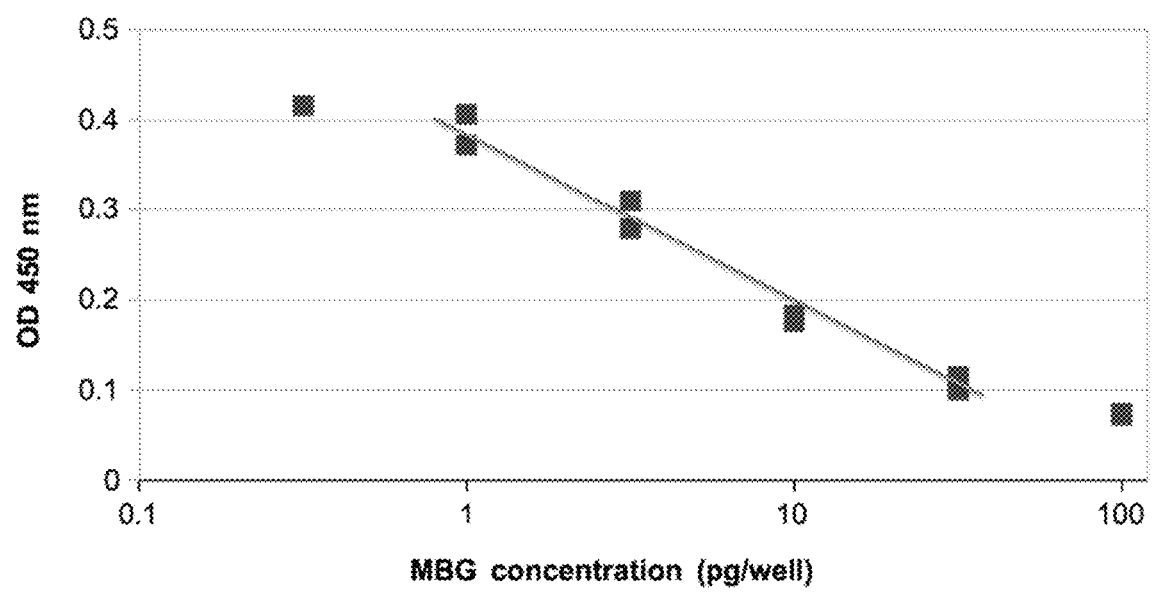
FIG. 5 shows a standard curve for MBG in a competitive ELISA assay for measuring MBG in a biological sample.

MBG levels in urine were measured by competitive ELISA, modified from Abi-Ghanem et al. J Immunoassay Immunochem. 32:31-46 (2011). Wells were coated with anti-MBG antibody. Samples containing MBG (known or unknown) and MBG-BSA were then added to the wells. HRP-anti-BSA antibody was added to each well and then reacted with TMB (K&P Labs). Reactions were stopped and the wells were read at 450 nm. A standard curve was prepared using samples with known amounts of MBG (FIG. 5). Urine samples were assayed and compared to the standard curve. The concentration of MBG in the urine samples was calculated from the linear range of the standard curve. The amounts of MBG found in the urine samples were similar to values reported in the literature. For example, human urine sample #3 was analyzed in duplicate to obtain OD values of 0.140 and 0.149. From the standard curve, these values corresponded to 224.6+/−23.7 pg/mL MBG. While this example utilized urine samples to measure MBG, any biological fluid/sample could be used in the assay.

It is understood that, while particular embodiments have been illustrated and described, various modifications may be made thereto and are contemplated herein. It is also understood that the disclosure is not limited by the specific examples provided herein. The description and illustration of embodiments and examples of the disclosure herein are not intended to be construed in a limiting sense. It is further understood that all aspects of the disclosure are not limited to the specific depictions, configurations or relative proportions set forth herein, which may depend upon a variety of conditions and variables. Various modifications and variations in form and detail of the embodiments and examples of the disclosure will be apparent to a person skilled in the art. It is therefore contemplated that the disclosure also covers any and all such modifications, variations and equivalents.

We claim:

1. An anti-marinobufagenin antibody or a marinobufagenin binding antibody fragment thereof selected from the group consisting of
   an antibody H1L1 comprising a heavy chain variable region comprising SEQ ID NO: 9 and a light chain variable region comprising SEQ ID NO: 12;
   an antibody H1L2 comprising a heavy chain variable region comprising SEQ ID NO: 9 and a light chain variable region comprising SEQ ID NO: 13;
   an antibody H2L1 comprising a heavy chain variable region comprising SEQ ID NO: 10 and a light chain variable region comprising SEQ ID NO: 12;
   an antibody H2L2 comprising a heavy chain variable region comprising SEQ ID NO: 10 and a light chain variable region comprising SEQ ID NO: 13;
   an antibody H3L1 comprising a heavy chain variable region comprising SEQ ID NO: 11 and a light chain variable region comprising SEQ ID NO: 12; and
   an antibody H3L2 comprising a heavy chain variable region comprising SEQ ID NO: 11 and a light chain variable region comprising SEQ ID NO: 13.

2. The anti-marinobufagenin antibody of claim 1, wherein the anti-marinobufagenin antibody is H1L1.

3. The anti-marinobufagenin antibody of claim 1, wherein the anti-marinobufagenin antibody is H1L2.

4. The anti-marinobufagenin antibody of claim 1, wherein the anti-marinobufagenin antibody is H2L1.

5. The anti-marinobufagenin antibody of claim 1, wherein the anti-marinobufagenin antibody is H2L2.

6. The anti-marinobufagenin antibody of claim 1, wherein the anti-marinobufagenin antibody is H3L1.

7. The anti-marinobufagenin antibody of claim 1, wherein the anti-marinobufagenin antibody is H3L2.

8. The anti-marinobufagenin antibody or a marinobufagenin binding antibody fragment of claim 1 which is a marinobufagenin binding antibody fragment.

9. The marinobufagenin binding antibody fragment of claim 8 wherein the antibody fragment is conjugated to a moiety selected from the group consisting of a polyethylene glycol and a human serum albumin.

10. The marinobufagenin binding antibody fragment of claim 9 wherein the moiety is a polyethylene glycol.

11. The marinobufagenin binding antibody fragment of claim 8, wherein the antibody fragment is an Fab fragment.

12. The marinobufagenin binding antibody fragment of claim 8, wherein the antibody fragment is a recombinant fragment.

13. The anti-marinobufagenin antibody of claim 1, wherein the antibody is a single chain antibody.

14. The anti-marinobufagenin antibody of claim 1, wherein the antibody is an IgG.

15. The anti-marinobufagenin antibody of claim 14, wherein the antibody is an IgG1.

16. The anti-marinobufagenin antibody of claim 14, wherein the antibody is an IgG2.

17. The anti-marinobufagenin antibody of claim 14, wherein the antibody is an IgG4.

* * * * *

SEQUENCE LISTING

```
<160> NUMBER OF SEQ ID NOS: 103

<210> SEQ ID NO 1
<211> LENGTH: 117
<212> TYPE: PRT
<213> ORGANISM: Mus musculus

<400> SEQUENCE: 1

Glu Val Gln Leu Gln Glu Ser Gly Pro Ser Leu Val Lys Pro Ser Gln
1               5                   10                  15

Thr Leu Ser Leu Thr Cys Ser Val Thr Gly Asp Ser Ile Thr Ser Gly
            20                  25                  30

Tyr Trp Asn Trp Ile Arg Lys Phe Pro Gly Asn Lys Leu Glu Tyr Met
        35                  40                  45

Gly Tyr Ile Ser Tyr Ser Gly Thr Thr Tyr Tyr Asn Pro Ser Leu Lys
    50                  55                  60

Ser Arg Ile Ser Ile Thr Arg Asp Thr Ser Lys Asn Gln Tyr Tyr Leu
65                  70                  75                  80

Gln Leu Asn Ser Val Thr Thr Glu Asp Thr Ala Thr Tyr Tyr Cys Ala
                85                  90                  95

Arg Ala Arg Tyr Gly Tyr Gly Phe Asp Tyr Trp Gly Gln Gly Thr Thr
            100                 105                 110

Leu Thr Val Ser Ser
        115

<210> SEQ ID NO 2
<211> LENGTH: 112
<212> TYPE: PRT
<213> ORGANISM: Mus musculus

<400> SEQUENCE: 2

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
```

```
                20                  25                  30
Asn Arg Asn Thr Tyr Leu Glu Trp Tyr Leu Gln Lys Pro Gly Gln Ser
                35                  40                  45
Pro Lys Leu Leu Ile Tyr Lys Val Ser Asn Arg Phe Ser Gly Val Pro
                50                  55                  60
Asp Arg Phe Ser Gly Ser Gly Ser Gly Thr Asp Phe Thr Leu Lys Ile
65                  70                  75                  80
Ser Arg Val Glu Ala Glu Asp Leu Gly Val Tyr Tyr Cys Phe Gln Gly
                85                  90                  95
Ser His Val Pro Leu Thr Phe Gly Ala Gly Thr Lys Leu Glu Leu Lys
                100                 105                 110
```

<210> SEQ ID NO 3
<211> LENGTH: 9
<212> TYPE: PRT
<213> ORGANISM: Mus musculus

<400> SEQUENCE: 3

```
Asp Ser Ile Thr Ser Gly Tyr Trp Asn
1               5
```

<210> SEQ ID NO 4
<211> LENGTH: 16
<212> TYPE: PRT
<213> ORGANISM: Mus musculus

<400> SEQUENCE: 4

```
Tyr Ile Ser Tyr Ser Gly Thr Thr Tyr Tyr Asn Pro Ser Leu Lys Ser
1               5                   10                  15
```

<210> SEQ ID NO 5
<211> LENGTH: 9
<212> TYPE: PRT
<213> ORGANISM: Mus musculus

<400> SEQUENCE: 5

```
Ala Arg Tyr Gly Tyr Gly Phe Asp Tyr
1               5
```

<210> SEQ ID NO 6
<211> LENGTH: 16
<212> TYPE: PRT
<213> ORGANISM: Mus musculus

<400> SEQUENCE: 6

```
Arg Ser Ser Gln Ser Ile Val His Ser Asn Arg Asn Thr Tyr Leu Glu
1               5                   10                  15
```

<210> SEQ ID NO 7
<211> LENGTH: 7
<212> TYPE: PRT
<213> ORGANISM: Mus musculus

<400> SEQUENCE: 7

```
Lys Val Ser Asn Arg Phe Ser
1               5
```

<210> SEQ ID NO 8
<211> LENGTH: 9
<212> TYPE: PRT
<213> ORGANISM: Mus musculus

<400> SEQUENCE: 8

```
Phe Gln Gly Ser His Val Pro Leu Thr
1               5

<210> SEQ ID NO 9
<211> LENGTH: 117
<212> TYPE: PRT
<213> ORGANISM: Artificial Sequence
<220> FEATURE:
<223> OTHER INFORMATION: Humanized VH sequence

<400> SEQUENCE: 9

Gln Val Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Thr Ser Gly
            20                  25                  30

Tyr Trp Asn Trp Ile Arg Gln Pro Pro Gly Lys Gly Leu Glu Trp Ile
        35                  40                  45

Gly Tyr Ile Ser Tyr Ser Gly Thr Thr Tyr Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Tyr Gly Tyr Gly Phe Asp Tyr Trp Gly Gln Gly Thr Leu
            100                 105                 110

Val Thr Val Ser Ser
        115

<210> SEQ ID NO 10
<211> LENGTH: 117
<212> TYPE: PRT
<213> ORGANISM: Artificial Sequence
<220> FEATURE:
<223> OTHER INFORMATION: Humanized VH sequence

<400> SEQUENCE: 10

Glu Val Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Thr Ser Gly
            20                  25                  30

Tyr Trp Asn Trp Ile Arg Gln Pro Pro Gly Lys Gly Leu Glu Tyr Ile
        35                  40                  45

Gly Tyr Ile Ser Tyr Ser Gly Thr Thr Tyr Tyr Asn Pro Ser Leu Lys
    50                  55                  60

Ser Arg Val Thr Ile Ser Arg Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Tyr Gly Tyr Gly Phe Asp Tyr Trp Gly Gln Gly Thr Leu
            100                 105                 110

Val Thr Val Ser Ser
        115

<210> SEQ ID NO 11
<211> LENGTH: 117
<212> TYPE: PRT
<213> ORGANISM: Artificial Sequence
<220> FEATURE:
<223> OTHER INFORMATION: Humanized VH sequence
```

<400> SEQUENCE: 11

Glu Val Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Thr Ser Gly
            20                  25                  30

Tyr Trp Asn Trp Ile Arg Gln Pro Pro Gly Lys Gly Leu Glu Tyr Met
        35                  40                  45

Gly Tyr Ile Ser Tyr Ser Gly Thr Thr Tyr Tyr Asn Pro Ser Leu Lys
    50                  55                  60

Ser Arg Ile Thr Ile Ser Arg Asp Thr Ser Lys Asn Gln Tyr Ser Leu
65                  70                  75                  80

Lys Leu Ser Ser Val Thr Ala Ala Asp Thr Ala Val Tyr Tyr Cys Ala
                85                  90                  95

Arg Ala Arg Tyr Gly Tyr Gly Phe Asp Tyr Trp Gly Gln Gly Thr Leu
            100                 105                 110

Val Thr Val Ser Ser
            115

<210> SEQ ID NO 12
<211> LENGTH: 112
<212> TYPE: PRT
<213> ORGANISM: Artificial Sequence
<220> FEATURE:
<223> OTHER INFORMATION: Humanized VL sequence

<400> SEQUENCE: 12

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Ile Val His Ser
            20                  25                  30

Asn Arg Asn Thr Tyr Leu Glu Trp Phe Gln Gln Arg Pro Gly Gln Ser
        35                  40                  45

Pro Arg Arg Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Leu Thr Phe Gly Gly Gly Thr Lys Val Glu Ile Lys
            100                 105                 110

<210> SEQ ID NO 13
<211> LENGTH: 112
<212> TYPE: PRT
<213> ORGANISM: Artificial Sequence
<220> FEATURE:
<223> OTHER INFORMATION: Humanized VL sequence

<400> SEQUENCE: 13

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Ile Val His Ser
            20                  25                  30

Asn Arg Asn Thr Tyr Leu Glu Trp Tyr Gln Gln Arg Pro Gly Gln Ser
        35                  40                  45

Pro Arg Leu Leu Ile Tyr Lys Val Ser Asn Arg Phe Ser Gly Val Pro
    50                  55                  60

```
Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Phe Gln Gly
                 85                  90                  95

Ser His Val Pro Leu Thr Phe Gly Gly Gly Thr Lys Val Glu Ile Lys
            100                 105                 110
```

<210> SEQ ID NO 14
<211> LENGTH: 122
<212> TYPE: PRT
<213> ORGANISM: Homo sapiens

<400> SEQUENCE: 14

```
Gln Val Gln Leu Gln Glu Ser Gly Pro Gly Leu Val Lys Pro Ser Glu
  1               5                  10                  15

Thr Leu Ser Leu Thr Cys Thr Val Ser Gly Gly Ser Ile Ser Ser Ser
             20                  25                  30

Ser Tyr Tyr Trp Gly Trp Ile Arg Gln Pro Pro Gly Lys Gly Leu Glu
         35                  40                  45

Trp Ile Gly Ser Ile Tyr Tyr Ser Gly Ser Thr Tyr Tyr Asn Pro Ser
 50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
             85                  90                  95

Cys Ala Arg Ala Arg Tyr Asn Trp Asn Tyr Val Leu Phe Asp Tyr Trp
            100                 105                 110

Gly Gln Gly Thr Leu Val Thr Val Ser Ser
            115                 120
```

<210> SEQ ID NO 15
<211> LENGTH: 111
<212> TYPE: PRT
<213> ORGANISM: Homo sapiens

<400> SEQUENCE: 15

```
Gln Ala Val Leu Thr Gln Pro Ser Ser Val Ser Ala Ala Pro Arg Gln
  1               5                  10                  15

Arg Val Thr Ile Ser Cys Ser Gly Ser Ala Ser Asn Ile Gly Arg Asn
             20                  25                  30

Gly Val Ser Trp Tyr His Gln Val Pro Gly Lys Ala Pro Arg Leu Leu
         35                  40                  45

Leu Ser His Asp Gly Leu Val Thr Gly Val Pro Asp Arg Leu Ser
 50                  55                  60

Val Ser Lys Ser Gly Thr Ser Ala Ser Leu Ala Ile Ser Gly Leu His
 65                  70                  75                  80

Ser Asp Asp Glu Gly Asp Tyr Tyr Cys Ala Val Trp Asp Asp Ser Leu
             85                  90                  95

Asn Ala Val Val Phe Gly Gly Gly Thr Lys Leu Thr Val Leu Ser
            100                 105                 110
```

<210> SEQ ID NO 16
<211> LENGTH: 10
<212> TYPE: PRT
<213> ORGANISM: Homo sapiens

<400> SEQUENCE: 16

Gly Gly Ser Ile Ser Ser Ser Tyr Tyr
1               5                   10

<210> SEQ ID NO 17
<211> LENGTH: 7
<212> TYPE: PRT
<213> ORGANISM: Homo sapiens

<400> SEQUENCE: 17

Ile Tyr Tyr Ser Gly Ser Thr
1               5

<210> SEQ ID NO 18
<211> LENGTH: 14
<212> TYPE: PRT
<213> ORGANISM: Homo sapiens

<400> SEQUENCE: 18

Ala Arg Ala Arg Tyr Asn Trp Asn Tyr Val Leu Phe Asp Tyr
1               5                   10

<210> SEQ ID NO 19
<211> LENGTH: 8
<212> TYPE: PRT
<213> ORGANISM: Homo sapiens

<400> SEQUENCE: 19

Ala Ser Asn Ile Gly Arg Asn Gly
1               5

<210> SEQ ID NO 20
<211> LENGTH: 3
<212> TYPE: PRT
<213> ORGANISM: Homo sapiens

<400> SEQUENCE: 20

His Asp Gly
1

<210> SEQ ID NO 21
<211> LENGTH: 11
<212> TYPE: PRT
<213> ORGANISM: Homo sapiens

<400> SEQUENCE: 21

Ala Val Trp Asp Asp Ser Leu Asn Ala Val Val
1               5                   10

<210> SEQ ID NO 22
<211> LENGTH: 120
<212> TYPE: PRT
<213> ORGANISM: Homo sapiens

<400> SEQUENCE: 22

Gln Leu Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Gly Trp Ile Arg Gln Pro Pro Gly Lys Gly Leu Glu
        35                  40                  45

Trp Ile Gly Ser Ile Tyr Tyr Ser Gly Asn Thr Tyr Tyr Asn Pro Ser
    50                  55                  60

Leu Lys Ser Arg Val Thr Ile Ser Val Asp Thr Ser Lys Asn Gln Phe

```
                65                  70                  75                  80
            Ser Leu Lys Leu Ser Ser Val Thr Ala Ala Asp Thr Ala Val Tyr Tyr
                                85                  90                  95

Cys Ala Arg Ala Ser Ile Ala Ala Arg Thr Phe Asp Tyr Trp Gly Gln
                            100                 105                 110

Gly Thr Leu Val Thr Val Ser Ser
                        115                 120

<210> SEQ ID NO 23
<211> LENGTH: 110
<212> TYPE: PRT
<213> ORGANISM: Homo sapiens

<400> SEQUENCE: 23

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
                20                  25                  30

Tyr Val Ser Trp Tyr Gln Gln Leu Pro Gly Thr Ala Pro Lys Leu Leu
            35                  40                  45

Ile Tyr Asp Asn Asn Lys Arg Pro Ser Gly Ile Pro Asp Arg Phe Ser
        50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Tyr Val Phe Gly Thr Gly Thr Lys Val Thr Val Leu
            100                 105                 110

<210> SEQ ID NO 24
<211> LENGTH: 10
<212> TYPE: PRT
<213> ORGANISM: Homo sapiens

<400> SEQUENCE: 24

Gly Gly Ser Ile Ser Ser Gly Gly Tyr Tyr
1               5                   10

<210> SEQ ID NO 25
<211> LENGTH: 7
<212> TYPE: PRT
<213> ORGANISM: Homo sapiens

<400> SEQUENCE: 25

Ile Tyr Tyr Ser Gly Asn Thr
1               5

<210> SEQ ID NO 26
<211> LENGTH: 12
<212> TYPE: PRT
<213> ORGANISM: Homo sapiens

<400> SEQUENCE: 26

Ala Arg Ala Ser Ile Ala Ala Arg Thr Phe Asp Tyr
1               5                   10

<210> SEQ ID NO 27
<211> LENGTH: 8
<212> TYPE: PRT
<213> ORGANISM: Homo sapiens
```

-continued

```
<400> SEQUENCE: 27

Ser Ser Asn Ile Gly Asn Asn Tyr
1               5

<210> SEQ ID NO 28
<211> LENGTH: 3
<212> TYPE: PRT
<213> ORGANISM: Homo sapiens

<400> SEQUENCE: 28

Asp Asn Asn
1

<210> SEQ ID NO 29
<211> LENGTH: 11
<212> TYPE: PRT
<213> ORGANISM: Homo sapiens

<400> SEQUENCE: 29

Gly Thr Trp Asp Ser Ser Leu Ser Ala Tyr Val
1               5                   10

<210> SEQ ID NO 30
<211> LENGTH: 118
<212> TYPE: PRT
<213> ORGANISM: Homo sapiens

<400> SEQUENCE: 30

Gln Leu Gln Leu Gln Glu Ser Gly Pro Gly Leu Val Lys Pro Ser Glu
1               5                   10                  15

Thr Leu Ser Leu Thr Cys Thr Val Ser Gly Ser Ile Ser Ser Tyr
            20                  25                  30

Tyr Trp Gly Trp Ile Arg Gln Pro Pro Gly Lys Gly Leu Glu Trp Ile
        35                  40                  45

Gly Ser Ile Tyr Tyr Ser Gly Ser Thr Tyr Tyr Asn Pro Ser Leu Lys
    50                  55                  60

Ser Arg Val Thr Ile Ser Val Asp Thr Ser Lys Asn Gln Phe Ser Leu
65                  70                  75                  80

Gln Leu Lys Ser Val Thr Pro Glu Asp Thr Ala Val Tyr Tyr Cys Ala
                85                  90                  95

Arg Val Arg Pro Pro Ala Ala Thr Phe Asp Tyr Trp Gly Gln Gly Thr
            100                 105                 110

Leu Val Thr Val Ser Ser
        115

<210> SEQ ID NO 31
<211> LENGTH: 110
<212> TYPE: PRT
<213> ORGANISM: Homo sapiens

<400> SEQUENCE: 31

Gln Ser Val Val Thr Gln Pro Pro Ser Val Ser Ala Ala Pro Gly Gln
1               5                   10                  15

Lys Val Ser Ile Ser Cys Ser Gly Gly Ser Ser Asn Ile Gly Asn Asn
            20                  25                  30

Tyr Val Ser Trp Tyr Gln Gln Leu Pro Gly Thr Ala Pro Arg Leu Leu
        35                  40                  45

Ile Tyr Glu Asn Asn Asn Arg Pro Ser Gly Ile Pro Asp Arg Phe Ser
    50                  55                  60
```

```
Gly Ser Lys Ser Gly Thr Ser Ala Thr Leu Gly Ile Thr Gly Leu Gln
 65                  70                  75                  80

Thr Gly Asp Glu Ala Asp Tyr Tyr Cys Gly Thr Trp Asp Ser Ser Leu
                 85                  90                  95

Arg Ala Val Val Phe Gly Gly Gly Thr Lys Leu Thr Val Leu
            100                 105                 110

<210> SEQ ID NO 32
<211> LENGTH: 8
<212> TYPE: PRT
<213> ORGANISM: Homo sapiens

<400> SEQUENCE: 32

Gly Gly Ser Ile Ser Ser Tyr Tyr
1               5

<210> SEQ ID NO 33
<211> LENGTH: 12
<212> TYPE: PRT
<213> ORGANISM: Homo sapiens

<400> SEQUENCE: 33

Ala Arg Val Arg Pro Ala Ala Thr Phe Asp Tyr
1               5                  10

<210> SEQ ID NO 34
<211> LENGTH: 3
<212> TYPE: PRT
<213> ORGANISM: Homo sapiens

<400> SEQUENCE: 34

Glu Asn Asn
1

<210> SEQ ID NO 35
<211> LENGTH: 11
<212> TYPE: PRT
<213> ORGANISM: Homo sapiens

<400> SEQUENCE: 35

Gly Thr Trp Asp Ser Ser Leu Arg Ala Val Val
1               5                  10

<210> SEQ ID NO 36
<211> LENGTH: 119
<212> TYPE: PRT
<213> ORGANISM: Homo sapiens

<400> SEQUENCE: 36

Gln Val Gln Leu Gln Glu Ser Gly Pro Gly Leu Val Lys Pro Ser Glu
1               5                  10                  15

Thr Leu Ser Leu Thr Cys Thr Val Ser Gly Gly Ser Ile Ser Ser Ser
             20                  25                  30

Ser Tyr Tyr Trp Gly Trp Ile Arg Gln Pro Pro Gly Lys Gly Leu Glu
         35                  40                  45

Trp Ile Gly Ser Ile Tyr Tyr Ser Gly Ser Thr Tyr Tyr Asn Pro Ser
     50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95
```

```
Cys Ala Arg Val Asn Leu Arg Gly Ala Phe Asp Ile Trp Gly Gln Gly
                100                 105                 110

Thr Thr Val Thr Val Ser Ser
            115

<210> SEQ ID NO 37
<211> LENGTH: 111
<212> TYPE: PRT
<213> ORGANISM: Homo sapiens

<400> SEQUENCE: 37

Gln Ser Val Val Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Glu Asn Asn Lys Arg Pro Ser Gly Ile Pro Asp Arg Phe
    50                  55                  60

Ser Gly Ser Lys Ser Gly Thr Ser Ala Thr Leu Gly Ile Thr Gly Leu
65                  70                  75                  80

Gln Thr Gly Asp Glu Ala Asp Tyr Tyr Cys Gly Thr Trp Asp Ser Ser
                85                  90                  95

Leu Ser Ala Val Val Phe Gly Gly Gly Thr Lys Leu Thr Val Leu
            100                 105                 110

<210> SEQ ID NO 38
<211> LENGTH: 11
<212> TYPE: PRT
<213> ORGANISM: Homo sapiens

<400> SEQUENCE: 38

Ala Arg Val Asn Leu Arg Gly Ala Phe Asp Ile
1               5                   10

<210> SEQ ID NO 39
<211> LENGTH: 9
<212> TYPE: PRT
<213> ORGANISM: Homo sapiens

<400> SEQUENCE: 39

Ser Ser Asn Ile Gly Ala Gly Tyr Asp
1               5

<210> SEQ ID NO 40
<211> LENGTH: 11
<212> TYPE: PRT
<213> ORGANISM: Homo sapiens

<400> SEQUENCE: 40

Gly Thr Trp Asp Ser Ser Leu Ser Ala Val Val
1               5                   10

<210> SEQ ID NO 41
<211> LENGTH: 125
<212> TYPE: PRT
<213> ORGANISM: Homo sapiens

<400> SEQUENCE: 41

Gln Leu Gln Leu Gln Glu Ser Gly Pro Gly Leu Val Lys Pro Ser Glu
1               5                   10                  15
```

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
            85                  90                  95

Cys Ala Arg Val Val Val Ala Arg Thr Gly Thr Thr Ile Ser Trp Phe
            100                 105                 110

Asp Pro Trp Gly Gln Gly Thr Leu Val Thr Val Ser Ser
            115                 120                 125

<210> SEQ ID NO 42
<211> LENGTH: 115
<212> TYPE: PRT
<213> ORGANISM: Homo sapiens

<400> SEQUENCE: 42

Gln Ala Val Leu Thr Gln Pro Ser Ser Leu Ser Ala Ser Pro Gly Ala
1               5                   10                  15

Ser Ala Ser Leu Thr Cys Thr Leu Arg Ser Gly Ile Asn Val Asp Thr
            20                  25                  30

Tyr Arg Ile Tyr Trp Tyr Gln Gln Lys Pro Gly Ser Pro Pro Gln Tyr
        35                  40                  45

Leu Leu Arg Tyr Lys Ser Asp Ser Asp Lys Gln Gln Gly Ser Gly Val
    50                  55                  60

Pro Ser Arg Phe Ser Gly Ser Lys Asp Ala Ser Ala Asn Ala Gly Ile
65                  70                  75                  80

Leu Leu Ile Ser Gly Leu Gln Ser Glu Asp Glu Ala Asp Tyr Tyr Cys
            85                  90                  95

Val Ile Trp His Ser Ser Ala Trp Val Phe Gly Gly Gly Thr Lys Leu
            100                 105                 110

Thr Val Leu
        115

<210> SEQ ID NO 43
<211> LENGTH: 17
<212> TYPE: PRT
<213> ORGANISM: Homo sapiens

<400> SEQUENCE: 43

Ala Arg Val Val Val Ala Arg Thr Gly Thr Thr Ile Ser Trp Phe Asp
1               5                   10                  15

Pro

<210> SEQ ID NO 44
<211> LENGTH: 9
<212> TYPE: PRT
<213> ORGANISM: Homo sapiens

<400> SEQUENCE: 44

Ser Gly Ile Asn Val Asp Thr Tyr Arg
1               5

<210> SEQ ID NO 45

```
<211> LENGTH: 7
<212> TYPE: PRT
<213> ORGANISM: Homo sapiens

<400> SEQUENCE: 45

Tyr Lys Ser Asp Ser Asp Lys
1               5

<210> SEQ ID NO 46
<211> LENGTH: 9
<212> TYPE: PRT
<213> ORGANISM: Homo sapiens

<400> SEQUENCE: 46

Val Ile Trp His Ser Ser Ala Trp Val
1               5

<210> SEQ ID NO 47
<211> LENGTH: 121
<212> TYPE: PRT
<213> ORGANISM: Homo sapiens

<400> SEQUENCE: 47

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Leu Arg Tyr Ser Ser Gly Trp Tyr Ala Asp Pro Trp Gly
            100                 105                 110

Gln Gly Thr Leu Val Thr Val Ser Ser
        115                 120

<210> SEQ ID NO 48
<211> LENGTH: 110
<212> TYPE: PRT
<213> ORGANISM: Homo sapiens

<400> SEQUENCE: 48

Leu Pro Val Leu Thr Gln Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Ile Val Asn Trp Tyr Gln Gln Leu Pro Gly Thr Ala Pro Lys Leu Leu
        35                  40                  45

Ile Tyr Asn Asn Asn Gln Arg Pro Ser Gly Val Pro Asp Arg Phe Ser
    50                  55                  60

Gly Ser Lys Ser Gly Ala Ser Ala Ser Leu Ala Ile Ser Gly Leu Gln
65                  70                  75                  80

Ser Glu Asp Glu Ala Asp Tyr Tyr Cys Val Ala Trp Asp Gly Ser Leu
                85                  90                  95

Ser Gly Val Val Phe Gly Gly Gly Thr Lys Leu Thr Val Leu
```

<210> SEQ ID NO 49
<211> LENGTH: 13
<212> TYPE: PRT
<213> ORGANISM: Homo sapiens

<400> SEQUENCE: 49

Ala Arg Leu Arg Tyr Ser Ser Gly Trp Tyr Ala Asp Pro
1               5                   10

<210> SEQ ID NO 50
<211> LENGTH: 8
<212> TYPE: PRT
<213> ORGANISM: Homo sapiens

<400> SEQUENCE: 50

Ser Ser Asn Ile Gly Ser Asn Ile
1               5

<210> SEQ ID NO 51
<211> LENGTH: 3
<212> TYPE: PRT
<213> ORGANISM: Homo sapiens

<400> SEQUENCE: 51

Asn Asn Asn
1

<210> SEQ ID NO 52
<211> LENGTH: 11
<212> TYPE: PRT
<213> ORGANISM: Homo sapiens

<400> SEQUENCE: 52

Val Ala Trp Asp Gly Ser Leu Ser Gly Val Val
1               5                   10

<210> SEQ ID NO 53
<211> LENGTH: 121
<212> TYPE: PRT
<213> ORGANISM: Homo sapiens

<400> SEQUENCE: 53

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Phe His Thr Trp Ala Pro Arg Ala Phe Asp Ile Trp Gly
            100                 105                 110

Gln Gly Thr Met Val Thr Val Ser Ser
        115                 120

```
<210> SEQ ID NO 54
<211> LENGTH: 109
<212> TYPE: PRT
<213> ORGANISM: Homo sapiens

<400> SEQUENCE: 54

Gln Ser Val Val Thr Gln Pro Pro Ser Val Ser Ala Ala Pro Gly Gln
1               5                   10                  15

Glu Val Thr Ile Ser Cys Ser Gly Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Leu Phe Gly Gly Gly Thr Lys Leu Thr Val Leu
            100                 105

<210> SEQ ID NO 55
<211> LENGTH: 13
<212> TYPE: PRT
<213> ORGANISM: Homo sapiens

<400> SEQUENCE: 55

Ala Arg Phe His Thr Trp Ala Pro Arg Ala Phe Asp Ile
1               5                   10

<210> SEQ ID NO 56
<211> LENGTH: 10
<212> TYPE: PRT
<213> ORGANISM: Homo sapiens

<400> SEQUENCE: 56

Gly Thr Trp Asp Ser Ser Leu Ser Ala Leu
1               5                   10

<210> SEQ ID NO 57
<211> LENGTH: 120
<212> TYPE: PRT
<213> ORGANISM: Homo sapiens

<400> SEQUENCE: 57

Gln Val Gln Leu Gln Glu Ser Gly Ser Gly Leu Val Lys Pro Ser Gln
1               5                   10                  15

Thr Leu Ser Leu Thr Cys Thr Val Ser Gly Gly Ser Ile Ser Ser Ser
            20                  25                  30

Gly Tyr Tyr Trp Gly Trp Ile Arg Gln Pro Pro Gly Lys Gly Leu Glu
        35                  40                  45

Trp Ile Gly Ser Ile Tyr His Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Val Gln Leu Trp Gln Arg Gly Phe Asp Tyr Trp Gly Gln
            100                 105                 110
```

```
Gly Thr Leu Val Thr Val Ser Ser
        115             120
```

<210> SEQ ID NO 58
<211> LENGTH: 112
<212> TYPE: PRT
<213> ORGANISM: Homo sapiens

<400> SEQUENCE: 58

```
Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Asn Arg Val Glu Ala Glu Asp Val Gly Val Tyr Tyr Cys Met Gln Ala
                85                  90                  95

Leu Gln Ala Pro Leu Thr Phe Gly Gly Gly Thr Lys Val Glu Ile Lys
            100                 105                 110
```

<210> SEQ ID NO 59
<211> LENGTH: 10
<212> TYPE: PRT
<213> ORGANISM: Homo sapiens

<400> SEQUENCE: 59

```
Gly Gly Ser Ile Ser Ser Ser Gly Tyr Tyr
1               5                   10
```

<210> SEQ ID NO 60
<211> LENGTH: 7
<212> TYPE: PRT
<213> ORGANISM: Homo sapiens

<400> SEQUENCE: 60

```
Ile Tyr His Ser Gly Ser Thr
1               5
```

<210> SEQ ID NO 61
<211> LENGTH: 12
<212> TYPE: PRT
<213> ORGANISM: Homo sapiens

<400> SEQUENCE: 61

```
Ala Arg Val Gln Leu Trp Gln Arg Gly Phe Asp Tyr
1               5                   10
```

<210> SEQ ID NO 62
<211> LENGTH: 11
<212> TYPE: PRT
<213> ORGANISM: Homo sapiens

<400> SEQUENCE: 62

```
Gln Ser Leu Leu His Ser Asn Gly Tyr Asn Tyr
1               5                   10
```

<210> SEQ ID NO 63
<211> LENGTH: 3

<212> TYPE: PRT
<213> ORGANISM: Homo sapiens

<400> SEQUENCE: 63

Leu Gly Ser
1

<210> SEQ ID NO 64
<211> LENGTH: 9
<212> TYPE: PRT
<213> ORGANISM: Homo sapiens

<400> SEQUENCE: 64

Met Gln Ala Leu Gln Ala Pro Leu Thr
1               5

<210> SEQ ID NO 65
<211> LENGTH: 115
<212> TYPE: PRT
<213> ORGANISM: Homo sapiens

<400> SEQUENCE: 65

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Val
                85                  90                  95

Thr Trp Ser Asp Tyr Arg Asp Tyr Trp Gly Gln Gly Thr Leu Val Thr
            100                 105                 110

Val Ser Ser
        115

<210> SEQ ID NO 66
<211> LENGTH: 215
<212> TYPE: PRT
<213> ORGANISM: Homo sapiens

<400> SEQUENCE: 66

Glu Ile Val Met Thr Gln Ser Pro Gly Thr Leu Ser Leu Ser Pro Gly
1               5                   10                  15

Glu Arg Ala Thr Leu Ser Cys Arg Ala Ser Gln Ser Val Thr Ser Arg
            20                  25                  30

Arg Val Ala Trp Phe Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Leu Thr Phe Gly Gly Gly Thr Lys Val Glu Ile Arg Arg Thr Val Ala
            100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
        130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 67
<211> LENGTH: 8
<212> TYPE: PRT
<213> ORGANISM: Homo sapiens

<400> SEQUENCE: 67

Gly Gly Ser Phe Ser Gly Tyr Tyr
1               5

<210> SEQ ID NO 68
<211> LENGTH: 7
<212> TYPE: PRT
<213> ORGANISM: Homo sapiens

<400> SEQUENCE: 68

Ile Asn His Ser Gly Ser Thr
1               5

<210> SEQ ID NO 69
<211> LENGTH: 9
<212> TYPE: PRT
<213> ORGANISM: Homo sapiens

<400> SEQUENCE: 69

Val Thr Trp Ser Asp Tyr Arg Asp Tyr
1               5

<210> SEQ ID NO 70
<211> LENGTH: 7
<212> TYPE: PRT
<213> ORGANISM: Homo sapiens

<400> SEQUENCE: 70

Gln Ser Val Thr Ser Arg Arg
1               5

<210> SEQ ID NO 71
<211> LENGTH: 3
<212> TYPE: PRT
<213> ORGANISM: Homo sapiens

<400> SEQUENCE: 71

Gly Ala Ser
1

<210> SEQ ID NO 72

```
<211> LENGTH: 9
<212> TYPE: PRT
<213> ORGANISM: Homo sapiens

<400> SEQUENCE: 72

Gln Gln Tyr Gly Ser Ser Pro Leu Thr
1               5

<210> SEQ ID NO 73
<211> LENGTH: 126
<212> TYPE: PRT
<213> ORGANISM: Homo sapiens

<400> SEQUENCE: 73

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Gly Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Thr Thr Tyr Ser Tyr Gly Pro Gly Phe Asp Pro Trp Gly
            100                 105                 110

Gln Gly Thr Leu Val Thr Val Ser Ala Ser Thr Lys Gly
        115                 120                 125

<210> SEQ ID NO 74
<211> LENGTH: 216
<212> TYPE: PRT
<213> ORGANISM: Homo sapiens

<400> SEQUENCE: 74

Gln Ser Val Val Thr Gln Pro Pro Ser Val Ser Ala Ala Pro Gly Gln
1               5                   10                  15

Lys Val Thr Ile Ser Cys Ser Gly Ser Ser Ser Asn Ile Gly Thr Tyr
            20                  25                  30

Tyr Val Ser Trp Tyr Gln Gln Phe Pro Gly Thr Val Pro Lys Leu Leu
        35                  40                  45

Ile Tyr Asp Asn Thr Gln Arg Pro Ser Glu Ile Pro Asp Arg Phe Ser
    50                  55                  60

Ala Ser Lys Ser Gly Thr Ser Val Thr Leu Asp Ile Thr Gly Leu Gln
65                  70                  75                  80

Thr Gly Asp Glu Gly Asp Tyr Tyr Cys Ala Thr Trp Asp Ser Asn Leu
                85                  90                  95

Lys Ser Val Val Phe Gly Gly Gly Thr Lys Val Ala Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Gly Ser Pro Val Lys
145                 150                 155                 160
```

```
Ala Gly Val Glu Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215
```

<210> SEQ ID NO 75
<211> LENGTH: 7
<212> TYPE: PRT
<213> ORGANISM: Homo sapiens

<400> SEQUENCE: 75

```
Ile Tyr Tyr Ser Gly Gly Thr
1               5
```

<210> SEQ ID NO 76
<211> LENGTH: 13
<212> TYPE: PRT
<213> ORGANISM: Homo sapiens

<400> SEQUENCE: 76

```
Ala Arg Thr Thr Tyr Ser Tyr Gly Pro Gly Phe Asp Pro
1               5                   10
```

<210> SEQ ID NO 77
<211> LENGTH: 8
<212> TYPE: PRT
<213> ORGANISM: Homo sapiens

<400> SEQUENCE: 77

```
Ser Ser Asn Ile Gly Thr Tyr Tyr
1               5
```

<210> SEQ ID NO 78
<211> LENGTH: 3
<212> TYPE: PRT
<213> ORGANISM: Homo sapiens

<400> SEQUENCE: 78

```
Asp Asn Thr
1
```

<210> SEQ ID NO 79
<211> LENGTH: 11
<212> TYPE: PRT
<213> ORGANISM: Homo sapiens

<400> SEQUENCE: 79

```
Ala Thr Trp Asp Ser Asn Leu Lys Ser Val Val
1               5                   10
```

<210> SEQ ID NO 80
<211> LENGTH: 126
<212> TYPE: PRT
<213> ORGANISM: Homo sapiens

<400> SEQUENCE: 80

```
Gln Leu Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
```

```
              20                  25                  30
Gly Tyr Tyr Trp Ser Trp Ile Arg Gln Pro Gly Lys Gly Leu Glu
             35                  40                  45

Trp Ile Gly Ser Ile Tyr His Ser Gly Ser Thr Tyr Tyr Asn Pro Ser
 50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg Val Met Tyr Tyr Tyr Gly Ser Gly Ser Pro Tyr Trp Tyr
                100                 105                 110

Phe Asp Leu Trp Gly Arg Gly Thr Leu Val Thr Val Ser Ser
                115                 120                 125

<210> SEQ ID NO 81
<211> LENGTH: 181
<212> TYPE: PRT
<213> ORGANISM: Homo sapiens

<400> SEQUENCE: 81

Gln Ser Val Val Thr Gln Pro Pro Ser Val Ser Ala Ala Pro Gly Gln
 1               5                  10                  15

Lys Val Thr Ile Ser Cys Ser Gly Ser Ser Ser Asn Ile Gly Lys Asn
             20                  25                  30

Phe Val Ser Trp Tyr Gln Gln Phe Pro Gly Thr Ala Pro Lys Phe Leu
             35                  40                  45

Ile Tyr Glu Asn Ser Lys Arg Pro Ser Gly Ile Pro Asp Arg Ile Ser
 50                  55                  60

Gly Ser Lys Ser Gly Thr Ser Ala Thr Leu Ala Ile Thr Gly Leu Gln
 65                  70                  75                  80

Thr Gly Asp Glu Ala Asp Tyr Tyr Cys Gly Thr Trp Asp Ser Ser Leu
                 85                  90                  95

Ser Ala Val Val Phe Gly Gly Gly Thr Lys Leu Thr Val Leu Ser Gln
                100                 105                 110

Pro Lys Ala Ala Pro Ser Val Thr Leu Phe Pro Pro Ser Ser Glu Glu
            115                 120                 125

Leu Gln Ala Asn Lys Ala Thr Leu Val Cys Leu Ile Ser Asp Phe Tyr
        130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr
            180

<210> SEQ ID NO 82
<211> LENGTH: 10
<212> TYPE: PRT
<213> ORGANISM: Homo sapiens

<400> SEQUENCE: 82

Gly Gly Ser Ile Ser Ser Gly Gly Tyr Tyr
 1               5                  10

<210> SEQ ID NO 83
<211> LENGTH: 7
<212> TYPE: PRT
```

```
<213> ORGANISM: Homo sapiens

<400> SEQUENCE: 83

Ile Tyr His Ser Gly Ser Thr
1               5

<210> SEQ ID NO 84
<211> LENGTH: 18
<212> TYPE: PRT
<213> ORGANISM: Homo sapiens

<400> SEQUENCE: 84

Ala Arg Val Met Tyr Tyr Tyr Gly Ser Gly Ser Pro Tyr Trp Tyr Phe
1               5                   10                  15

Asp Leu

<210> SEQ ID NO 85
<211> LENGTH: 8
<212> TYPE: PRT
<213> ORGANISM: Homo sapiens

<400> SEQUENCE: 85

Ser Ser Asn Ile Gly Lys Asn Phe
1               5

<210> SEQ ID NO 86
<211> LENGTH: 3
<212> TYPE: PRT
<213> ORGANISM: Homo sapiens

<400> SEQUENCE: 86

Glu Asn Ser
1

<210> SEQ ID NO 87
<211> LENGTH: 122
<212> TYPE: PRT
<213> ORGANISM: Homo sapiens

<400> SEQUENCE: 87

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
                20                  25                  30

Ser Tyr Tyr Trp Gly Trp Ile Arg Gln Pro Pro Gly Lys Gly Leu Glu
            35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Leu Asp Thr Ser Lys Asn Gln Phe
65                  70                  75                  80

Ser Leu Lys Leu Ser Ser Leu Thr Ala Ala Asp Thr Ala Val Tyr Tyr
                85                  90                  95

Cys Ala Arg Val Pro Ala Ile Arg Ser Ser Ala Ile Phe Asp Tyr Trp
            100                 105                 110

Gly Gln Gly Thr Leu Val Thr Val Ser Ser
        115                 120

<210> SEQ ID NO 88
<211> LENGTH: 217
<212> TYPE: PRT
<213> ORGANISM: Homo sapiens
```

<400> SEQUENCE: 88

Gln Ser Val Val Thr Gln Pro Pro Ser Val Ser Ala Ala Pro Gly Gln
1               5                   10                  15

Lys Val Thr Ile Ser Cys Phe Gly Ser Arg Ser Asn Ile Gly Asn Asn
            20                  25                  30

Tyr Val Ser Trp Tyr Gln Gln Phe Pro Gly Thr Ala Pro Gln Leu Leu
        35                  40                  45

Ile Phe Asp Asn Asn Lys Arg Pro Ser Gly Ile Pro Asp Arg Phe Ser
    50                  55                  60

Gly Ser Lys Ser Gly Thr Ser Ala Ser Leu Gly Ile Thr Gly Val Gln
65                  70                  75                  80

Thr Gly Asp Glu Ala Glu Tyr Tyr Cys Gly Ala Trp Asp Ser Ser Leu
                85                  90                  95

Ser Ala Gly Ala Val Phe Gly Gly Thr Lys Leu Thr Val Leu Gly
            100                 105                 110

Gln Pro Lys Ala Ala Pro Ser Val Thr Leu Phe Pro Pro Ser Ser Glu
            115                 120                 125

Glu Leu Gln Ala Asn Lys Ala Thr Leu Val Cys Leu Ile Ser Asp Phe
130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
            210                 215

<210> SEQ ID NO 89
<211> LENGTH: 14
<212> TYPE: PRT
<213> ORGANISM: Homo sapiens

<400> SEQUENCE: 89

Ala Arg Val Pro Ala Ile Arg Ser Ser Ala Ile Phe Asp Tyr
1               5                   10

<210> SEQ ID NO 90
<211> LENGTH: 8
<212> TYPE: PRT
<213> ORGANISM: Homo sapiens

<400> SEQUENCE: 90

Arg Ser Asn Ile Gly Asn Asn Tyr
1               5

<210> SEQ ID NO 91
<211> LENGTH: 12
<212> TYPE: PRT
<213> ORGANISM: Homo sapiens

<400> SEQUENCE: 91

Gly Ala Trp Asp Ser Ser Leu Ser Ala Gly Ala Val
1               5                   10

```
<210> SEQ ID NO 92
<211> LENGTH: 121
<212> TYPE: PRT
<213> ORGANISM: Homo sapiens

<400> SEQUENCE: 92

Gln Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Ile Ser Ser Gly
            20                  25                  30

Tyr Tyr Trp Gly Trp Ile Arg Gln Pro Pro Gly Lys Gly Leu Glu Trp
        35                  40                  45

Ile Gly Ser Ile Tyr His Ser Gly Ser Thr Tyr Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Val Ala Pro Tyr Ser Ser Pro Ser Phe Asp Tyr Trp Gly
            100                 105                 110

Gln Gly Thr Leu Val Thr Val Ser Ser
        115                 120

<210> SEQ ID NO 93
<211> LENGTH: 216
<212> TYPE: PRT
<213> ORGANISM: Homo sapiens

<400> SEQUENCE: 93

Leu Pro Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Arg Asn
            20                  25                  30

Thr Gly Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Val Val Phe Gly Gly Gly Thr Lys Val Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Ala Glu Cys Ser
```

<210> SEQ ID NO 94
<211> LENGTH: 9
<212> TYPE: PRT
<213> ORGANISM: Homo sapiens

<400> SEQUENCE: 94

Gly Tyr Ser Ile Ser Ser Gly Tyr Tyr
1               5

<210> SEQ ID NO 95
<211> LENGTH: 7
<212> TYPE: PRT
<213> ORGANISM: Homo sapiens

<400> SEQUENCE: 95

Ile Tyr His Ser Gly Ser Thr
1               5

<210> SEQ ID NO 96
<211> LENGTH: 14
<212> TYPE: PRT
<213> ORGANISM: Homo sapiens

<400> SEQUENCE: 96

Ala Arg Val Ala Pro Tyr Ser Ser Ser Pro Ser Phe Asp Tyr
1               5                   10

<210> SEQ ID NO 97
<211> LENGTH: 8
<212> TYPE: PRT
<213> ORGANISM: Homo sapiens

<400> SEQUENCE: 97

Ser Ser Asn Ile Gly Arg Asn Thr
1               5

<210> SEQ ID NO 98
<211> LENGTH: 3
<212> TYPE: PRT
<213> ORGANISM: Homo sapiens

<400> SEQUENCE: 98

Ser Asn Asn
1

<210> SEQ ID NO 99
<211> LENGTH: 11
<212> TYPE: PRT
<213> ORGANISM: Homo sapiens

<400> SEQUENCE: 99

Ala Ala Trp Asp Asp Ser Leu Asn Gly Val Val
1               5                   10

<210> SEQ ID NO 100
<211> LENGTH: 118
<212> TYPE: PRT
<213> ORGANISM: Homo sapiens

<400> SEQUENCE: 100

Gln Val Gln Leu Gln Glu Ser Gly Pro Gly Leu Val Lys Pro Ser Glu
1               5                   10                  15

```
Thr Leu Ser Leu Thr Cys Thr Val Ser Gly Gly Ser Ile Ser Ser Ser
             20                  25                  30

Ser Tyr Tyr Trp Gly Trp Ile Arg Gln Pro Pro Gly Lys Gly Leu Glu
         35                  40                  45

Trp Ile Gly Ser Ile Tyr Tyr Ser Gly Ser Thr Tyr Tyr Asn Pro Ser
     50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
             85                  90                  95

Cys Ala Arg Phe Ser Arg Gly Gly Pro Phe Leu Trp Gly Arg Gly Thr
            100                 105                 110

Leu Val Thr Val Ser Ser
            115
```

<210> SEQ ID NO 101
<211> LENGTH: 216
<212> TYPE: PRT
<213> ORGANISM: Homo sapiens

<400> SEQUENCE: 101

```
Gln Ser Val Val Thr Gln Pro Pro Ser Val Ser Ala Ala Pro Gly Gln
 1               5                  10                  15

Lys Val Thr Ile Ser Cys Ser Gly Ser Ser Ser Asn Ile Gly Ser Tyr
             20                  25                  30

Ser Val Ser Trp Tyr Gln Gln Leu Pro Gly Thr Ala Pro Lys Leu Leu
         35                  40                  45

Ile Tyr Asp Asn Asn Lys Arg Pro Ser Gly Ile Pro Asp Arg Phe Ser
     50                  55                  60

Gly Ser Lys Ser Gly Thr Ser Ala Thr Leu Gly Ile Thr Gly Leu Gln
 65                  70                  75                  80

Thr Gly Asp Glu Ala Asp Tyr Tyr Cys Gly Thr Trp Asp Ser Ser Leu
             85                  90                  95

Ser Ala Tyr Val Phe Gly Ser Gly Thr Lys Val Thr Val Leu Gly Gln
            100                 105                 110

Pro Lys Ala Asn Pro Thr Val Thr Leu Phe Pro Pro Ser Ser Glu Glu
            115                 120                 125

Leu Gln Ala Asn Lys Ala Thr Leu Val Cys Leu Ile Ser Asp Phe Tyr
        130                 135                 140

Pro Gly Ala Val Thr Val Ala Trp Lys Ala Asp Gly Ser Pro Val Lys
145                 150                 155                 160

Ala Gly Val Glu Thr Thr Lys Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215
```

<210> SEQ ID NO 102
<211> LENGTH: 10
<212> TYPE: PRT
<213> ORGANISM: Homo sapiens

<400> SEQUENCE: 102

```
Ala Arg Phe Ser Arg Gly Gly Pro Phe Leu
1               5                   10

<210> SEQ ID NO 103
<211> LENGTH: 8
<212> TYPE: PRT
<213> ORGANISM: Homo sapiens

<400> SEQUENCE: 103

Ser Ser Asn Ile Gly Ser Tyr Ser
1               5
```